(12) United States Patent  (10) Patent No.: US 7,743,641 B2
Bailey et al.  (45) Date of Patent: Jun. 29, 2010

(54) COMPACT FIELD-MOUNTABLE GAS CHROMATOGRAPH WITH A DISPLAY SCREEN

(75) Inventors: Max A. Bailey, Bartlesville, OK (US);
Vince B. Hadley, Bartlesville, OK (US);
Jonathan W. Asher, Bartlesville, OK (US); Rodney Wayne Dilbeck, Bartlesville, OK (US); Anthony P. Walker, Bartlesville, OK (US); Steven Gene Lakey, Bartlesville, OK (US); Stephen P. Paetz, Bartlesville, OK (US); Brent E. Berry, Bartlesville, OK (US); Robert W. Rutledge, Collinsville, OK (US)

(73) Assignee: ABB Inc., Cary, NC (US)

( * ) Notice: Subject to any disclaimer, the term of this patent is extended or adjusted under 35 U.S.C. 154(b) by 631 days.

(21) Appl. No.: 11/515,079

(22) Filed: Sep. 1, 2006

(65) Prior Publication Data
US 2007/0089484 A1 Apr. 26, 2007

Related U.S. Application Data

(60) Provisional application No. 60/713,986, filed on Sep. 2, 2005.

(51) Int. Cl.
*G01N 30/04* (2006.01)
(52) U.S. Cl. ..................................... 73/23.42
(58) Field of Classification Search ............... 73/23.35, 73/23.41, 23.42; 95/82, 86, 87; 96/101, 96/102, 104
See application file for complete search history.

(56) References Cited

U.S. PATENT DOCUMENTS

| 3,069,894 | A | 12/1962 | Claudy |
| 3,070,989 | A | 1/1963 | Dueker et al. |
| 3,119,252 | A | 1/1964 | Nerheim |
| 3,139,755 | A | 7/1964 | Reinecke et al. |

(Continued)

FOREIGN PATENT DOCUMENTS

WO  WO01/71340  9/2001

(Continued)

OTHER PUBLICATIONS

ABB Inc., TotalFlow Model8000/8100 BTU/CV Transmitter user manual, Totalflow Products, Bartlesville, Oklahoma 74006 U.S.A., 2001, 239 pages.

(Continued)

*Primary Examiner*—Daniel S Larkin
(74) *Attorney, Agent, or Firm*—Paul R. Katterle

(57) ABSTRACT

The present invention is directed to a gas chromatograph having a display screen. The gas chromatograph includes an explosion-proof housing and a transparent panel secured to the housing. The display screen is disposed in the housing and is visible through the transparent panel. A gas chromatograph (GC) assembly is disposed in the housing and includes a column for separating components of the gas and a detector for detecting the components of the gas. An electronics assembly is disposed in the housing and includes a microprocessor and memory. A graphical user interface (GUI) software application is stored in the memory and is executable by the microprocessor to display a plurality of windows on the display screen. The windows contain information about the operation of the gas chromatograph.

19 Claims, 44 Drawing Sheets

U.S. PATENT DOCUMENTS

| | | | |
|---|---|---|---|
| 3,374,660 A | | 3/1968 | Mckinney et al. |
| 3,429,176 A | | 2/1969 | Topham |
| 3,748,833 A | * | 7/1973 | Karas et al. .................. 96/105 |
| 3,910,765 A | | 10/1975 | Tinklepaugh et al. |
| 4,006,624 A | * | 2/1977 | Annino et al. ............. 73/23.23 |
| 4,044,593 A | | 8/1977 | Haruki et al. |
| 4,057,755 A | | 11/1977 | Piesche |
| 4,059,994 A | * | 11/1977 | Annino et al. ............. 73/23.35 |
| 4,088,458 A | | 5/1978 | Jourdan |
| 4,735,082 A | | 4/1988 | Kolloff |
| 4,854,952 A | | 8/1989 | Stepien |
| 4,869,282 A | | 9/1989 | Sittler et al. |
| 5,005,399 A | | 4/1991 | Holtzclaw et al. |
| 5,105,652 A | | 4/1992 | Manfredi et al. |
| 5,151,688 A | | 9/1992 | Tanaka et al. |
| 5,231,381 A | | 7/1993 | Duwaer |
| 5,265,459 A | | 11/1993 | Cohen |
| 5,278,543 A | | 1/1994 | Orth et al. |
| 5,285,064 A | | 2/1994 | Willoughby |
| 5,298,225 A | | 3/1994 | Higdon |
| 5,313,061 A | | 5/1994 | Drew et al. |
| 5,340,543 A | | 8/1994 | Annino et al. |
| 5,369,386 A | | 11/1994 | Alden et al. |
| 5,379,630 A | | 1/1995 | Lacey |
| 5,389,951 A | | 2/1995 | Baker |
| 5,461,204 A | | 10/1995 | Makinwa et al. |
| 5,495,769 A | | 3/1996 | Broden et al. |
| 5,544,276 A | | 8/1996 | Loux et al. |
| 5,587,520 A | | 12/1996 | Rhodes |
| 5,587,559 A | | 12/1996 | Fleck et al. |
| 5,663,488 A | | 9/1997 | Wang et al. |
| 5,746,976 A | | 5/1998 | Yamada et al. |
| 5,750,939 A | | 5/1998 | Makinwa et al. |
| 5,756,878 A | | 5/1998 | Muto et al. |
| 5,764,928 A | | 6/1998 | Lanctot |
| 5,796,347 A | | 8/1998 | Zulaski |
| 5,808,179 A | | 9/1998 | Sittler et al. |
| 5,950,674 A | | 9/1999 | Wylie et al. |
| 5,983,703 A | | 11/1999 | Wylie et al. |
| 6,004,514 A | | 12/1999 | Hikosaka et al. |
| 6,028,699 A | | 2/2000 | Fisher |
| 6,029,499 A | | 2/2000 | Sittler et al. |
| 6,062,095 A | | 5/2000 | Mulrooney et al. |
| 6,102,449 A | | 8/2000 | Welsh |
| 6,365,105 B1 | | 4/2002 | Waters et al. |
| 6,374,860 B2 | | 4/2002 | Xu et al. |
| 6,453,725 B1 | | 9/2002 | Dahlgren et al. |
| 6,510,740 B1 | | 1/2003 | Behm et al. |
| 6,568,244 B2 | | 5/2003 | Binz et al. |
| 6,598,460 B2 | | 7/2003 | Muto |
| 6,701,774 B2 | | 3/2004 | Srinivasan et al. |
| 6,718,817 B1 | | 4/2004 | Ko et al. |
| 6,742,544 B2 | | 6/2004 | Bergh et al. |
| 6,761,056 B2 | | 7/2004 | Schram et al. |
| 6,846,458 B1 | * | 1/2005 | Staphanos ................... 422/81 |
| 6,896,238 B2 | | 5/2005 | Wang |
| 6,910,394 B2 | | 6/2005 | Kriel |
| 7,004,191 B2 | | 2/2006 | Shajii et al. |
| 7,063,302 B2 | | 6/2006 | Cordill |
| 7,120,508 B2 | | 10/2006 | Peshkin et al. |
| 7,134,354 B2 | | 11/2006 | Nelson et al. |
| 7,506,533 B2 | | 3/2009 | Bailey et al. |
| 2005/0100479 A1 | | 5/2005 | White et al. |
| 2006/0210441 A1 | | 9/2006 | Schmidt et al. |
| 2007/0089484 A1 | | 4/2007 | Bailey et al. |
| 2007/0204673 A1 | | 9/2007 | Bailey et al. |
| 2008/0052013 A1 | | 2/2008 | Bailey et al. |
| 2008/0072976 A1 | | 3/2008 | Bailey et al. |
| 2008/0087072 A1 | | 4/2008 | Asher et al. |
| 2008/0092627 A1 | | 4/2008 | Hadley et al. |

FOREIGN PATENT DOCUMENTS

| | | |
|---|---|---|
| WO | WO01/71340 A1 | 9/2001 |
| WO | WO2007028130 A3 | 11/2006 |
| WO | WO2007/028130 | 3/2007 |

OTHER PUBLICATIONS

Emerson Process Management, Danalyzer 700 Product Data Sheet, DAN-GC700-DS-1005, Oct. 2005, 12 pages.

Emerson Process Management, Danalyzer 700 Product Data Sheet, DAN-GC-DS-53-0803, Aug. 2003, 2 pages.

* cited by examiner

SECTION A-A

SECTION B-B

SECTION C-C

SECTION D-D

COMPACT FIELD-MOUNTABLE GAS CHROMATOGRAPH WITH A DISPLAY SCREEN

CROSS-REFERENCE TO RELATED APPLICATION

This application claims the benefit of U.S. provisional patent application No. 60/713,986 filed on Sep. 2, 2005, which is hereby incorporated by reference in its entirety.

BACKGROUND OF THE INVENTION

The present invention is directed toward gas chromatographs and, more particularly, toward field-mountable gas chromatographs.

Chromatography is the separation of a mixture of compounds (solutes) into separate components. This separation permits the composition of all or part of the mixture to be determined. In gas chromatography, a gas chromatograph (commonly called a "GC") is utilized to separate and determine the quantities of components of a gas mixture. A gas chromatograph performs these functions by taking a sample of the gas mixture to be analyzed and injecting it into a carrier gas stream, such as helium or hydrogen, which then carries the gas sample through one or more tubes (referred to as columns) that are packed with a very fine particulate material. Each of the particles of this material are coated with a film from liquid that controls the rate at which the different components of the gas sample are absorbed and de-absorbed by the particulate material. This rate of absorption and de-absorption also varies relative to each of the different components. Because of this differing rate of absorption and de-absorption, certain gas molecules related to one type or component of gas will exit the column more quickly than some of the other components will. This process of separation of components permits a detector located at the end of the column to quantify the amount of a particular component that is present in the mixture.

Conventional field-mountable gas chromatographs are fairly large and complex devices. The size and complexity of conventional field-mountable gas chromatographs make them difficult to install, operate and service. In addition, a typical field-mountable gas chromatograph does not have an integrated display that permits an operator to view the operation of the gas chromatograph. If a conventional field-mountable gas chromatograph is provided with a display, the display is typically mounted in a housing separate from the housing for the columns and other components of the gas chromatograph.

U.S. Pat. No. 6,004,514 to Hikosa, et al. discloses a field-mountable gas chromatograph having an integrated display. The gas chromatograph of the Hikosa et al. patent, however, is a large, complex system having multiple housings.

Based on the foregoing, there is a need in the art for a more compact and user-friendly field-mountable gas chromatograph having a display. The present invention is directed to such a field-mountable gas chromatograph.

SUMMARY OF THE INVENTION

In accordance with the present invention, a gas chromatograph for analyzing gas is provided and includes an explosion-proof housing defining a single enclosed volume. A display screen is disposed in the single enclosed volume of the housing and is visible from the exterior of the housing. A gas chromatograph (GC) assembly is also disposed in the single enclosed volume of the housing and includes a separation device operable to separate components of the gas and a detector for detecting the components of the gas. A sample selection valve is connected to the separation device and is disposed in the single enclosed volume of the housing.

Also in accordance with the present invention, a gas chromatograph for analyzing gas is provided and includes an explosion-proof housing. A display screen is disposed in the housing and is visible from the exterior of the housing. A gas chromatograph (GC) assembly is disposed in the housing and includes a separation device operable to separate components of the gas and a detector for detecting the components of the gas. An electronics assembly is also disposed in the housing and includes a microprocessor, memory and a graphical user interface (GUI) software application stored in the memory and executable by the microprocessor to display a plurality of windows on the display screen. The windows contain information about the operation of the gas chromatograph.

Also provided in accordance with the present invention is a gas chromatograph having an elongated housing with opposing first and second ends and a longitudinal axis extending through the first and second ends. A display screen is disposed in the housing and is visible from the exterior of the housing. A gas chromatograph (GC) assembly is disposed in the housing and includes at least one column for separating components of the gas and a detector for detecting the components of the gas. The at least one column is wound into a coil through which the longitudinal axis of the housing extends.

Another gas chromatograph provided in accordance with the present invention includes a housing having a body with an opening formed therein. A cover is disposed over the opening and is removably fastened to the body. A transparent panel is fastened to the housing. A display screen is disposed in the housing and is visible through the transparent panel. A gas chromatograph (GC) assembly is disposed in the housing and includes at least one column for separating components of the gas and a detector for detecting the components of the gas. At least a portion of the at least one column extends beyond the plane of the opening in the body so as to be disposed in the cover.

Another gas chromatograph provided in accordance with the present invention is adapted for mounting to a stanchion having a longitudinal axis. The gas chromatograph includes an elongated housing having first and second ends and a longitudinal axis extending through the first and second ends. The housing includes a body and a mount for mounting the gas chromatograph to the stanchion. The mount extends from the body and is located between the first and second ends. The mount is adapted for attachment to the stanchion, whereby when the stanchion is attached to the mount, the longitudinal axis of the housing is disposed perpendicular to the longitudinal axis of the stanchion. A display screen is disposed in the housing and is visible from the exterior of the housing. Also disposed in the housing is a gas chromatograph (GC) assembly having a separation device operable to separate components of the gas, and a detector for detecting the components of the gas.

Still another gas chromatograph provided in accordance with the present invention includes a substantially cylindrical housing. A transparent panel is fastened to the housing. A display screen is disposed in the housing and is visible through the transparent panel. A gas chromatograph (GC) assembly is disposed in the housing and includes at least one column for separating components of the gas, and a detector for detecting the components of the gas.

BRIEF DESCRIPTION OF THE DRAWINGS

The features, aspects, and advantages of the present invention will become better understood with regard to the following description, appended claims, and accompanying drawings where:

DETAILED DESCRIPTION OF ILLUSTRATIVE EMBODIMENTS

Figure 1:
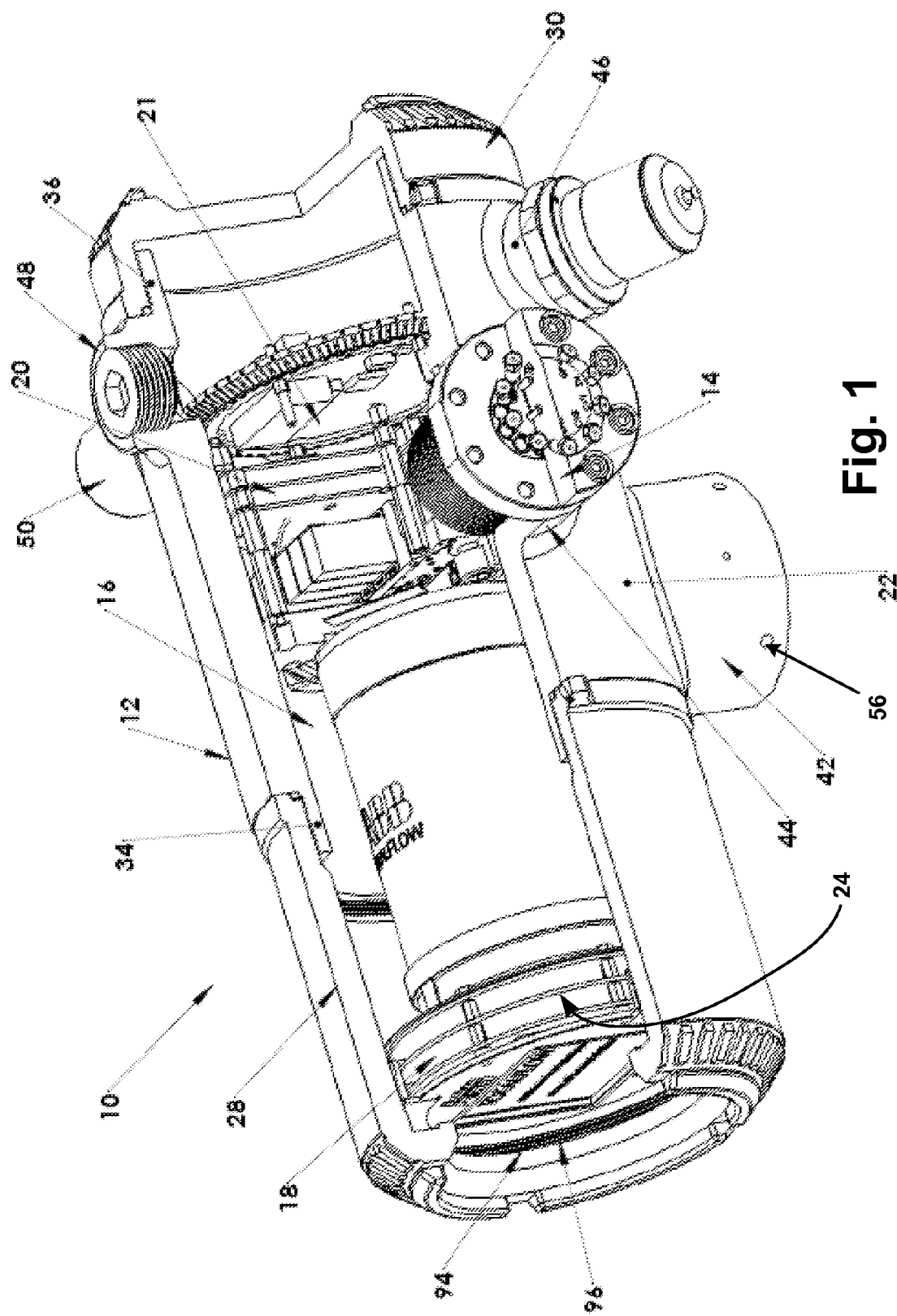
FIG. 1 shows a perspective view of a gas chromatograph with a portion cut away to better show the interior features thereof.

It should be noted that in the detailed description that follows, identical components have the same reference numerals, regardless of whether they are shown in different embodiments of the present invention. It should also be noted that in order to clearly and concisely disclose the present invention, the drawings may not necessarily be to scale and certain features of the invention may be shown in somewhat schematic form.

Below is a list of acronyms used in the specification and their respective meanings:

"CPU" shall mean "central processing unit";
"DSP" shall mean "digital signal processor";
"GC" shall mean "gas chromatography";

"MMU" shall mean "memory management unit";
"PCA" shall mean "printed circuit assembly";
"PCB" shall mean "printed circuit board";
"RISC" shall mean "reduced instruction set computing";
"CD" shall mean "thermal conductivity sensor"; and
"USART" shall mean a "multi-channel universal serial asynchronous receiver transmitter".

As used herein, the term "printed circuit board" (or PCB) shall mean a thin plate to which electronic components may be mounted and which has conductive pathways or traces disposed on a non-conductive substrate. The term "printed circuit board" (or PCB) shall include circuit boards that are rigid and circuit boards that are flexible or slightly flexible, i.e., flex circuits or rigid-flex circuits.

The present invention is directed to a gas chromatograph 10 having a compact and modular configuration, as well as improved operational features. The gas chromatograph 10 is adapted for mounting in the field, proximate to a source of gas that is desired to be analyzed, such as natural gas. The gas chromatograph 10 is adapted for use in harsh and explosive environments. More specifically, the gas chromatograph 10 is explosion-proof and has a NEMA 4X rating. Referring now to FIG. 1, the gas chromatograph 10 generally comprises a housing 12 enclosing a feed-through module 14, an analytical module 16, a main electronics assembly 18 having a main CPU 24, an analytical processor assembly 20 and a termination assembly 21.

I. Housing

As used herein with regard to components of the housing 12, relative positional terms such as "front", "rear", etc. refer to the position of the component in the context of the position of the gas chromatograph 10 in FIG. 1. Such relative positional terms are used only to facilitate description and are not meant to be limiting.

Figure 2:
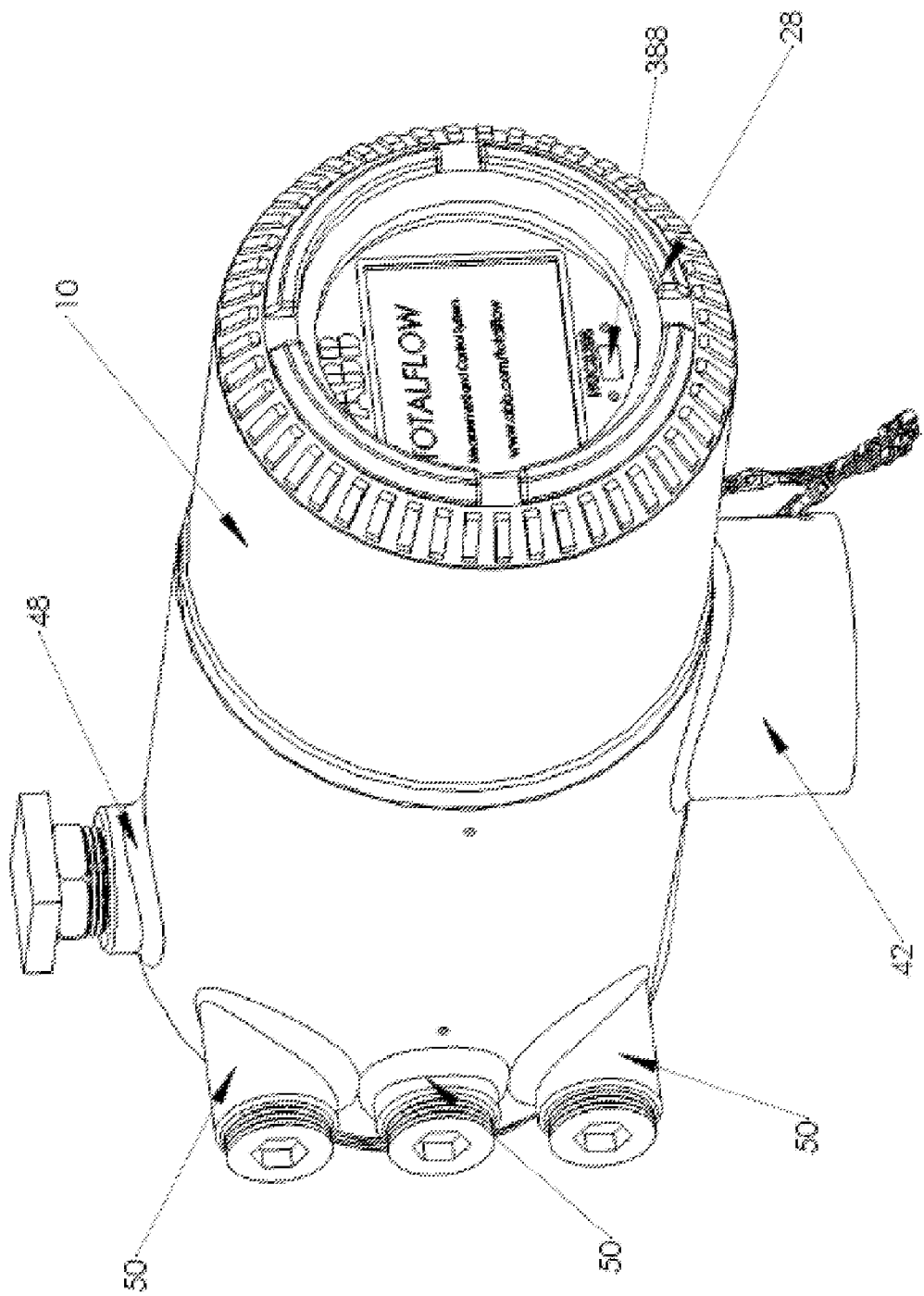
FIG. 2 shows a front perspective view of the gas chromatograph.
Figure 3:
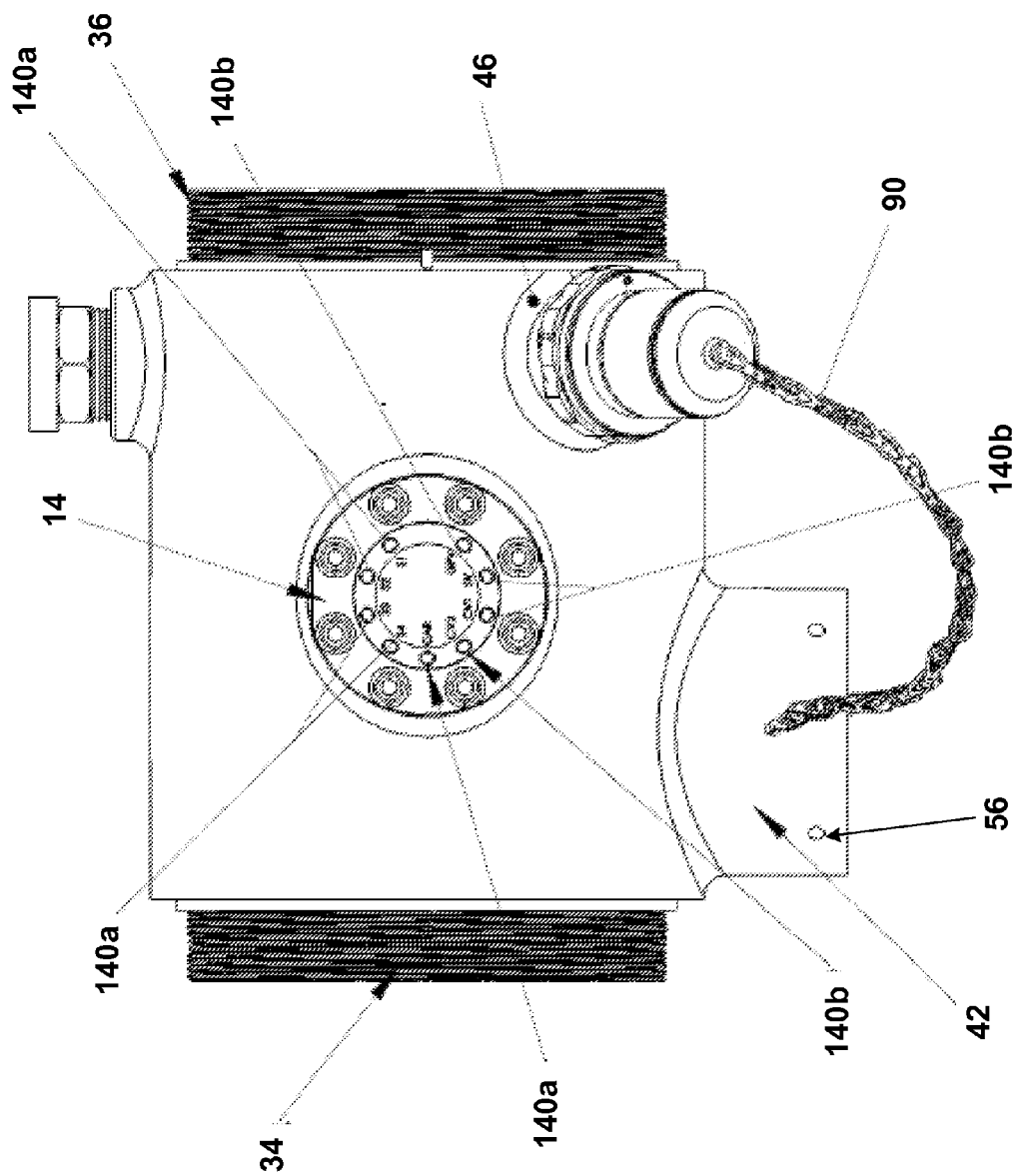
FIG. 3 shows a side view of a portion of a housing of the gas chromatograph.
Figure 4:
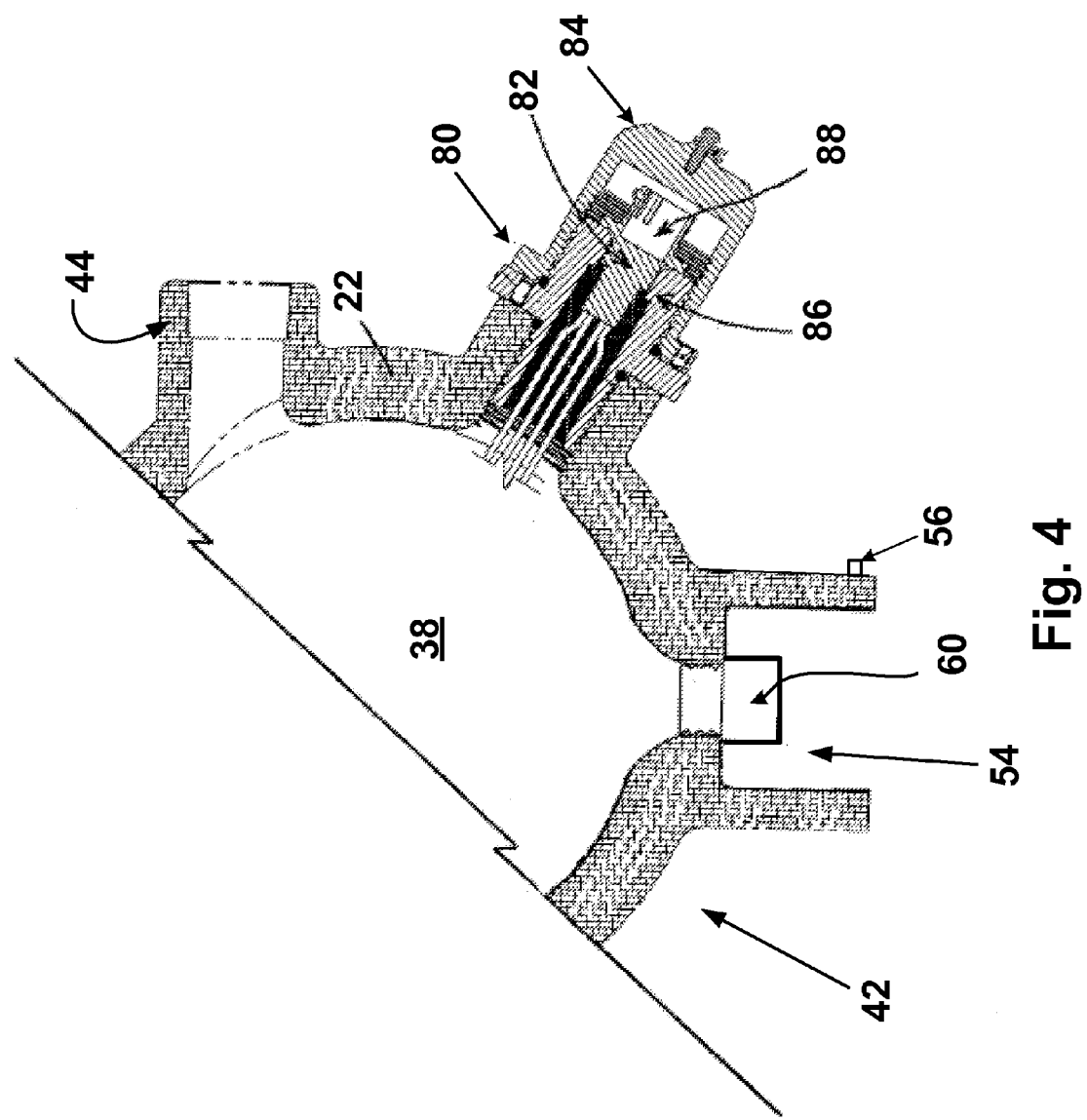
FIG. 4 shows a sectional view of a portion of the gas chromatograph showing a main mount and a first communication boss with a connector assembly mounted thereto.

Referring now also to FIGS. 2-4, the housing 12 includes a cylindrical main section 22 having front and rear access openings closed by removable front and rear access covers 28, 30, respectively. The main section 22 has a unitary construction and is comprised of a cast metal, such as aluminum or steel. The main section 22 has threaded front and rear collars 34, 36 that define the front and rear access openings, respectively. An interior surface of the main section 22 defines an interior cavity 38. A plurality of mounting ears 40 (shown in FIG. 33) are joined to the interior surface of the main section 22, around the circumference thereof and extend inwardly into the interior cavity 38. A main mount 42, a feed boss 44, first and second communication bosses 46, 48 and one or more conduit bosses 50 are joined to the main section 22 and extend outwardly therefrom.

With particular reference now to FIG. 4, the main mount 42 is cylindrical and extends vertically downward from the bottom of the central portion of the main section 22. An interior surface of the mount defines a cylindrical cavity 54 for receiving a pipe or other structure for supporting the gas chromatograph. A grounding lug 56 is attached to the exterior of the mount for electrical connection to a wire or cable electrically connected to an earth ground. A threaded breather passage extends through the main section 22 and into the interior cavity 38 of the housing 12. A breather/drain valve 60 is threaded into the breather passage. In this manner, when the gas chromatograph 10 is mounted to a pipe, the breather/drain valve 60 is disposed inside the pipe and, thus, is shielded from the outside environment.

Figure 5:
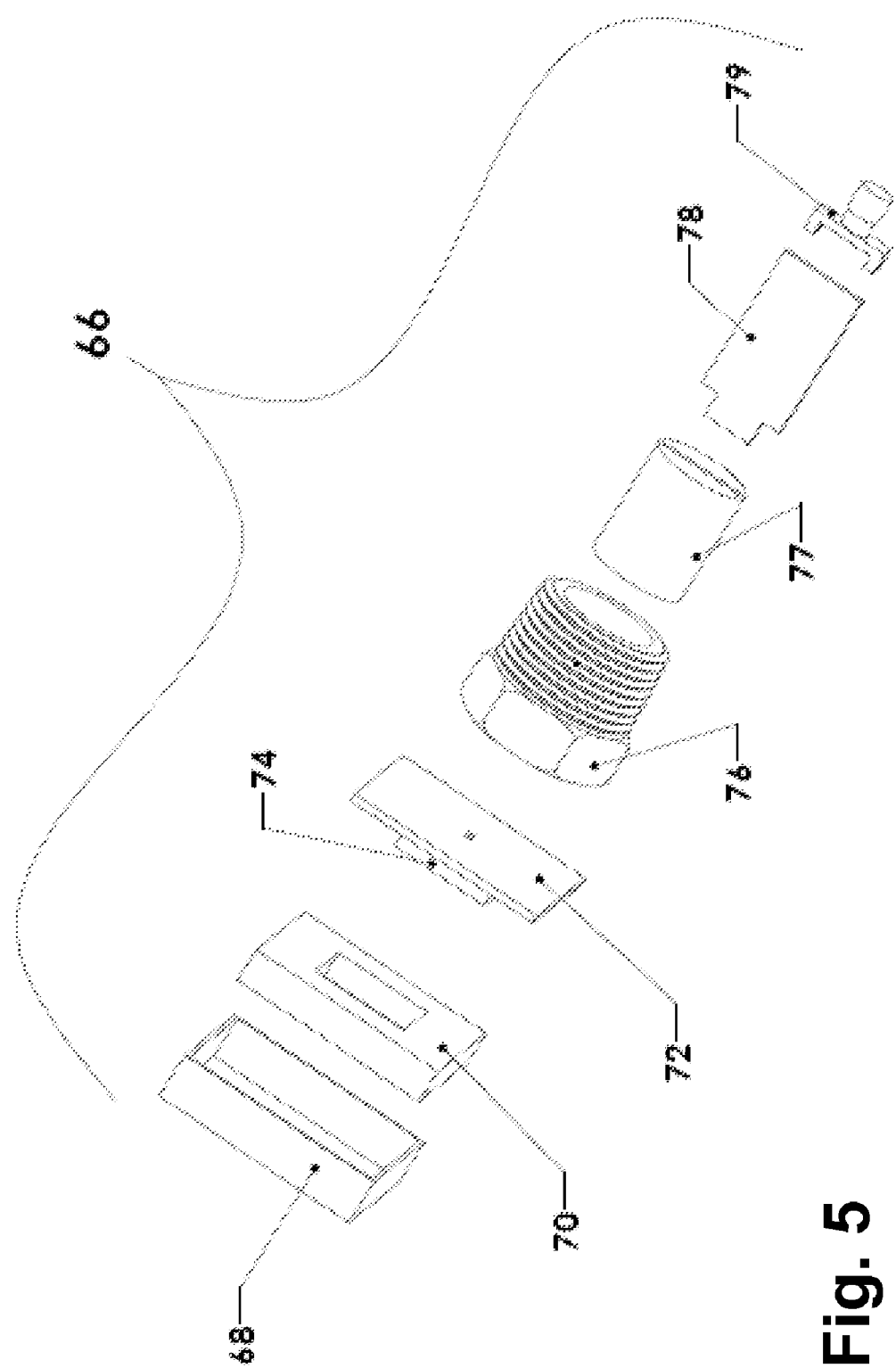
FIG. 5 shows an exploded view of an antenna module of the gas chromatograph.

The second communication boss 48 is cylindrical and extends upward from a top portion of the main section 22. An interior surface of the second communication boss 48 helps defines an interior passage that extends through the main section 22 and into the interior cavity 38 of the housing 12. The interior surface has an interior thread that secures an antenna module 66 (shown in FIGS. 5 and 33) to the second communication boss 48. The antenna module 66 is capable of transmitting and receiving radio frequency (RF) energy. Although the antenna module 66 is mounted outside the housing 12, the antenna module 66 does not have a typical "aerial type" construction wherein the antenna extends into the air with a single electrically conducting element comprised of a flexible wire or rigid or semi-rigid metal conductor, commonly referred to as a whip antenna. Referring now to FIG. 5, the antenna module 66 includes an NPT plug 76 having a body with an exterior thread adapted to mate with the interior thread of the second communication boss 48. An antenna 74 secured to a plastic plate 72 is secured to the plug 76, such as by an over-molding process. The antenna 74 may be a microstrip antenna, a planar inverted "F" antenna (PIFA), or a meander line antenna. A microstrip antenna is constructed using printed circuit board fabrication techniques. One type of microstrip antenna is a patch antenna that comprises in stacked relation, a ground plane, a dielectric substrate and a metallic antenna element. A meanderline antenna is a slow wave structure that decouples the conventional relationship between the antenna physical length and the resonant frequency based on the free-space wavelength. A meanderline antenna typically includes a loop antenna and one or more frequency-tuning meander lines. A meander line is a conductive path having a series of parallel elements forming a serpentine configuration. A typical meanderline antenna includes two vertical conductors extending from a ground plane and a horizontal conductor spaced above the ground plane and extending between the vertical conductors. The vertical conductors are connected to the horizontal conductor by two meanderline couplers, respectively. The meanderline couplers may have controllably adjustable lengths for changing the characteristics of the antenna. Examples of meanderline antennas which may be used for the antenna 74 are disclosed in U.S. Pat. Nos. 5,790,080 and 6,741,212, which are hereby incorporated by reference. A commercial example of a meanderline antenna, which may be used for the antenna 74 is a 5.8 GHz WLAN antenna available from SkyCross. The antenna 74 is connected by a multilayer printed circuit board 78 to a PCB mount RF connector 79, which is connected to the termination assembly 21. The printed circuit board 78 extends through the plug 76. A potting compound 77 may be disposed around the printed circuit board 78 inside the plug 76. A plastic cover 68 is secured to the plate 72 over the antenna 74. The cover 68 may be filled with a potting compound 70.

Referring back to FIG. 4, the first communication boss 46 is cylindrical and extends obliquely downward from a bottom portion of the main section 22. An interior surface of the first communication boss 46 helps defines a passage that extends through the main section 22 and into the interior cavity 38 of the housing 12. The interior surface has an interior thread for securing a connector assembly 80 to the first communication boss 46.

The connector assembly 80 includes a connector 82, a cap 84 and a mount 86. The connector 82 has a communication port 88 joined at an annular flange to a body with an exterior thread. The communication port 88 is a Universal Serial Bus (USB) port. Alternately, the communication port 88 may be an RS-232 or RS-485 port. The communication port 88 is connected to the termination assembly 21 by wiring. The cap 84 is cylindrical and has an annular flange disposed around a lower opening. An interior surface of the cap 84 includes an interior thread. The cap 84 may be connected to the main mount 42 by a chain 90 to prevent misplacement of the cap 84 after removal, as shown in FIG. 3. The mount 86 has an inner portion joined to an outer portion by an annular flange. The inner portion includes an exterior thread for mating with the interior thread of the first communication port 46 so as to removably secure the mount 86 to the first communication port 46. The outer portion has an interior thread for mating with the exterior thread of the connector 82 so as to removably secure the connector 82 to the mount 86. In addition, the outer portion has an exterior thread for mating with the interior thread of the cap 84 so as to removably secure the cap 84 to the mount 86. When the connector 82 is secured to the mount 86, the flange of the connector 82 abuts an end surface of the outer portion of the mount 86, and when the cap 84 is secured to the mount 86, the connector 82 is disposed inside the cap 84 and the flange of the cap 84 abuts the annular flange of the mount 86.

Referring back to FIG. 1, the rear access cover 30 is cylindrical and has anterior and posterior ends. The anterior end has an interior thread for mating with the exterior thread of the rear collar 36 so as to removably secure the rear access cover 30 to the main section 22 and close the rear access opening. The posterior end has a plurality of spaced-apart and circumferentially disposed ribs. The ribs help an operator establish a grip on the rear access cover 30 when rotating the rear access cover 30 to open or close the rear access opening.

The front access cover 28 is cylindrical and has anterior and posterior ends. The posterior end has an interior thread for mating with the exterior thread of the front collar 34 so as to removably secure the front access cover 28 to the main section 22 and close the front access opening. The anterior end has a plurality of spaced-apart ribs circumferentially disposed around a view opening 94. The ribs help an operator establish a grip on the front access cover 28 when rotating the front access cover 28 to open or close the front access opening. The view opening 94 is closed by a transparent shield panel 96 that provides shielding against radio frequency interference (RFI).

The conduit bosses 50 have threaded openings for securing conduits to the housing 12. Interior passages extend through the conduit bosses 50 and into the interior cavity 38. When the gas chromatograph 10 is mounted in the field, first and second conduits may be secured to first and second conduit bosses 50, wherein the first conduit runs power wiring into the interior cavity 38 and the second conduit runs a communication line, such as an Ethernet cable, into the interior cavity 38. If a conduit boss 50 is not connected to a conduit, the conduit boss 50 is closed with an NPT plug.

When the gas chromatograph 10 is mounted and operating in the field unattended, the housing 12 is closed, i.e., the front and rear access covers 28, 30 are secured to the main section 22, the feed-through module 14 is secured to the feed boss 44, the conduit bosses 50 are connected to conduits or closed with NPT plugs, the second communication boss 48 is connected to the antenna module 66 or closed with an NPT plug, and the first communication boss 46 is connected to the connector assembly 80, with the cap 84 secured to the mount 86. When the housing 12 is closed as described above, the housing 12 is explosion-proof (and flame-proof) and defines a single contained volume. As used herein, the term "contained volume" shall mean that if an explosion occurs in the contained volume, the explosion will not propagate to the environment external to the contained volume. More specifically, if an explosion occurs in the contained volume, gases escaping the contained volume through any gaps or openings in the housing 12 will not be hot enough to ignite a classified hazardous location (or potentially explosive atmosphere) external to the contained volume. Specifications for certifying an enclosure as being explosion proof or flame proof are provided by certifying agencies, such as the Factory Mutual Research Corporation (FM), the Canadian Standards Association (CSA), the International Electrotechnical Commission (IEC) and the Committee for Electrotechnical Standardization (CENELEC).

Figure 6:
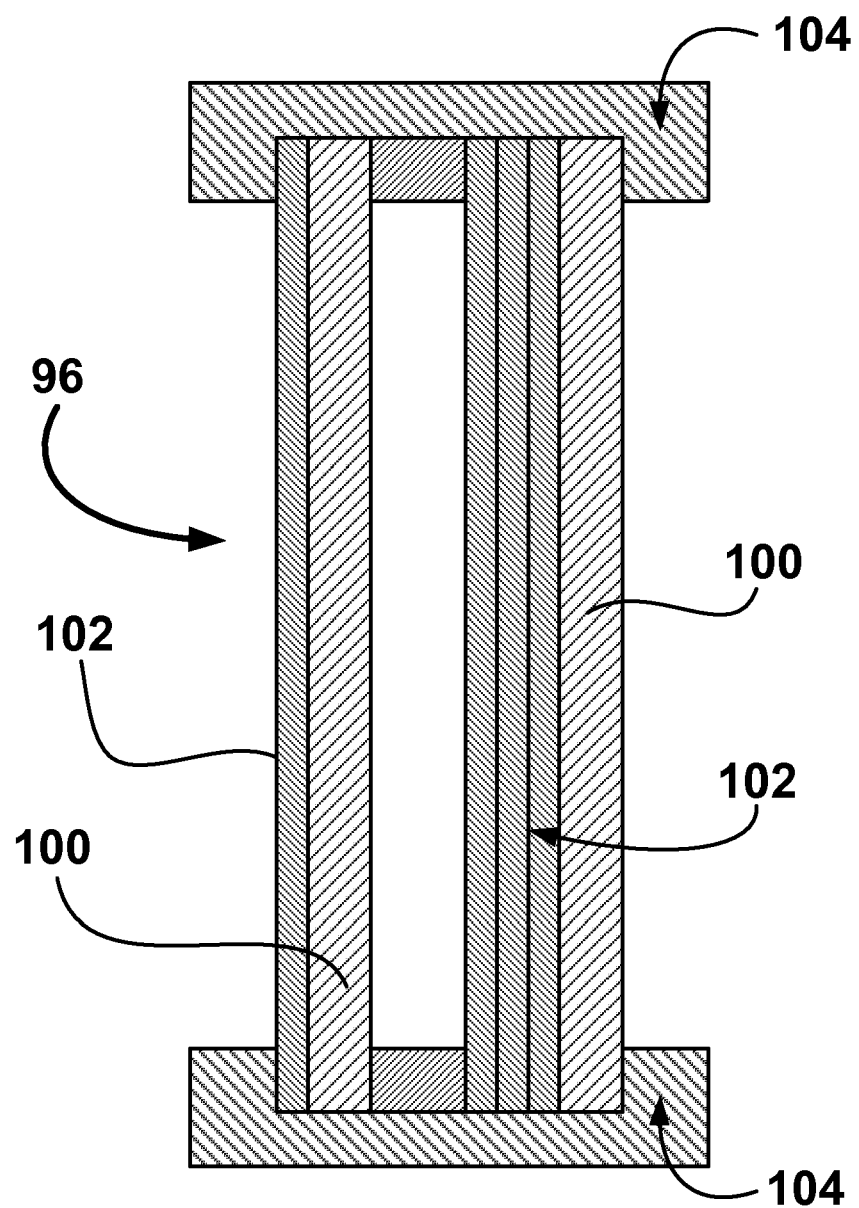
FIG. 6 shows a sectional view of a shield panel of the gas chromatograph.

Referring now to FIG. 6, the shield panel 96 includes one or more transparent sheets 100 adjoining one or more transparent conductive layers 102. The transparent sheet 100 may be comprised of glass or plastic, and the layers 102 may be comprised of wire mesh and/or coatings. For example, in one embodiment, the shield panel 96 may comprise a wire mesh sandwiched between a pair of sheets of glass or transparent plastic. The wire mesh is comprised of a metal such as stainless steel and may be coated with one or more layers of one or more other metals, such as nickel, copper, silver, gold, aluminum, chrome, or titanium, or alloys thereof. The wire mesh may have a wire diameter between about 0.0005 to about 0.010 inch and an open area (relative to the total mesh area) between about 40% to about 75%. Examples of shield panels with wire mesh which may be used for the shield panel are disclosed in U.S. Pat. Nos. 4,247,737; 4,826,718; and 5,012,041, all of which are hereby incorporated by reference.

In other embodiments, the shield panel 96 comprises at least one sheet of glass or transparent plastic coated with at least one transparent conductive coating. Typically, each conductive coating has a thickness in a range between about 5 and about 300 nm and may be comprised of a single layer of a conductive metal, such as nickel, copper, silver, gold, aluminum, chrome, or titanium, or alloys thereof, or may be comprised of one or more layers of such a conductive metal along with one or more layers of a metal oxide, such as tin oxide, indium oxide, titanium oxide, zinc oxide, or bismuth oxide. The conductive metal layer may be directly deposited on the glass or plastic sheet and overlaid with an oxide layer, or the conductive metal layer may be sandwiched between a pair of metal oxide layers. In one embodiment, a pair of conductive metal coatings are formed on opposing major surfaces of a single sheet of glass. In another embodiment, one such conductive metal coating is deposited on a major surface of a first glass sheet and a semiconductive coating of a metal oxide, such as tin doped indium oxide (ITO) or doped tin oxide is deposited on a major surface of a second glass sheet, wherein the conductive metal coating is positioned between the two glass sheets and the semiconductive coating is positioned on the exterior of the shield panel. A conductive metal layer is typically deposited on a glass or plastic sheet by sputtering in an inert gas, such as argon, while a metal oxide layer is typically deposited on a glass or plastic sheet by reactive sputtering in an atmosphere containing an inert gas and a controlled amount of oxygen. Examples of shield panels with a conductive coating which may be used for the shield panel 96 are disclosed in U.S. Pat. Nos. 4,978,812; 5,147,694; and 5,358,787, all of which are hereby incorporated by reference.

As measured in decibels (dB) of attenuation, some embodiments of the shield panel 96 provide at least 30 dB of attenuation for frequencies in a range between 1 and 10,000 MHz. In other embodiments, the shield panel 96 provides at least 40 dB of attenuation for frequencies in a range between 1 and 10,000 MHz. In smaller frequency ranges, such as in a range between 1 and 1,000 MHz, some embodiments of the shield panel 96 provide at least 50 dB of attenuation. At a frequency of about 1,000 MHz, some embodiments of the shield panel 96 provide more than 60 dB of attenuation. It should be noted that 40 dB corresponds to an attenuation of about 99% and 60 dB corresponds to an attenuation of about 99.9%.

Although the shield panel 96 substantially blocks the transmission of electromagnetic waves having lower frequencies and longer wavelengths (such as radio, television and cell phone signals), the shield panel 96 substantially permits the transmission of electromagnetic waves having higher frequencies and shorter wavelengths (such as visible and near infrared light waves). Thus, the shield panel 96 has a visible light transmission of at least 50%. Some embodiments of the shield panel 96 have a visible light transmission of at least 60% and still other embodiments of the shield panel 96 have a visible light transmission of at least 70%.

In order to provide a direct electrical connection between the shield panel 96 and the housing 12, a conductive gasket 104 may be disposed around the view opening 94, between the shield panel 96 and the front access cover 28. The gasket 104 is compressible and may be comprised of metal-loaded rubber. The shield panel 96 may be held in place and compressed against the gasket 104 by clasps, or other types of fasteners.

II. Feed-Through Module

Referring now to FIGS. 1, 3 and 7-10, the feed-through module 14 is removably secured to the feed boss 44 of the housing 12 by a threaded connection. When so secured, the longitudinal axis of the feed-through module 14 is disposed perpendicular to the longitudinal axes of the housing 12 and the analytical module 16. The feed-through module 14 generally comprises a connection structure 110 and a feed plate 112. The feed plate 112 is removably secured to the connection structure 110.

The connection structure 110 is composed of a metal, such as aluminum, and includes a body 114 joined between a base 116 and a head 118. The base 116 is generally rectangular and has a first major face 120 with an enlarged groove 122 formed therein and an opposing second major face 124. An enlarged threaded bore 126 extends through the second major face 124 into the base 116. A plurality of inner passage openings 128 are formed in the second major face 124 and are circumferentially disposed around the bore 126. An annular gasket 123 is secured to the second major face 124 and has holes formed therein, which are aligned with the inner passage openings 128. A pair of guide posts 130 are secured to the base 116 on opposing sides of the bore 126 and extend outwardly from the second major face 124, through the gasket. The body 114 has a cylindrical portion with an exterior thread for mating with the interior thread of the feed boss 44 so as to secure the feed-through module 14 to the housing 12. A shoulder is disposed proximate to an outermost turn of the exterior thread and is provided with an O-ring 134 for forming a seal between the feed boss 44 and the feed-through module 14. A plurality of threaded mounting openings 136 are disposed around the circumference of the head 118.

Figure 44:
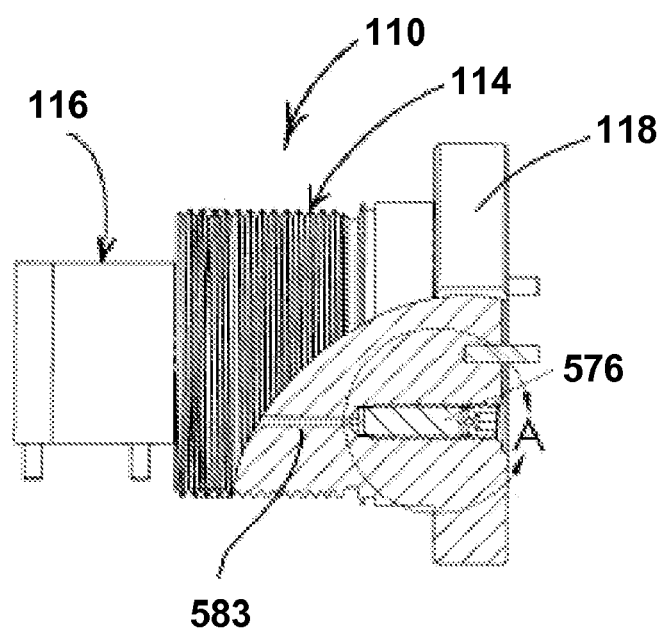
FIG. 44 shows a side view of the connection structure of the feed-through module with a portion cut away to provide a sectional view.
Figure 45:
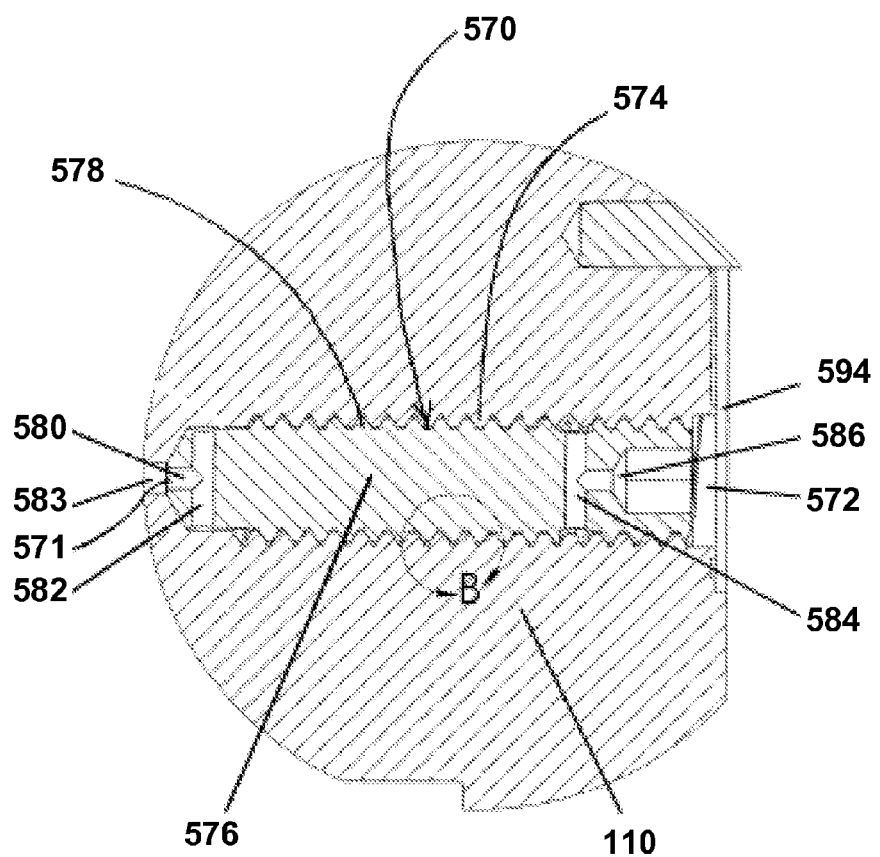
FIG. 45 shows an enlarged portion of the sectional view of the connection structure identified by the circle "A" in FIG. 44.
Figure 46:
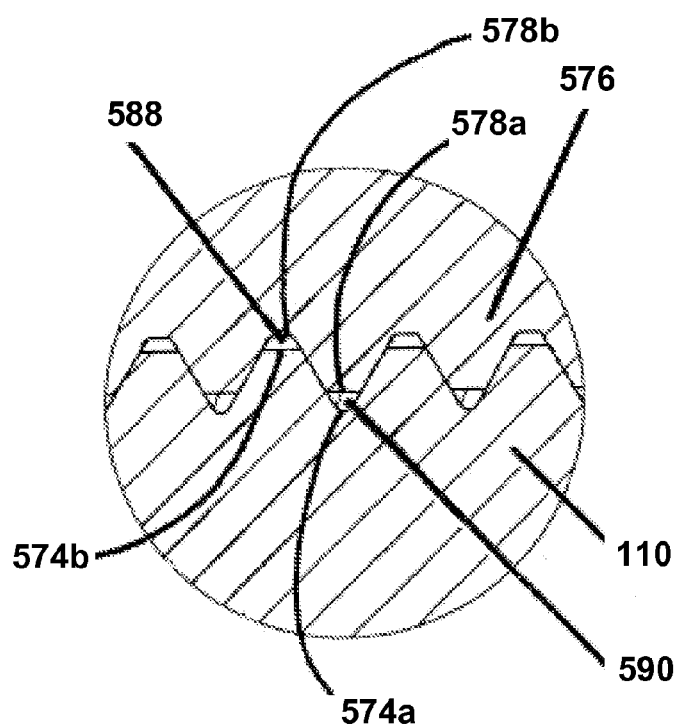
FIG. 46 shows an enlarged portion of the sectional view of the connection structure identified by the circle "B" in FIG. 45.

Referring now to FIGS. 44, 45 and 46, a plurality of flow chambers 570 are formed in the connection structure 110 and are disposed in a circular configuration. Each flow chamber 570 comprises an inner opening 571, an outer opening 572 and a middle portion defined by a helical thread 574 formed in the connection structure 110. The outer openings 572 are formed in an outer surface of the head 118, radially inward from the mounting openings 136. The minor thread diameter 574b of the helical thread 574 is flattened. A solid metal insert 576 is disposed in each flow chamber 570. Each insert 576 comprises an inner portion having a smooth exterior surface and an outer portion having an exterior surface with a helical thread 578 formed therein. The major thread diameter 578a of each helical thread 578 is flattened. In the inner portion of each insert 576, a longitudinal passage 580 extends through an inner end of the insert 576 and intersects an inner transverse passage 582 extending through the insert 576. The longitudinal passages 580 are connected to flow paths 583 extending through the connection structure 110 to the inner passage openings 128 in the base 116. In the helical portion of each insert 576, the helical thread 578 is interrupted by a band of smooth exterior surface. An outer transverse passage 584 extends through each insert 576 in the band of smooth exterior surface. In each insert 576, a longitudinal passage 585 intersects the outer transverse passage 584 and opens into an enlarged bore 586 formed in an outer end of the insert 576. The outer end of each insert 576 is recessed into its corresponding flow chamber 570 so as to form an interior annular ledge proximate to the outer opening 572.

In each flow chamber 570 and insert 576 combination, the flattened minor thread diameter 574b of the connection structure 110 cooperates with the minor thread diameter 578b of the insert 576 to form an inner flow passage 588, while the major thread diameter 574a of the connection structure 110 cooperates with the flattened major thread diameter 578a of the insert 576 to define an outer flow passage 590. The outer flow passage 590 is disposed radially outward from the inner flow passage 588. Both the outer flow passage 590 and the inner flow passage 588 extend between and are connected to the inner and outer transverse passages 582, 584. Thus, for each flow chamber 570 and insert 576 combination, a sample gas stream from a flow path 583 enters the longitudinal passage 580, travels to the inner transverse passage 582 and splits into two streams that travel through the inner and outer flow passages 588, 590 respectively. The two streams recombine in the outer transverse passage 584, travel through the longitudinal passage 585 to the enlarged bore 586 and exit the flow chamber 570 through the outer opening 572. Of course, vented gas entering an outer opening 572 travels the same path, but in the opposite direction.

It should be appreciated that each flow chamber 570 and insert 576 combination provides two flame paths, namely the inner and outer flow passages 588, 590. These two flame paths provide twice the cross-sectional area of a conventional flame path, i.e., a 10 mil ID tube. In addition, the two flame paths provide a significantly larger flow surface area than a conventional flame path. This increased surface area results in greater cooling of escaping gases (in the event of an internal explosion), thereby providing a wider safety margin on flame suppression.

The outer openings 572 of the flow chambers 570 are located in a disc-shaped depression 594 formed in the head 118. A single disc-shaped gasket 144 (shown in FIG. 9) is secured in the depression 594 and has openings aligned with the outer openings 572. Disc-shaped filters 146 (shown in FIG. 9) are disposed in those outer openings 572 that function as sample gas inputs. Those outer openings 572 that function as vent outputs are not provided with filters. The filters 146 are supported on the ledges formed by the outer ends of the inserts 576. The filters 146 may be secured in place by the gasket 144. The filters 146 are comprised of sintered stainless steel with 0.5 to 10 micron openings.

The feed plate 112 is composed of a metal, such as stainless steel, and is cylindrical, with inner and outer end surfaces. A plurality of threaded mounting openings 138 are circumferentially disposed around the feed plate 112 and extend therethrough. A plurality of threaded openings 140 (shown in FIG. 3) extend through the feed plate 112 at oblique angles to the central axis of the feed plate 112. The openings 140 are arranged in a circular configuration and are disposed radially inward from the mounting openings 138. For each opening 140, an indelible marking identifying the opening is made in the outer end surface, proximate to the opening 140. By way of example, the openings 140a may be sample inputs 1-4 marked S1, S2, S3, S4, respectively, and a carrier gas input marked CAR; and the openings 140b may be column vents 1, 2, marked CV1, CV2, respectively, a sample vent marked SOV, and a gauge port vent marked GPV. The markings may be made by photo, electrochemical, or laser etching. Fitting assemblies 142 are secured in the openings 140, respectively, for connecting tubes to the openings 140, respectively. Each fitting assembly 142 may be a compression fitting comprising a male nut and a ferrule. The male nuts are threadably secured in the openings 140 and extend outwardly therefrom, while the ferrules are disposed in the openings 140 and are compressed by the male nuts. The ends of the tubes extend through the male nuts and the ferrules and are held in place in the openings 140 by the compression of the ferrules. Since the openings 140 are disposed at oblique angles, the fitting assemblies 142 extend obliquely outward from the feed plate 112, which provides more space for accessing the fitting assemblies 142 manually or with tools.

The mounting openings 138 in the feed plate 112 align with the openings 136 in the head 118 so that the feed plate 112 can be secured to the connection structure 110 by threadably disposing screws 148 in the aligned mounting openings 136, 138. When the feed plate 112 is secured to the connection structure 110, the openings 140 align with the outer openings 572 in the connection structure 110, respectively, thereby forming inlet paths and vent paths that extend through the feed-through module 14 between the inner passage openings 128 in the base 116 and the openings 140 in the feed plate 112. More specifically, the inlet paths include sample stream paths 1-4 and a carrier gas path, and the vent paths include a sample vent path and a gauge port vent path. The gasket 144 seals the interface between the feed plate 112 and the connection structure 110 around the openings 140.

The feed-through module 14 includes an inlet heating assembly comprising a cartridge heater 150, a temperature sensor 152 and a thermal switch or breaker 154. The cartridge heater 150 is secured within a tunnel that extends longitudinally into the body 114 of the connection structure 110 and has an opening disposed proximate to the groove 122 of the base 116. The temperature sensor 152 is disposed in a well formed in the body 114 of the connection structure 110, proximate to the cartridge heater 150. The thermal breaker 154 is secured within the groove 122 of the base 116. The inlet heating assembly is connected to an analytical PCA 160 of the analytical processor assembly 20. The analytical PCA 160 controls the operation of the cartridge heater 150 based on the temperature sensed by the temperature sensor 152. If the temperature of the base 116 exceeds a maximum temperature, the thermal breaker 154 opens and cuts off power to the cartridge heater 150. When the temperature of the base 116 decreases to a lower reset temperature, the thermal breaker 154 automatically closes and provides power to the cartridge heater 150.

The construction of the feed-through module 14 provides a number of benefits. The provision of a separate removable feed plate 112 permits the gas chromatograph 10 to utilize different sample interfaces. More specifically, the feed plate 112 can be removed and replaced with another type of feed plate that may be more appropriate or desired for a particular installation of the gas chromatograph 10. For example, if it is desired to use vent tubes and inlet tubes with O-ring connections, a first alternate feed plate (not shown) with O-ring fittings may be used in lieu of the feed plate 112. Also, if a sample conditioning system is desired and is not provided, a second alternate feed plate with a sample conditioning system mounted thereto may be used in lieu of the feed plate 112 (or the first alternate feed plate). The removal of the feed plate 112 and replacement with the first alternate feed plate or the second alternate feed plate can be performed in a quick and simple manner without disconnecting the entire feed-through module 14 from the analytical module 16 or removing it from the housing 12. The exchange is performed by simply unscrewing the screws 148, swapping the feed plates and then re-threading the screws 148.

It should be appreciated that in lieu of securing the feed plate 112 to the connection structure 110 by the screws 148 as shown and described, the feed plate 112 may be secured to the connection structure 110 by a floating connection or a stab connection.

Figure 12:
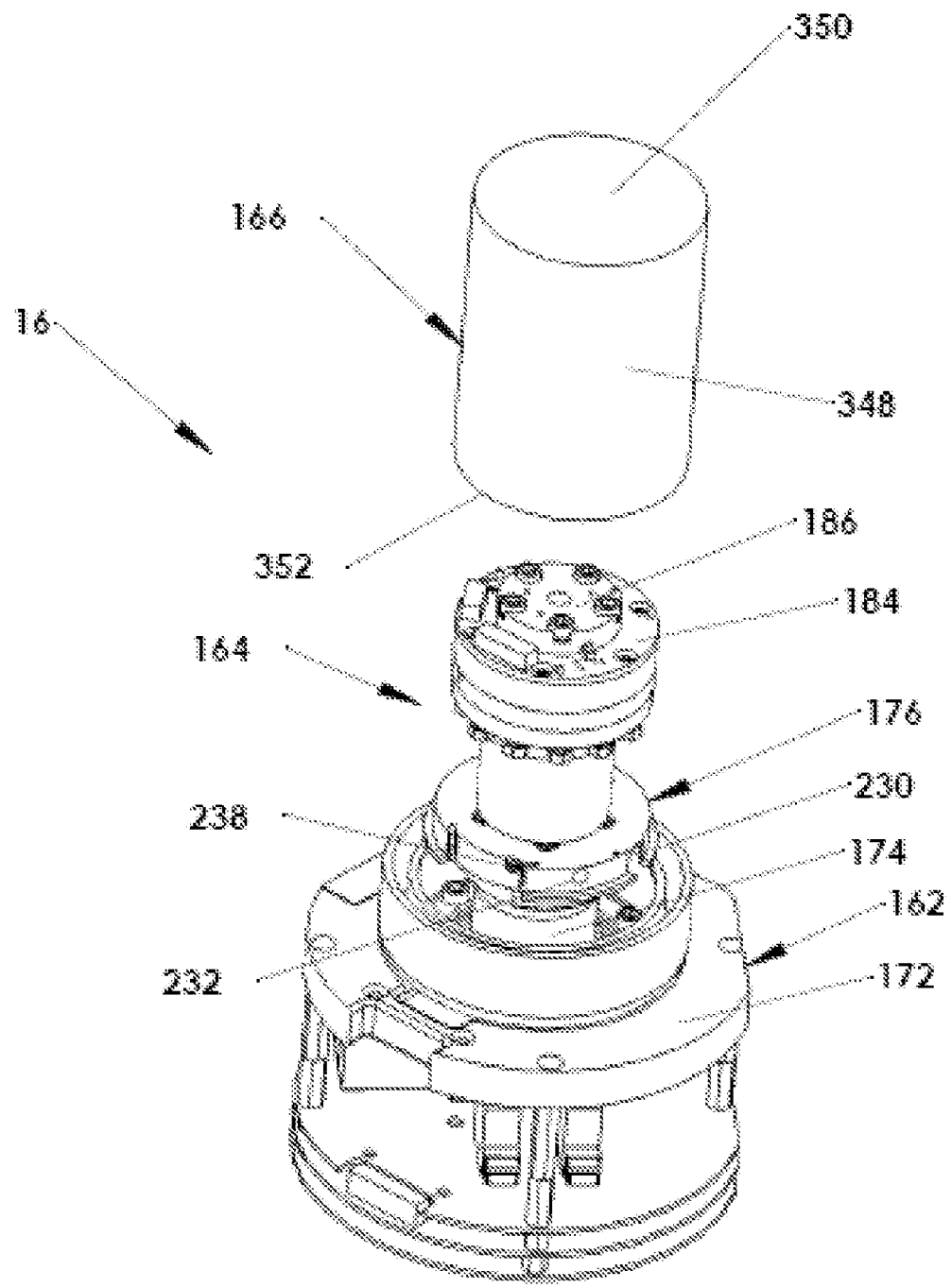
FIG. 12 shows a perspective view of the analytical module with an oven enclosure spaced above a column module.

As used herein with regard to components of the analytical module 16, the main electronics assembly 18, the analytical processor assembly 20 and the termination assembly 21, relative positional terms such as "top", "bottom", etc. refer to the position of the component in the context of the position of the analytical module 16 in FIG. 12. Such relative positional terms are used only to facilitate description and are not meant to be limiting.

III. Analytical Module

Figure 11:
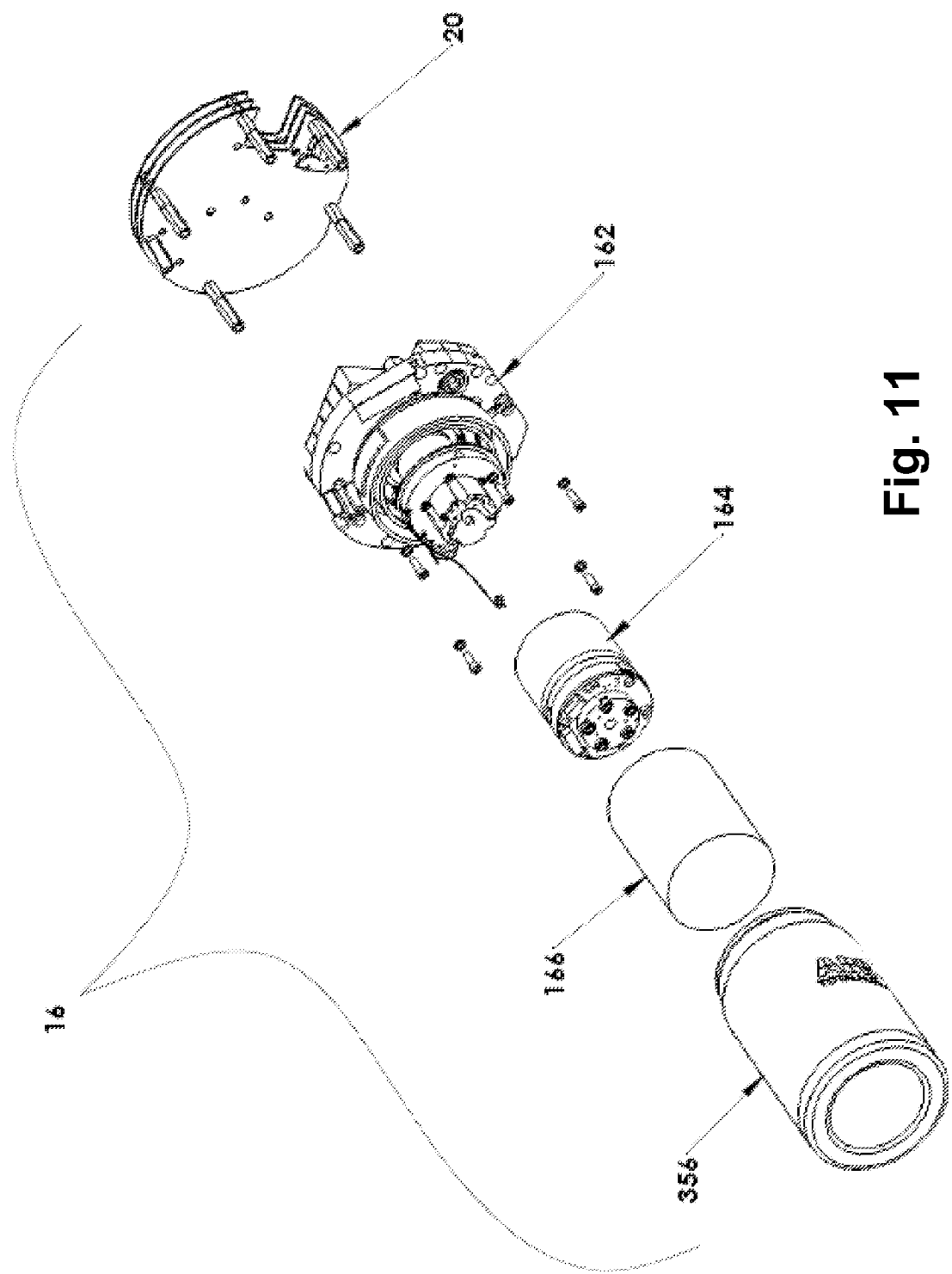
FIG. 11 shows an exploded view of the analytical module.

Referring now to FIGS. 11 and 12, the analytical module 16 generally comprises a manifold module 162, a gas chromatograph (GC) module 164, an oven enclosure 166, a dewar 356 and an analytical processor assembly 20.

Manifold Module

The manifold module 162 generally includes a primary manifold plate 170, a secondary manifold plate 172, a spacer 174 and a heater plate 176.

Figure 13:
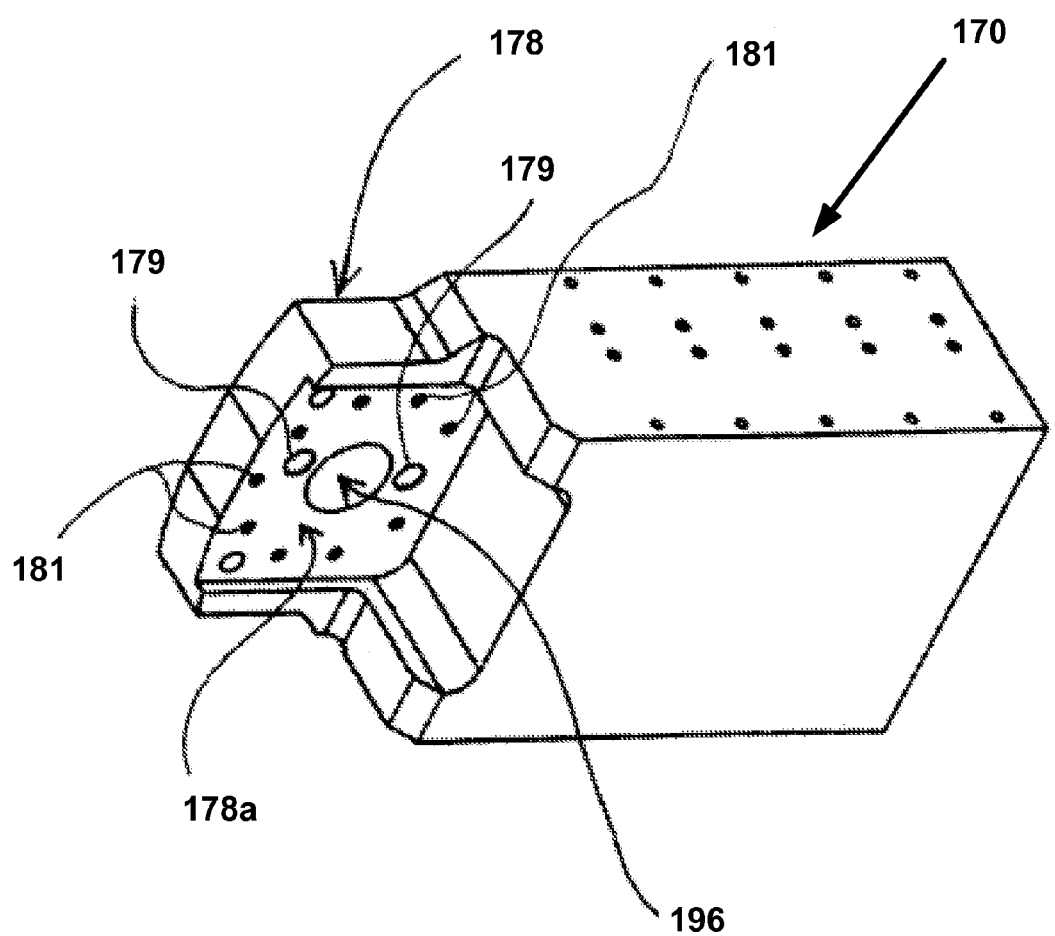
FIG. 13 shows a bottom perspective view of a primary manifold plate of the gas chromatograph without electrical flow control devices mounted thereto.
Figure 14:
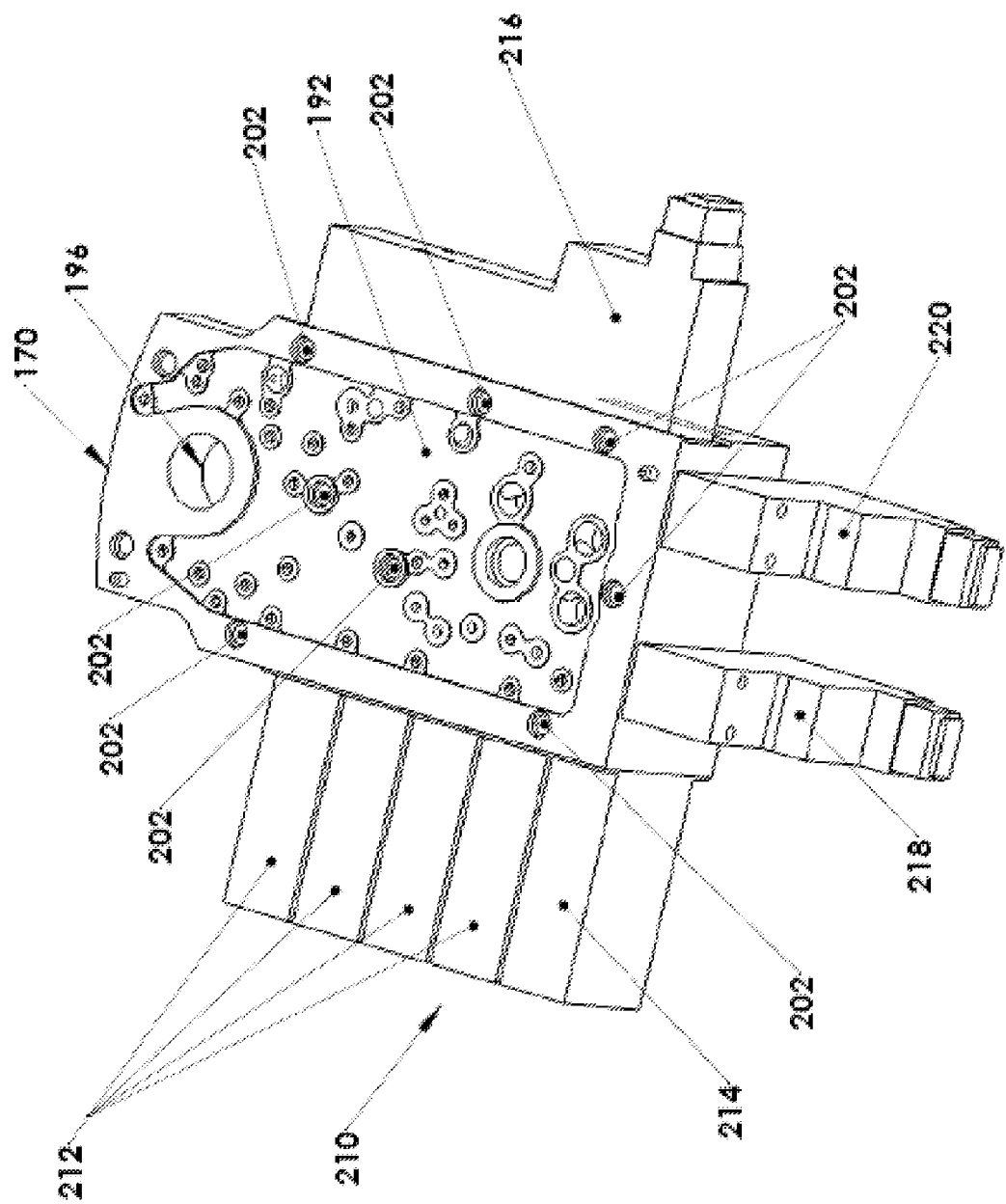
FIG. 14 shows a top perspective view of the primary manifold plate with electrical flow control devices mounted thereto.
Figure 15:
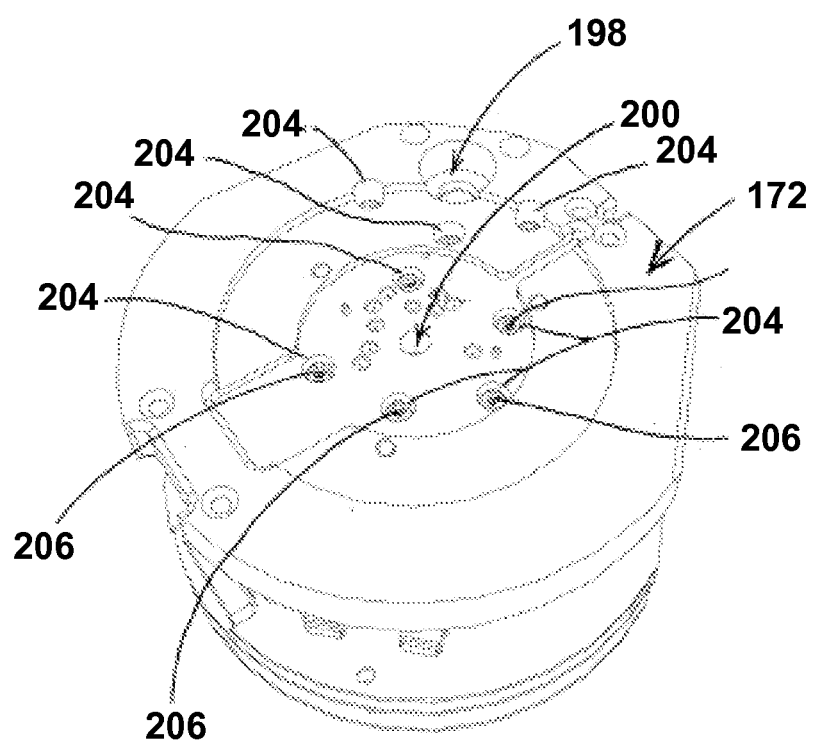
FIG. 15 shows a top perspective view of a secondary manifold plate of the gas chromatograph.

Referring now to FIGS. 13, 14 and 15, the primary and secondary manifold plates 170, 172 are each composed of a metal, such as aluminum. A gasket 192 is disposed between the primary and secondary manifold plates 170, 172. The primary manifold plate 170 includes a tongue 178 with a major face 178a that is adapted to interface with the second major face 124 of the base 116 in the feed-through module 14. An enlarged main mounting hole 196 extends through the tongue 178. A pair of guide holes 179 and a plurality of fluid openings 181 are formed in the major face 178a and are disposed around the main mounting hole 196. When the primary manifold plate 170 is secured to the feed-through module 14, the fluid openings 181 are connected to the inner passage openings 128 in the feed-through module 14 for fluid flow therebetween. A plurality of internal fluid passages is formed in the primary manifold plate 170 so as to form a first internal passage network, which is connected to the fluid openings 181.

An enlarged, countersunk main mounting hole 198 is formed in the secondary manifold plate 172 and is aligned with the main mounting hole 196 in the primary manifold plate 170. The main mounting holes 196, 198 are used to mount the analytical module 16 to the feed-through module 14, as will be discussed further below. A central mounting hole 200 extends through the secondary manifold 172 and is disposed along the central axis thereof. A plurality of threaded mounting holes 202 are formed in the primary manifold plate, and a plurality of corresponding mounting holes 204 are formed in the secondary manifold plate 172. The primary manifold plate 170 is secured to the secondary manifold plate 172 by screws 206 that extend through the mounting holes 204 in the secondary manifold plate 172 and are threadably received in the holes 202 in the primary manifold plate 170. A plurality of internal fluid passages is formed in the secondary manifold plate 172 so as to form a second internal passage network. When the primary and secondary manifold plates 170, 172 are secured together, the first internal passage network of the primary manifold plate 170 is connected to the second internal passage network of the secondary manifold plate 172 for fluid flow therebetween.

Electrical flow control devices 210 are secured to the primary manifold plate 170 and are connected into the first internal passage network to control the flow of carrier gas (such as helium) and sample gas (such as natural gas) to the GC module 164 and, more particularly, to the valve assembly 180. The flow control devices 210 include sample valves 212, a shut-off valve 214, a pilot valve 216 and first and second pressure regulator valves 218, 220. The flow control devices 210 are electrically connected to and controlled by the analytical PCA 160 of the analytical processor assembly 20. The sample valves 212 are three-way, normally closed, solenoid-actuated valves that selectively control the flow of sample gas from the sample inlet paths to the first and second GC valves 188, 190. The shut-off valve 214 is a three-way, normally open, solenoid-actuated valve that controls the flow of gas from the sample valves 212 to the first and second GC valves 188, 190. The pilot valve 216 is a four way, magnetically latching solenoid actuated valve that pneumatically controls the actuation of the first and second GC valves 188, 190. The first and second pressure regulators 218, 220 are proportional solenoid valves for controlling the pressure of the carrier gas supplied to the first and second GC valves 188, 190. Actuation of one of the sample valves 212 will cause gas from the sample line associated with the actuated sample valve 212 to be supplied to the first and second GC valves 188, 190, assuming the shut-off valve 214 is open.

Figure 16:
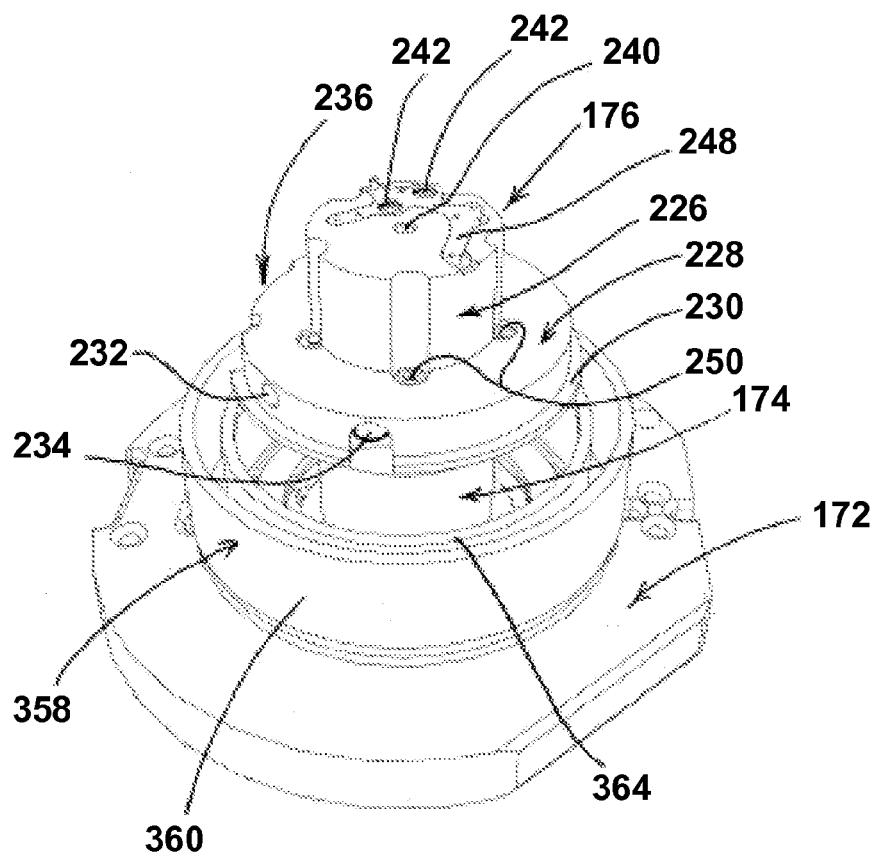
FIG. 16 shows a top perspective view of a spacer and a heater plate mounted to the secondary manifold plate.

Referring now to FIG. 16, the spacer 174 is composed of an insulating material, such as an insulating plastic or ceramic. In one embodiment, the spacer 174 is composed of chlorinated polyvinyl chloride (CPVC), which has good insulating properties and is heat and chemical resistant. The spacer 174 includes a cylindrical body with an annular flange disposed at an upper end thereof. A countersunk bore extends through the spacer 174 along the center axis thereof. A plurality of mounting holes with threaded inserts (or threaded holes) extend through the spacer 174 and are disposed around the countersunk bore. The spacer 174 is secured to the secondary manifold plate 172 by a single threaded bolt with a socket head, which extends through the countersunk bore, the central mounting hole 200 in the secondary manifold 172 and into a threaded bore in the primary manifold plate 170. The spacer 174 spaces the heater plate 176 above the secondary manifold plate 172 and limits thermal communication between the heater plate 176 and the secondary manifold plate 172. Internal flow passages for sample gas, carrier gas, vent gas, etc. extend through the spacer 174 and form a third internal passage network, which is connected to the second internal passage network of the secondary manifold plate 172.

Figure 41:
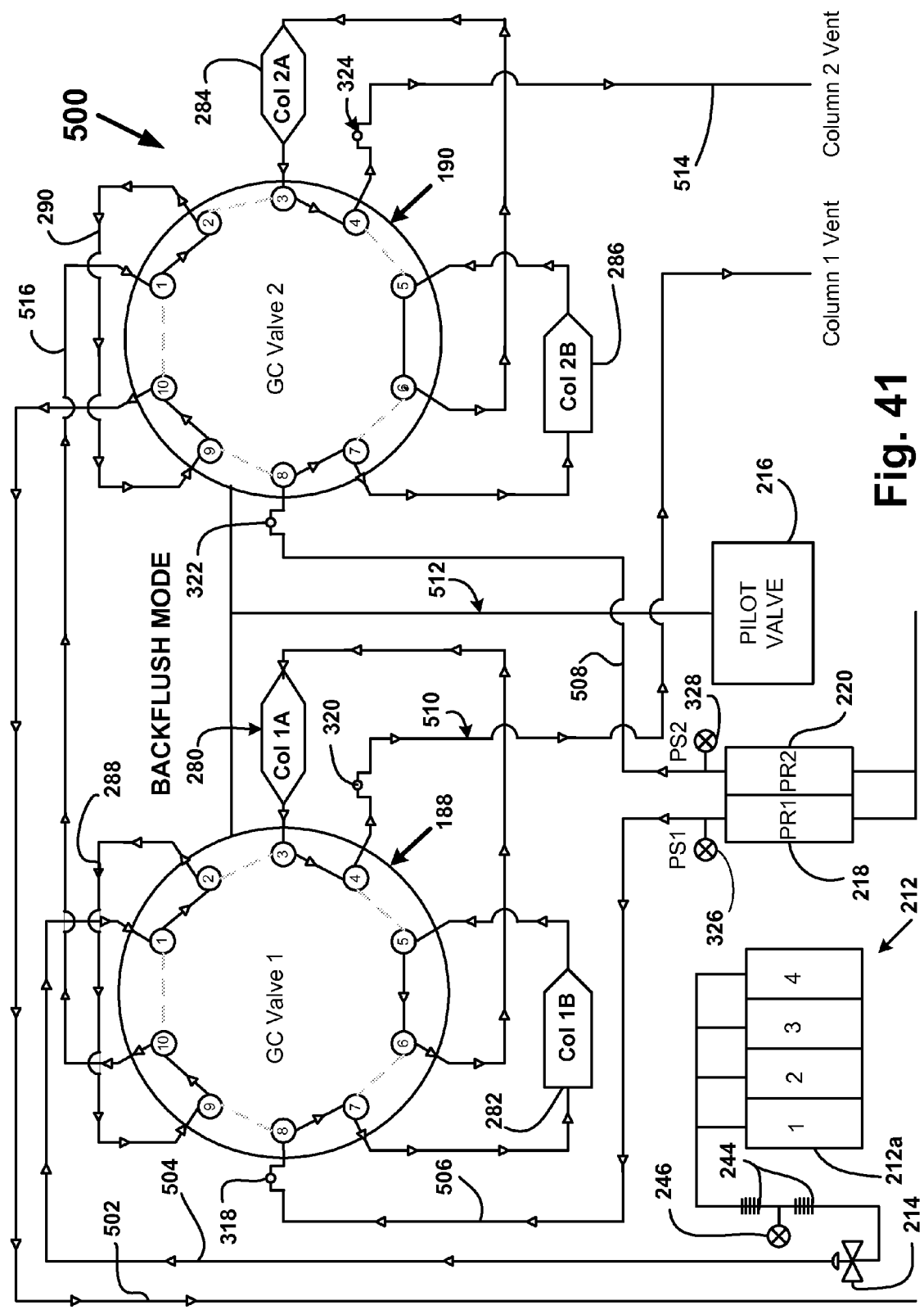
FIG. 41 shows a schematic diagram of the flow paths of sample gas and carrier gas through the gas chromatograph when the valve assembly is in a "backflush mode"
Figure 42:
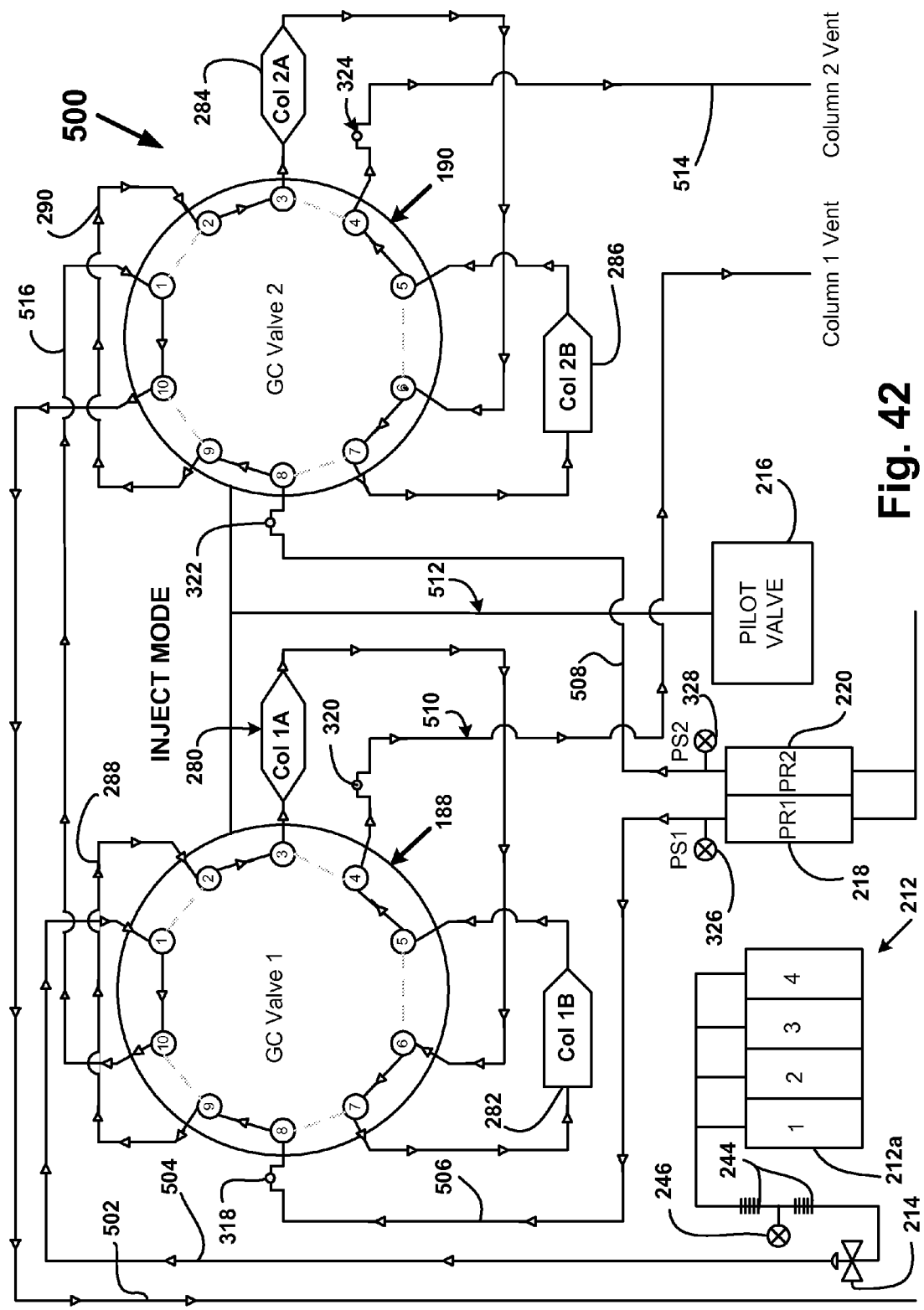
FIG. 42 shows a schematic diagram of the flow paths of sample gas and carrier gas through the gas chromatograph when the valve assembly is in an "inject mode"

The heater plate 176 is composed of aluminum or other conductive metal and comprises a generally cylindrical pillar 226 joined to a generally cylindrical pedestal 228 with an annular flange 230. A plurality of mounting holes are disposed around the pedestal 228 and extend longitudinally therethrough. A pair of bearings 232 are mounted in sockets formed in diametrically opposite portions of a side surface of the pedestal 228. A cartridge heater 234 is mounted in a tunnel that extends through the side surface of the pedestal 228. The cartridge heater 234 is electrically connected to and controlled by the analytical PCA 160 in the analytical processor assembly 20. An enlarged longitudinally-extending channel 236 is formed in the pedestal 228 and extends through the flange 230. The channel 236 accomodates a ribbon cable 237 (shown schematically in FIG. 34) that connects the GC PCBA 184 to the analytical processor assembly 20. An oven temperature sensor 238 (shown in FIG. 12 and schematically in FIG. 35) is mounted in a well that is formed in the pedestal 228 and is located in the channel 236. A threaded central bore 240 is formed in the pillar 226 of the heater plate 176 and extends along the center axis thereof. Outward from the central bore 240, a pair of sample conduits are formed in the pillar 226 and extend longitudinally therein. Each of the sample conduits includes a narrow inlet portion and an enlarged main portion, which is defined by a helically threaded interior wall. Cylindrical inserts 242 (shown in FIG. 16) composed of metal are disposed in the main portions of the sample conduits. In each sample conduit, the threaded interior wall cooperates with the insert to define a helical sample passage 244 that extends through the heater plate 176. The helical sample passages 244 are connected in series by a sample pressure sensor 246 in the valve assembly 180, as is schematically shown in FIGS. 41 and 42. The interconnected helical sample passages 244 increase the residence time of the sample gas in the heater plate 176, thereby improving the heating of the sample gas. An irregular gasket 248 is secured by pins to an upper end surface of the pillar 226. The heater plate 176 is secured to the spacer 174 by screws 250 that extend through the mounting holes in the heater plate 176 and are threadably received in the inserts in the mounting holes in the spacer 174. The helical sample passages 244 along with other internal flow passages for carrier gas, vent gas, etc. extend through the heater plate 176 and form a fourth internal passage network, which is connected to the third internal passage network of the spacer 174.

A cap 358 for engagement with the dewar 356 is secured to the secondary manifold plate 172. The cap 358 is composed of plastic and includes a cylindrical outer side wall 360 joined at a rounded edge to an annular end wall 362. An interior surface of the outer side wall 360 is threaded. A central portion of the end wall 362 has a recessed exterior surface and a plurality of holes extending therethrough. A cylindrical interior wall 364 is joined to an interior surface of the end wall 362 and extends upwardly therefrom. A metal clamp ring 366 with a plurality of holes formed therein is disposed radially inward from the interior wall 364 and adjoins an interior surface of the central portion of the end wall 362. Screws 368 extend through the holes in the clamp ring 366 and the cap 358 and are received in threaded openings in the secondary manifold plate 172, thereby securing the clamp ring 366 and, thus, the cap 358 to the secondary manifold plate 172.

GC Module

Figure 27:
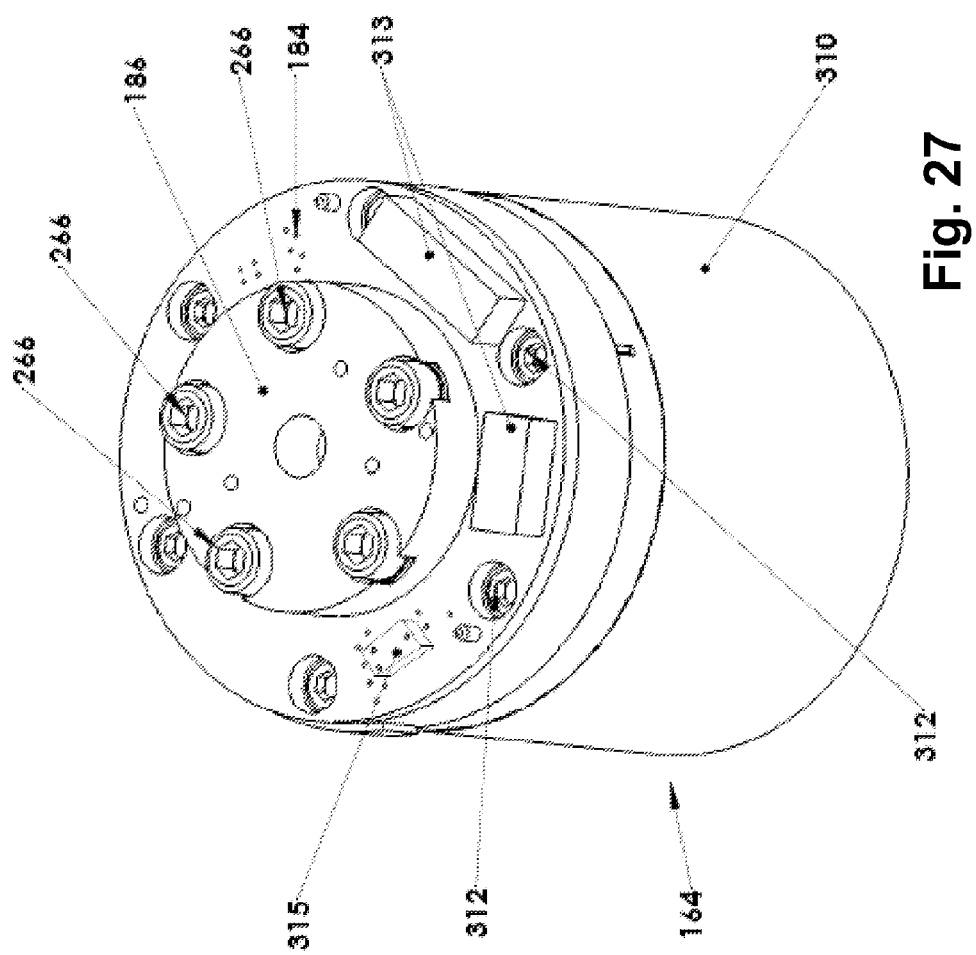
FIG. 27 shows a perspective view of the GC module.

The GC module 164 generally comprises a valve assembly 180, a column assembly 182, a GC PCBA 184 and a cover plate 186. FIG. 27 shows the GC module 164 fully assembled.

A plurality of internal flow passages for sample gas, carrier gas, vent gas, etc. extend through the valve assembly 180 and form a fifth internal passage network, which is connected to the fourth internal passage network of the heater plate 176. The fifth internal passage network comprises first and second GC valves 188, 190.

Figure 17:
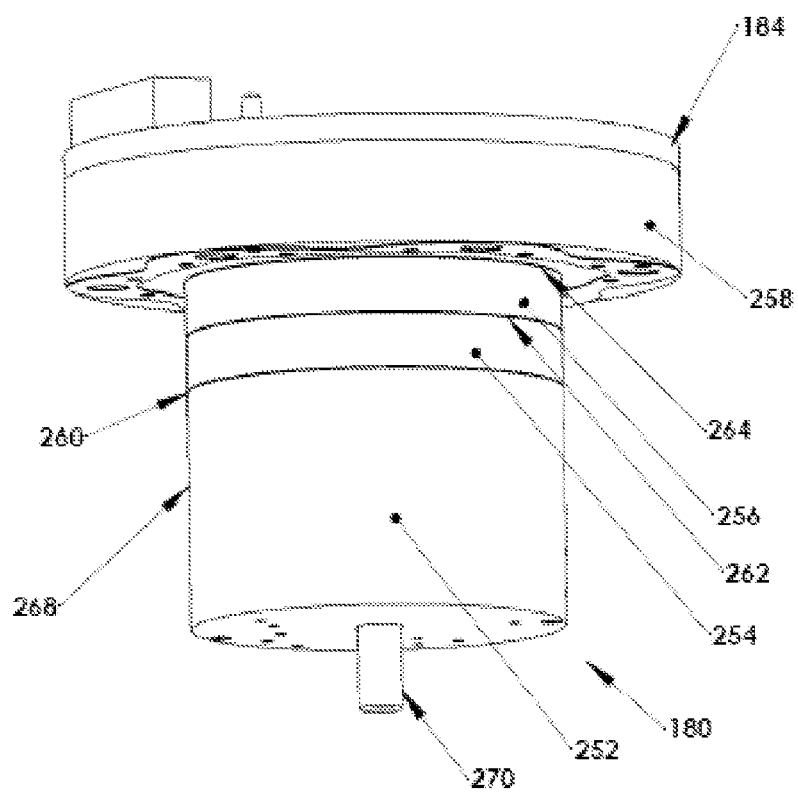
FIG. 17 shows a perspective view of a valve assembly of a GC module of the gas chromatograph.
Figure 18:
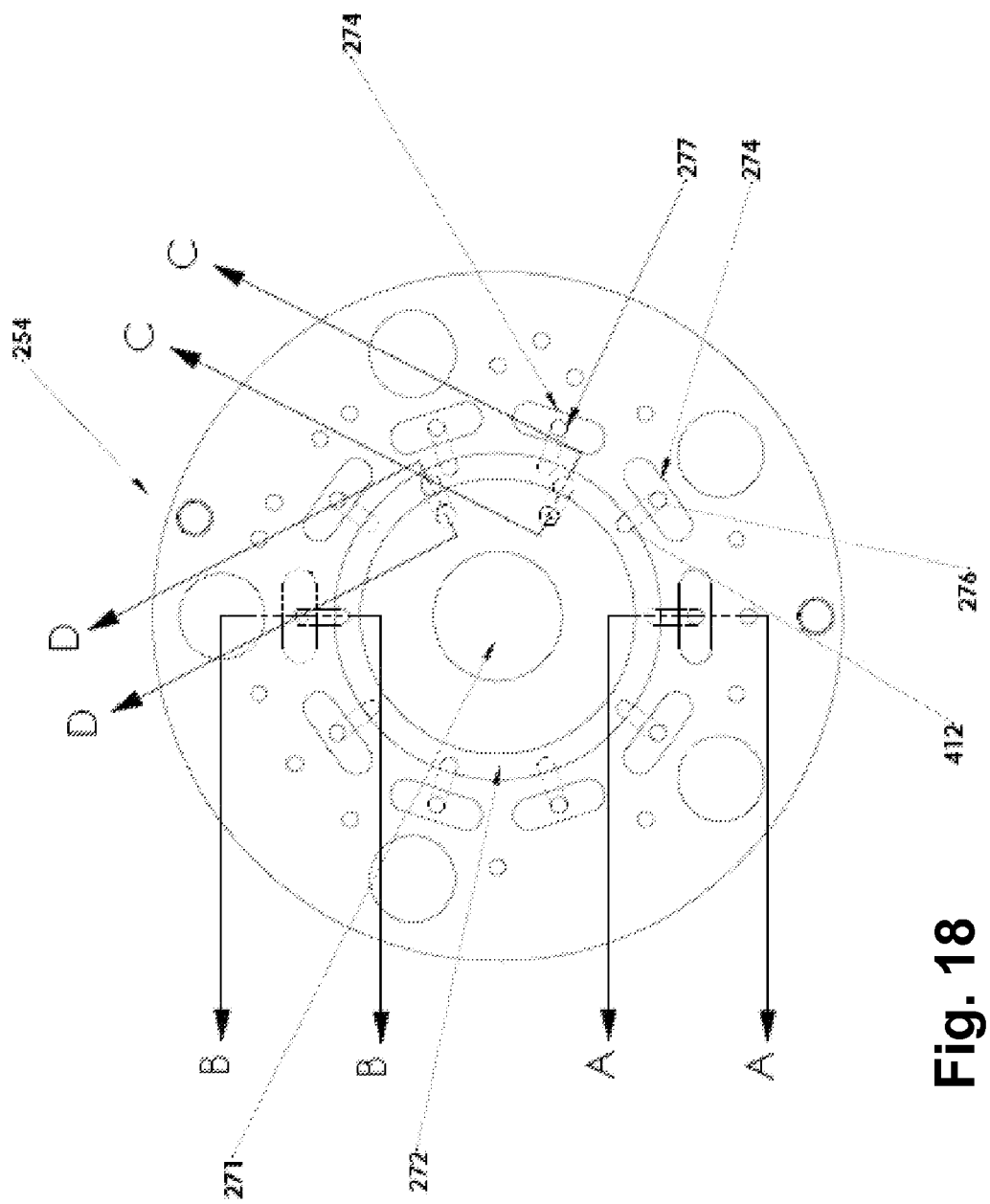
FIG. 18 shows a top plan view of a second valve plate of the valve assembly.
Figure 19:
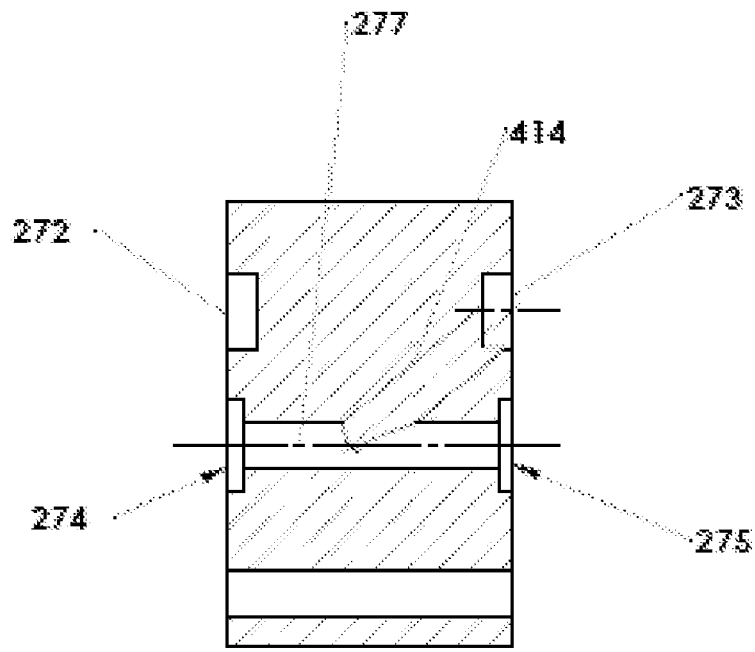
FIG. 19 shows a sectional view of the second valve plate taken along line A-A in FIG. 18.
Figure 20:
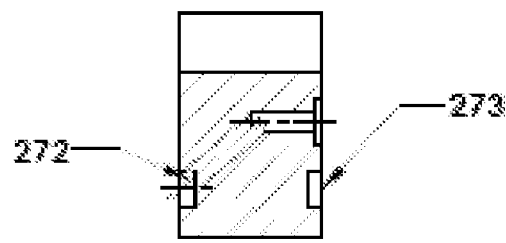
FIG. 20 shows a sectional view of the second valve plate taken along line B-B in FIG. 18.
Figure 21:
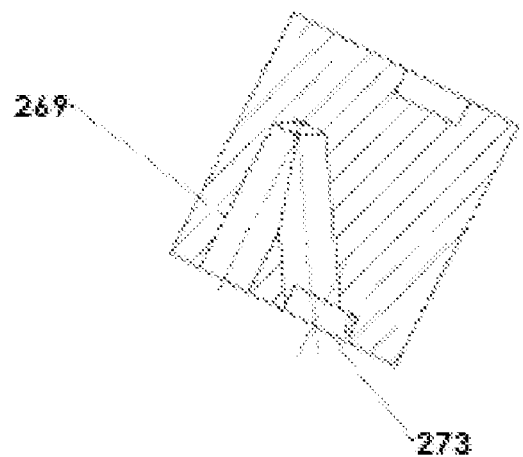
FIG. 21 shows a sectional view of the second valve plate taken along line C-C in FIG. 18.
Figure 22:
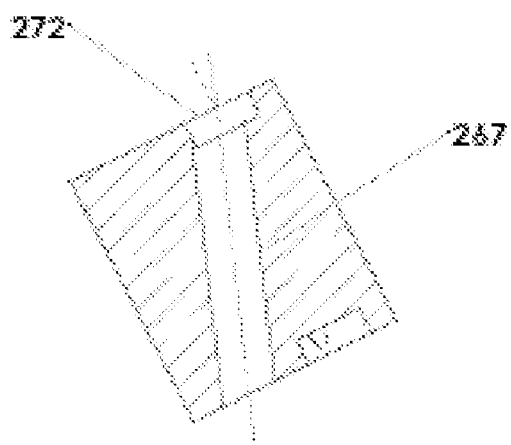
FIG. 22 shows a sectional view of the second valve plate taken along line D-D in FIG. 18.

Referring now to FIG. 17, the valve assembly 180 includes a first valve plate 252, a second valve plate 254, a third valve plate 256 and a detector plate 258. The first valve plate 252 has a cylindrical side surface and upper and lower end surfaces. A first diaphragm 260 is disposed between the upper end surface of the first valve plate 252 and a lower end surface of the second valve plate 254, while a second diaphragm 262 is disposed between an upper end surface of the second valve plate 254 and a lower end surface of the third valve plate 256. A gasket 264 is disposed between an upper end surface of the third valve plate 256 and a lower end surface of the detector plate 258. The first valve plate 252, the second and third valve plates 254, 256 and the detector plate 258 are coaxially disposed and are secured together by a plurality of screws 266 that extend through the cover plate 186, the GC PCBA 184, the detector plate 258 and the second and third valve plates 254, 256 and are threadably received in openings in the first valve plate 252. The first valve plate 252 and the second and third valve plates 254, 256 have substantially the same diameters so as to form a mandrel 268 for the column assembly 182. The mandrel 268 has a substantially smaller diameter than the detector plate 258. In this manner, when the column assembly 182 is mounted to the mandrel 268, the column assembly 182 abuts against an annular portion of the lower end surface of the detector plate 258, which is disposed radially outward from the mandrel 268. The valve assembly 180 is secured to the heater plate 176 by an elongated bolt 270 that extends through the center of the cover plate 186, the GC PCBA 184 and the valve assembly 180 and is threadably received in the central bore 240 of the heater plate 176.

An upper end surface of the first valve plate 252, the first diaphragm 260 and a lower end surface of the second valve plate 254 cooperate to define the first GC valve 188 (shown schematically in FIGS. 41 and 42), while an upper end surface of the second valve plate 254, the second diaphragm 262 and a lower end surface of the third valve plate 256 cooperate to define the second GC valve 190 (shown schematically in FIGS. 41 and 42). Each of the GC valves 188, 190 have ports 1-10 (see FIGS. 41 and 42). The ports 1-10 of the first GC valve 188 are formed in the first valve plate 252, while the ports 1-10 of the second GC valve 190 are formed in the third valve plate 256. The first and second GC valves 188, 190 each have two modes, namely an "inject" mode and a "backflush" mode.

Referring now to FIGS. 18-22, the second valve plate 254 is cylindrical and includes the upper and lower end surfaces, respectively. A central bore 271 extends through the valve plate 254, along the central axis thereof. Radially outward from the central bore 271, an annular upper manifold groove 272 is formed in the upper end surface 254a and an annular lower manifold groove 273 is formed in the lower end surface 254b. The upper manifold groove 272 is connected to an internal first carrier gas passage 267, while the lower manifold groove 273 is connected to an internal second carrier gas passage 269. The first and second carrier gas passages are connected to the pilot valve 216 for receiving carrier gas therefrom. The pilot valve 216 only provides carrier gas to one of the first and second carrier gas passage and, thus, one of the upper and lower manifold grooves 272, 273, at a time. When the upper manifold groove 272, but not the lower manifold groove 273, is provided with carrier gas, the first and second GC valves 188, 190 are in the "backflush" mode. Conversely, when the lower manifold groove 273, but not the upper manifold groove 272, is provided with carrier gas, the first and second GC valves 188, 190 are in the "inject" mode.

A substantially circular pattern of elliptical upper depressions 274 are formed in the upper end surface of the second valve plate 254, around the upper manifold groove 272, and a circular pattern of elliptical lower depressions 275 are formed in the lower end surface of the second valve plate 254, around the lower manifold groove 273. The upper and lower depressions 274, 275 are aligned with each other, respectively. A first series of alternate upper depressions 274a are connected to the upper manifold groove 272, while a second series of alternate upper depressions 274b are connected to the lower manifold groove 273, wherein the upper depressions 274a in the first series are separated by the upper depressions 274b in the second series and vice versa. Similarly, a first series of alternate lower depressions 275a are connected to the upper manifold groove 272, while a second series of alternate lower depressions 275b are connected to the lower manifold groove 273, wherein the lower depressions 275a in the first series are separated by the lower depressions 275b in the second series and vice versa. The first series of upper depressions 274a and the first series of lower depressions 275a are aligned and connected by internal first bores 276, respectively, while the second series of upper depressions 274b and the second series of lower depressions 275b are aligned and connected by internal second bores 277. The first bores 276 are connected to the upper manifold groove 272 by internal first passages 412, while the second bores 277 are connected to the lower manifold groove 273 by internal second passages 414.

As a result of the construction described above, when carrier gas is supplied to the upper manifold groove 272, carrier gas is provided to the first series of upper depressions 274a and to the first series of lower depressions 275a; and when carrier gas is supplied to the lower manifold, carrier gas is provided to the second series of upper depressions 274b and the second series of lower depressions 275b. In other words, when the first and second GC valves 188, 190 are in the "backflush" mode, carrier gas is provided to the first series of upper depressions 274a and to the first series of lower depressions 275a; and when the first and second GC valves 188, 190 are in the "inject" mode, carrier gas is provided to the second series of upper depressions 274b and the second series of lower depressions 275b.

Figure 23:
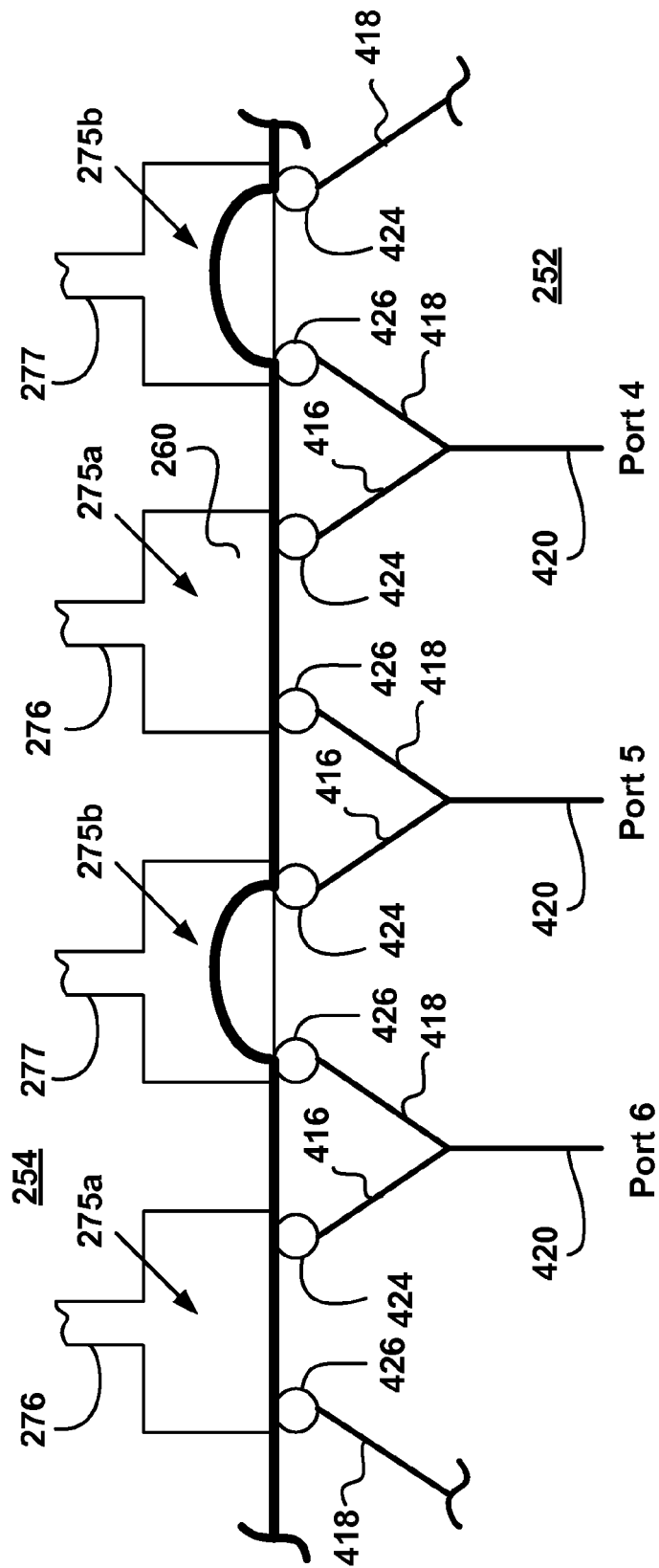
FIG. 23 shows a schematic diagram of a portion of a first GC valve of the valve assembly, wherein the first GC valve is in a backflush mode.
Figure 24:
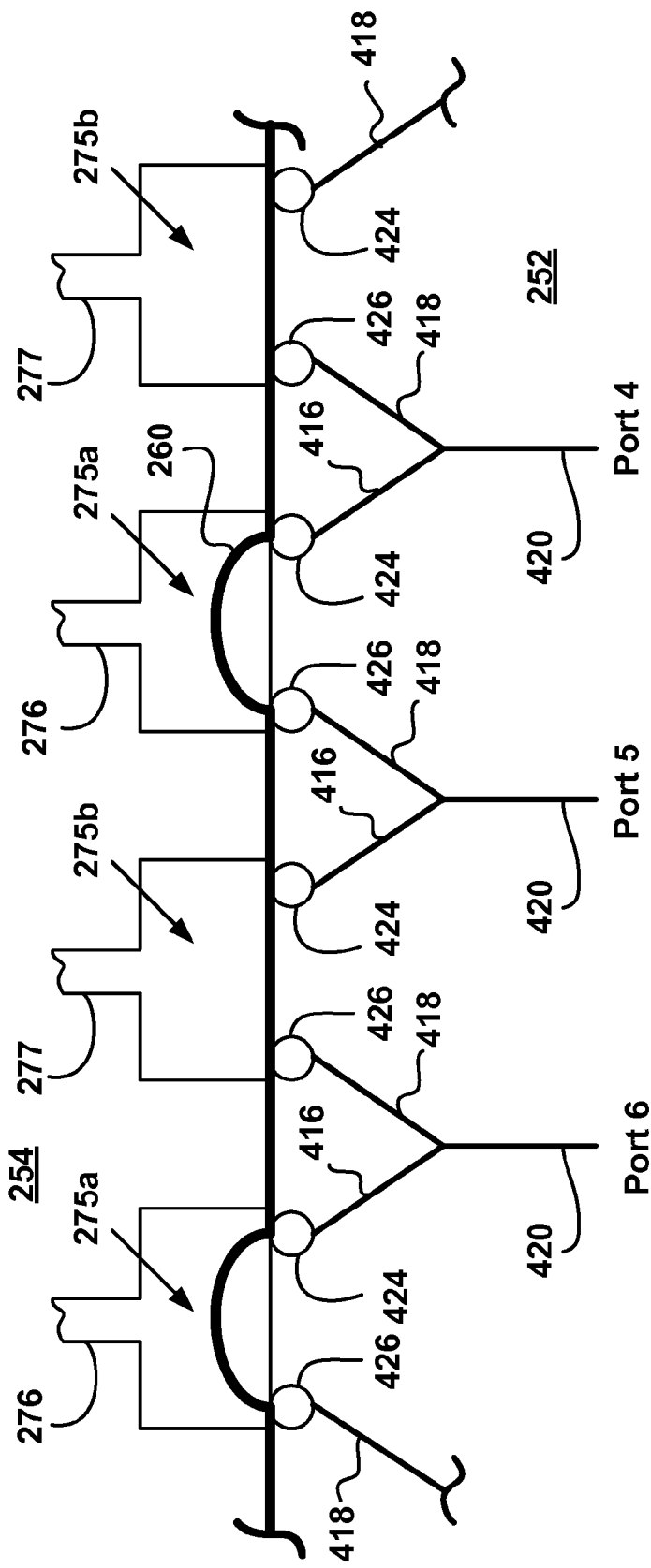
FIG. 24 shows a schematic diagram of a portion the first GC valve, wherein the first GC valve is in an inject mode.

Referring now to FIGS. 23 and 24, the construction and operations of the ports 1-10 of the first GC valve 188 will be described. The construction and operation of the ports 1-10 of the second GC valve 190 will not be described, it being understood that the ports 1-10 of the second GC valve 190 have substantially the same construction and operation as the ports of the first GC valve 188, except for being formed in the lower end surface of the third valve plate 256. Each port of the first GC valve 188 comprises a pair of connector passages 416, 418 formed in the first valve plate 252 and arranged in a V-shaped configuration. Upper ends of the connector passages 416, 418 have openings 424, 426 formed in the upper end surface 252a, respectively. Lower ends of the connector passages 416, 418 are connected together at a junction point, which is connected to an inlet/outlet line 420. The openings 424, 426 are disposed at the same radial distance from the center of the first valve plate 252. The opening 426 of a port and the opening 424 of an adjacent port are aligned with a lower depression 275a, while the other opening 424 of the port and the opening 426 of the other adjacent port are aligned with an adjacent lower depression 275b. Thus, with regard to ports 6 and 5, the opening 426 of port 6 and the opening 424 of port 5 are both aligned with a lower depression 275b, while the opening 426 of port 5 and the opening 424 of port 4 are both aligned with an adjacent lower depression 275a.

The first diaphragm 260 overlays the opening 426 of port 6 and the opening 424 of port 5. When carrier gas is not supplied to the lower manifold groove 273 and thus does not enter the lower depression 275b that is aligned with the opening 426 of port 6 and the opening 424 of port 5, gas from the inlet/outlet line 420 of port 5 exits the opening 424 of port 5 and deflects the first diaphragm 260 into the lower depression 275b (as shown in FIG. 23), thereby forming a travel path through which the gas travels to the opening 426 of port 6. In this manner, port 5 is connected to port 6, as is shown in FIG. 41. When carrier gas is supplied to the lower manifold groove 273 and enters the lower depression 275b, the carrier gas presses the first diaphragm 260 against the opening 424 of port 5 and the opening 426 of port 6 (as shown in FIG. 24), thereby preventing gas from the outer opening 424 of port 5 from traveling to the opening 426 of port 6. In this manner, the port 5 is disconnected from port 6, as is shown in FIG. 42.

As can be appreciated from the foregoing description, each depression 274, 275 is operable to disconnect or connect aligned ports of its corresponding GC valve 188, 190 based on the presence or absence of carrier gas in the depression 274. As set forth above, the supply of carrier gas to the depressions 274, 275 is determined by the supply of carrier gas to the upper and lower manifold grooves and, thus the mode of the first and second GC valves 188, 190. Thus, when the first and second GC valves 188, 190 are in the "backflush" mode, carrier gas is provided to the first series of upper depressions 274a and to the first series of lower depressions 275a, which connects the port pairs of 1&2, 3&4, 5&6, 7&8, and 9&10 of the first and second GC valves 188, 190 and disconnects the port pairs of 2&3, 4&5, 6&7, 8&9, and 10&1 of the first and second GC valves 188, 190, as is shown in FIG. 41. When the first and second GC valves 188, 190 are in the "inject" mode, carrier gas is provided to the second series of upper depressions 274b and the second series of lower depressions 275b, which connects the port pairs of 2&3, 4&5, 6&7, 8&9, and 10&1 of the first and second GC valves 188, 190 and disconnects the port pairs of 1&2, 3&4, 5&6, 7&8, and 9&10 of the first and second GC valves 188, 190, as is shown in FIG. 42.

Figure 25:
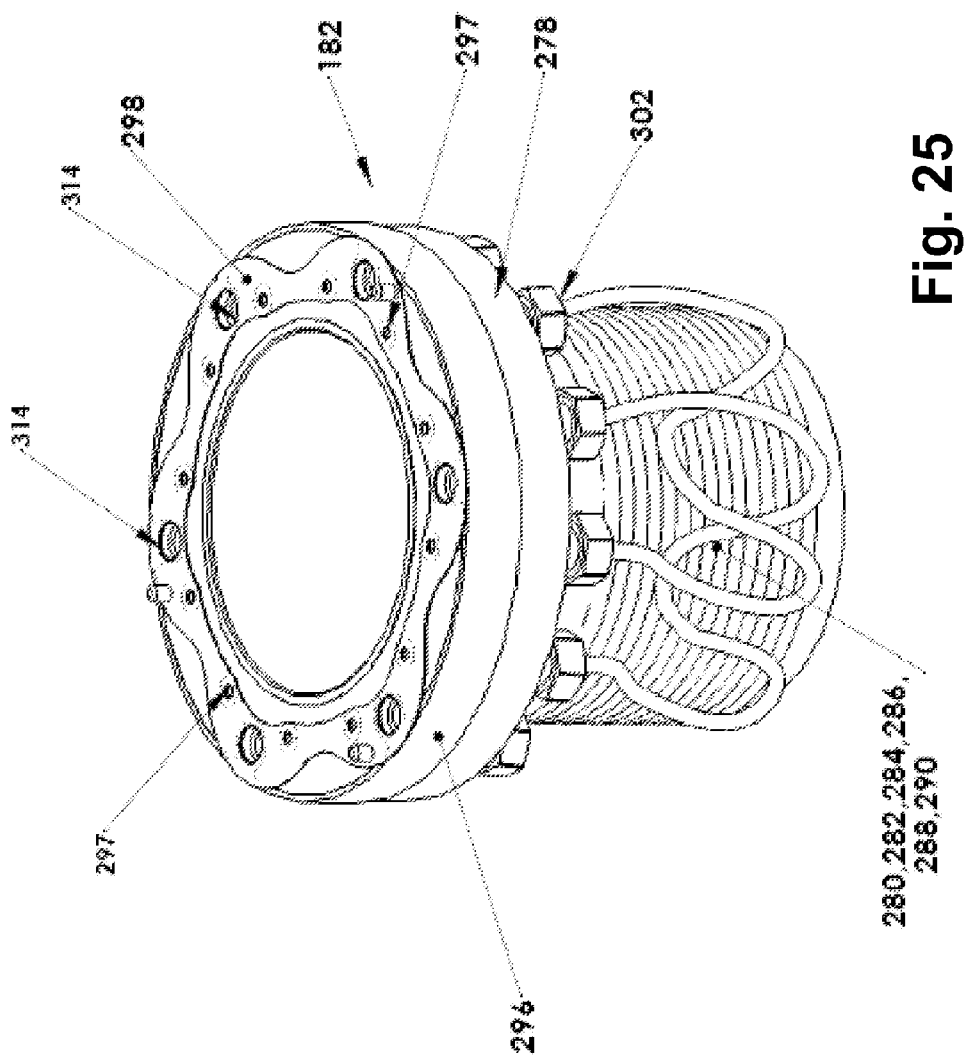
FIG. 25 shows a perspective view of a column assembly of the GC module.

As shown in FIG. 25, the column assembly 182 generally includes a spool 278, first preliminary column 280, first column 282, a second preliminary column 284, a second column 286 and first and second sample loops 288, 290.

Figure 26:
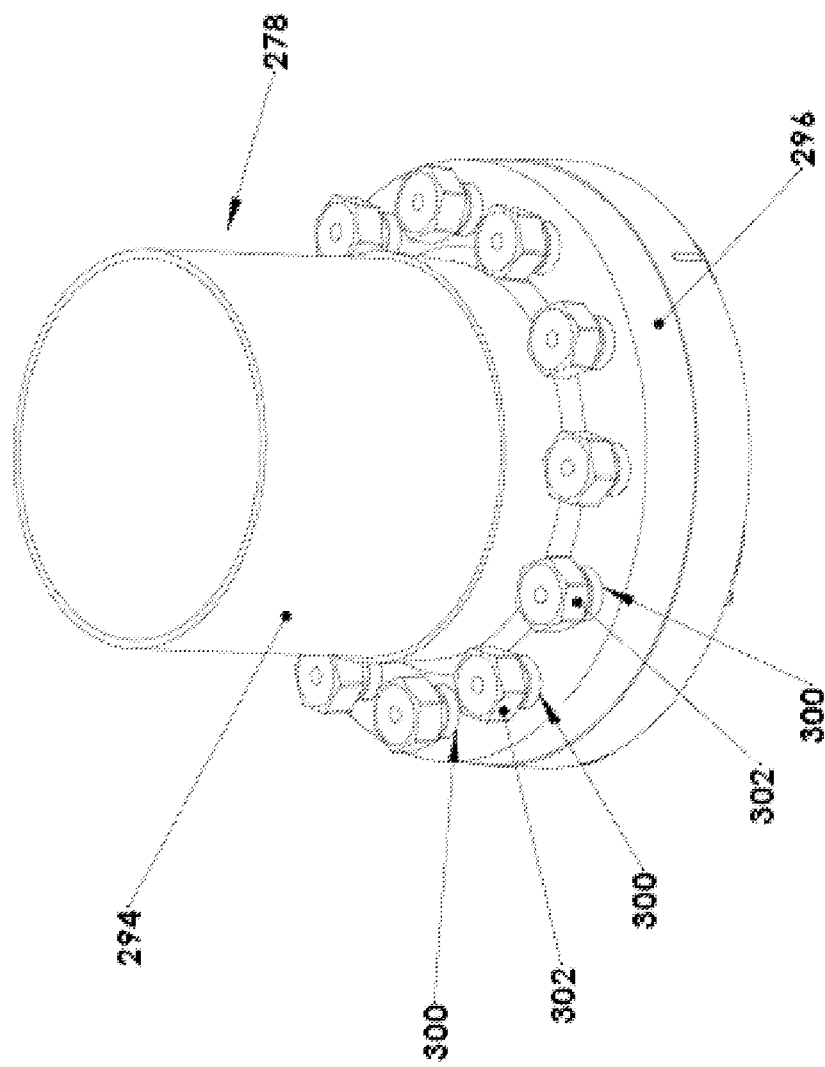
FIG. 26 shows a perspective view of a spool of the column assembly.

Referring now to FIG. 26, the spool 278 includes a hollow cylindrical body 294 with open upper and lower ends and an annular flange 296 disposed around the upper end. A plurality of flow openings 297 are formed on a top side of the flange 296. A gasket 298 is secured by pins to the top side of the annular flange 296. The gasket 298 has openings aligned with the flow openings 297 in the flange 296. On a bottom side of the flange 296, a plurality of threaded openings 300 are disposed around the flange 296. The flange 296 has a plurality of internal passages that connect the flow openings 297 to the openings 300. These internal passages form a sixth internal passage network. Ends of the columns and sample loops 280-290 are connected to fitting assemblies 302 threadably secured in the openings 300, respectively. Each fitting assembly 302 may be a compression fitting comprising a male nut 304 and a ferrule 306. The male nuts 304 are threadably secured in the openings 300 and extend outwardly therefrom, while the ferrules 306 are disposed in the openings 300 and are compressed by the male nuts 304. The ends of the columns and sample loops 280-290 extend through the male nuts 304 and the ferrules 306 and are held in place in the openings 300 by the compression of the ferrules 306. Disc-shaped filters 308 are secured over the ends of the columns and sample loops 280-290 inside the openings 300. The filters 308 are comprised of sintered stainless steel with 0.5 micron openings.

The columns 280-286 are packed columns, each of which may be comprised of a stainless steel tube having an inner diameter of 2 to 4 mm and a length of 1 to 4 meters. Each tube is packed with a suitable adsorbent, which may be organic and/or inorganic, and which is ground and screened to provide a range of particle sizes that extend from about 30 mesh to about 120 mesh. Ends of each tube contain stainless steel braided cable terminations to retain the adsorbent. In addition, the filters 308 in the openings 300 of the spool 278 help prevent migration of the adsorbent. It should be appreciated that in lieu of being packed columns, the columns 280-286 may instead be open tubular columns, such as fused silica open tubular (FSOT) columns. A FSOT column comprises a fused silica tube having an exterior polyimide coating and an interior stationary phase coating comprising a support and an adsorbent. It should also be appreciated that the gas chromatograph of the present invention is not limited to four columns and two sample loops. The gas chromatograph of the present invention may have any number of columns and sample loops, provided there is at least one column and at least one sample loop.

The columns and the sample loops 280-290 are wound around the body 294 of the spool 278 and have their ends secured to the fitting assemblies 302 as described above. The columns and the sample loops 280-290 may be wound by hand or by machine. In addition, the columns and the sample loops 280-290 may be wound directly on the spool 278, or on a separate device and then transferred as a coil to the spool 278. After the columns and sample loops 280-290 are wound around the spool 278 and connected to the fitting assemblies 302, the wound columns and the wound sample loops 280-290 are fully encapsulated in a thermal resin 310, i.e., a resin that is electrically insulating and thermally conductive. An example of a thermal resin is an epoxy resin filled with a conductive metal or metal compound, such as silver, alumina or aluminum nitride. The thermal resin 310 secures the columns and the sample loops 280-290 in position and provides greater isothermal heating and thermal stability of the columns and the sample loops 280-290.

The column assembly 182 is secured to the valve assembly 180 by a plurality of radially-outward screws 312 that extend through the GC PCBA 184 and the detector plate 258 and are threadably received in openings 314 in the flange 296 of the spool 278. When the column assembly 182 is secured to the valve assembly 180, the mandrel 268 extends through the upper end of the spool body 294 and the pillar 226 of the heater plate 176 extends through the lower end of the spool body 294, with both the mandrel 268 and the pillar 226 being disposed inside the spool body 294 and abutting against each other. In addition, the top side of the flange 296 of the spool 278 abuts the annular portion of the lower end surface of the detector plate 258. With the flange 296 and the detector plate 258 so positioned, the flow openings 297 in the flange 296 are connected to flow opening in the detector plate 258, thereby connecting the fifth internal passage network in the valve assembly 180 to the sixth internal passage network in the spool 278. The gasket 298 of the spool 278 abuts against the annular portion of the lower end surface of the detector plate 258.

The GC PCBA 184 is secured to the detector plate 258 by the radially-outward screws 312, the screws 266 and by the bolt 270. The GC PCBA 184 includes electrical connectors 313 and memory 315 mounted to a top side of a disc-shaped circuit board 316. The memory 315 may be electrically erasable programmable read-only memory (EEPROM). The memory 315 stores factory calibration information, chromatographic calibration constants, peak times, settings for the first and second pressure regulator valves 218, 220 and electronic identification of the gas chromatograph 10 and/or the GC module 164, including serial number, revision level and build date. The GC PCBA 184 also includes a first reference TCD 318, a first sensor TCD 320, a second reference TCD 322, a second sensor TCD 324, first and second carrier pressure sensors 326, 328 and the sample pressure sensor 246, all of which are secured to a bottom side of the circuit board 316 and extend downwardly therefrom. When the GC PCBA 184 is secured to the valve assembly 180, the TCDs 318-324 and the pressure sensors 246, 326, 328 extend into openings 332-344 in an upper side of the detector plate 258, respectively, and become connected into the fifth internal passage network of the valve assembly 180. The GC PCBA 184 is connected to the analytical PCA 160 by the ribbon cable 237 (shown schematically in FIG. 34).

The TCDs 318-324 can be any of a number of types of temperature sensing elements, including but not limited to negative temperature coefficient thermistors ("NTC thermistors"), or platinum RTD's, etc. These temperature sensing elements have a resistance value that varies as a function of temperature. NTC thermistors are the most common due to their high thermal sensitivity, or resistance versus temperature relationship. The term "thermistor bead" or just "bead" is sometimes used interchangeably since the sensing device is often a sensing element coated in glass and suspended on wires between two mounting posts or other support structure.

A thermistor (such as the second TCD 320) is heated by passing a current through it in such a way that it elevates its own temperature and correspondingly changes its own resistance, until its reaches a point of equilibrium such that the energy used to heat the thermistor is balanced by the energy that is dissipated or lost. The rate of energy lost by the thermistor is due to the combination of its own temperature, the thermal conductivity of its own support structure, the thermal conductivity, temperature, heat capacity and flow rate of the surrounding gas, and the temperature of the wall of the cavity or chamber that houses it. This mode of operation for the thermistor is referred to as the self-heated mode. Since the temperature of the chamber wall that the thermistor is placed in is held fairly constant at one temperature in most chromatographic applications, the variables that modulate the thermistor's heat loss the most are related to the physical properties of the gas flowing by it. Therefore, the gas chromatograph 10 minimizes the changes in the pressure of the gas as well as its flow rate in the vicinity of the thermistor. This is done in an effort to minimize the amount that these variables modulate the energy loss of the thermistor leaving the thermal conductivity of the gas as the prime variable of measurement. The heat capacity of the gas also contributes to the detector response, but is less significant.

Although the gas chromatograph 10 is described as using TCDs, it should be appreciated that other detectors are available and may be used in the gas chromatograph.

Oven Enclosure

Referring back to FIG. 12, the oven enclosure 166 is composed of a conductive metal, such as stainless steel or aluminum, and has a cylindrical side wall 348, a top end wall 350, and a circular bottom edge 352 defining a bottom opening. An annular groove is formed in an inside surface of the side wall 348. The oven enclosure 166 is disposed over the GC module 164, with the bottom edge 352 resting on the flange 230 of the heater plate 176. With the oven enclosure 166 so disposed, the oven enclosure 166 cooperates with the heater plate 176 to define an oven space, within which the GC module 164 is disposed. The oven enclosure 166 is removably secured to the heater plate 176 by a bayonet type connection formed by the engagement of the bearings 232 of the heater plate 176 with the groove in the interior surface of the side wall 348 of the oven enclosure 166. The oven enclosure 166 helps conduct heat from the heater plate 176 around the column assembly 182 to provide a more even temperature distribution within the column assembly 182 and to help isolate the column assembly 182 from the ambient temperature conditions. A heating element may be secured to the oven enclosure 166 to further improve the temperature distribution and thermal isolation of the column assembly 182.

Dewar

Referring back to FIGS. 10 and 11, the dewar 356 is cylindrical in shape and has a hollow interior and a closed outer end. An inner portion of the dewar 356 has a narrowed diameter, thereby forming a neck. The neck includes an exterior thread and an annular rim that defines an enlarged opening through which the interior may be accessed. The dewar 356 includes an inner shell nested within an outer shell so as form a narrow space therebetween. The inner and outer shells are sealed together at the neck. The narrow space between the inner and outer shell is evacuated almost entirely of air to produce a vacuum that prevents conduction and convection of heat. An inner surface of the outer shell and an outer surface of the inner shell are reflective or have reflective coatings to prevent heat from being transmitted via radiation. The inner and outer shells may be formed from stainless steel or other metal.

The dewar 356 is disposed over the oven enclosure 166, with the neck threadably secured to the cap 358 and the interior wall 364 of the cap 358 disposed inside the opening in the dewar 356. With the dewar 356 so disposed, the oven enclosure 166, the GC module 164, the heater plate 176 and the spacer 174 are disposed within the interior of the dewar 356, which provides an isolated environment in which the temperature of the oven space and thus the column assembly 182 can be closely regulated.

Analytical Processor Assembly

Figure 28:
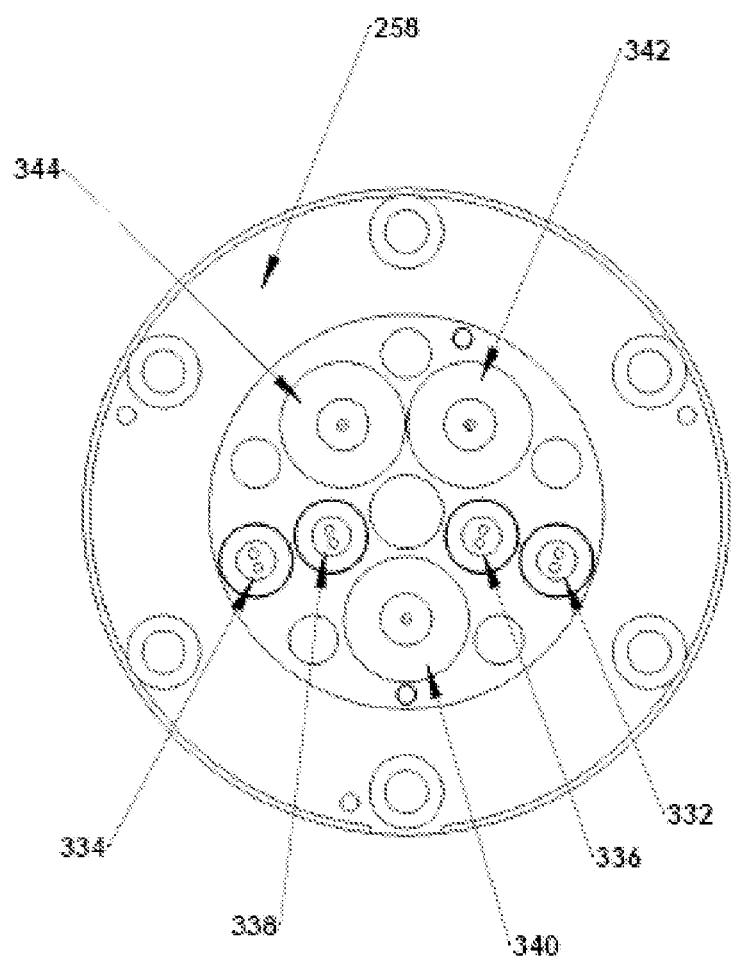
FIG. 28 shows a top plan view of a detector plate of the valve assembly of the GC module.
Figure 29:
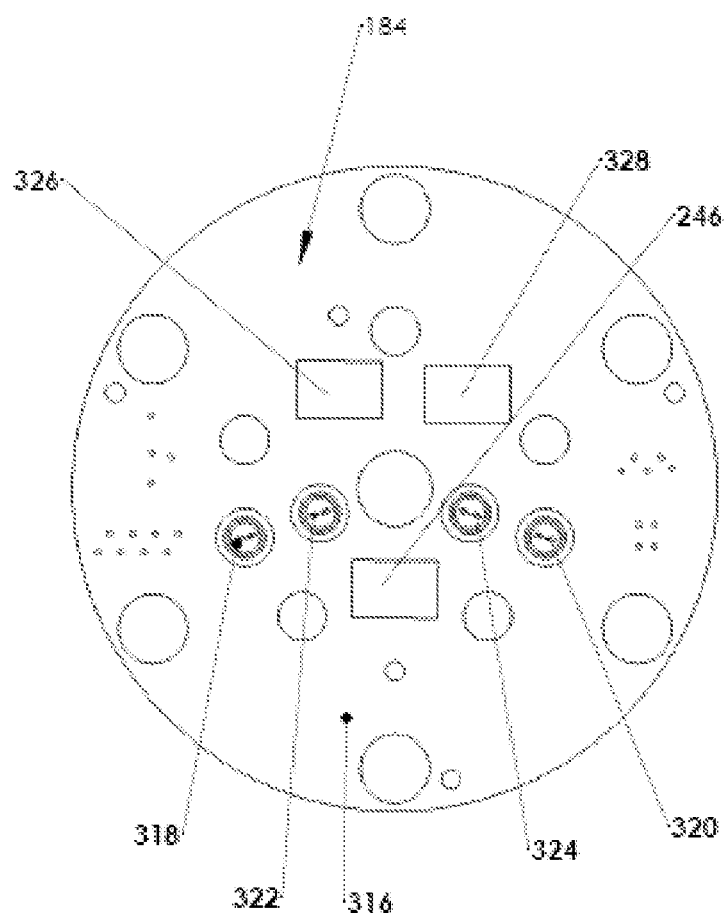
FIG. 29 shows a bottom plan view of a printed circuit board assembly mounted to the detector plate.
Figure 30:
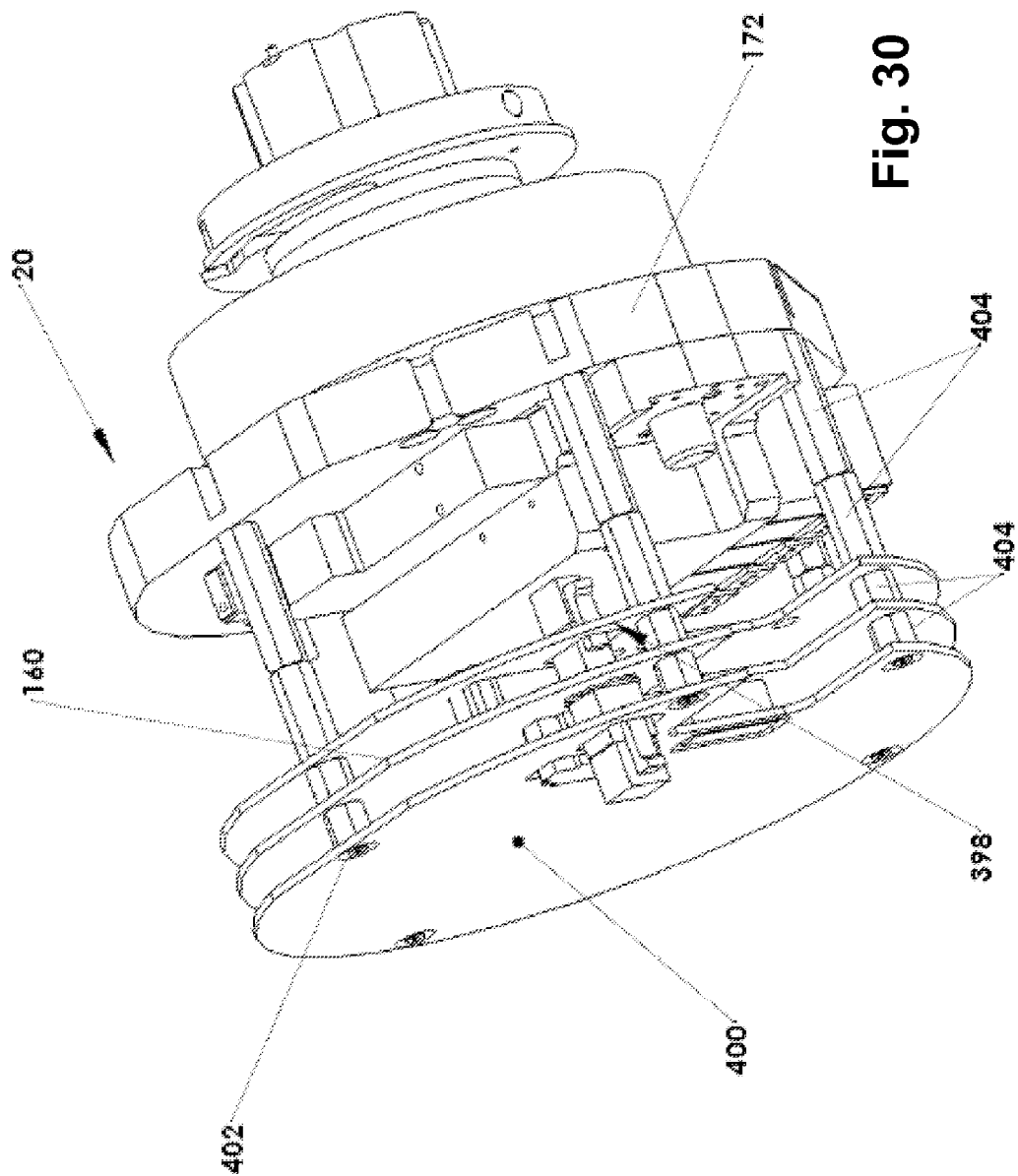
FIG. 30 shows a perspective view of an analytical processor assembly of the analytical module.

Referring now to FIGS. 28-30, the analytical processor assembly 20 includes an analytical PCA 160 secured between first and second mounting plates 398, 400. The analytical PCA 160 and the first and second mounting plates 398, 400 are secured together and to the secondary manifold plate 172 by a plurality of threaded bolts 402 fitted with nuts. Each of the bolts 402 extend through four spacers 404, two of which are disposed between the secondary manifold plate 172 and the first mounting plate 398, another one of which is disposed between the first manifold plate 398 and the analytical PCA 160, and still another one of which is disposed between the analytical PCA 160 and the second mounting plate 400. In this manner, the secondary manifold plate 172, the analytical PCA 160 and the first and second mounting plates 398, 400 are spaced apart from each other.

The analytical PCA 160 comprises a digital processor 408, which is designed for digital signal processing in real time. As used herein, the term "real time" means responding to stimuli within a bounded period of time. In an exemplary embodiment of the present invention, the digital processor 408 is a Blackfin® embedded processor available from Analog Devices and more particularly, a Blackfin® ADSP-BF533 embedded processor. The digital processor 408 provides fully digital based control of the flow control devices 210 and the cartridge heaters 150, 234 and can operate independently of the main CPU 24. The digital control provided by the digital processor 408 provides opportunities for performance enhancements and feature additions without adding hardware. The digital processor 408 communicates with memory 410, which may be serial flash memory having 1 MB storage space. The memory 410 stores all software algorithms run by the digital processor 408 to control the flow control devices 210 and the cartridge heaters 150, 234. In addition, the memory 410 stores a start-up program (or boot program) for the digital processor 408 that runs independently of the start-up program for the main CPU 24. Upon power-up of the gas chromatograph 10, the start-up program for the digital processor 408 interfaces with the memory 315 in the GC PCBA 184 to establish initial values for the process variables of the analytical module 16. More specifically, the start-up program: (1.) controls the cartridge heater 234 to set the temperature of the oven space to an initial value, which is retrieved from the memory 315; (2.) controls the cartridge heater 150 to set the temperature of the feed-through module 14 to an initial value, which is retrieved from the memory 315; (3.) controls the first and second pressure regulator valves 218, 220 to set the pressures of the carrier gas streams being fed to the first and second GC valves 188, 190 to initial values, which are retrieved from the memory 315; and (4) sets the pilot valve 216 so as to place the first and second GC valves 188, 190 in the "backflush" mode. Once the initial values for the process variables of the analytical module 16 are established by the start-up program, the digital processor 408 is ready to receive instructions from the main CPU 24 to run specific chromatographic analysis cycles.

The analytical PCA 160 has a serial communications interface with galvanic isolation. The serial interface can operate at up to 232Kbaud for development and in-house testing purposes. In addition, the serial interface can be coupled to a personal computer (PC) for diagnostics via an external hardware level translator. The PC is provided with software that allows real-time observation of high speed, high resolution data from any of the on-board systems. A temperature sensor is mounted to the circuit board.

The provision of the digital processor 408 separate from the CPU 372 (i.e., as a separate, stand-alone microprocessor) permits the digital processor 408 to process input signals from sensors and detectors and generate control output signals to the flow control devices 210 and the cartridge heaters 150, 234 without having to handle highly non-deterministic events, such as communications with other devices external to the gas chromatograph 10 and user inputs from the GUI, or having to run other software algorithms. This dedication of the digital processor 408 permits the digital processor 408 to process the input signals and generate the control output signals in a faster and more consistent manner. It also allows for software changes and enhancements the main CPU 24 without affecting those functions requiring real-time processing.

Connection to Feed-Through Module

The analytical module 16 is secured to the feed-through module 14 (and, thus, the housing 12) by a single bolt 299 that extends through the aligned main mounting holes 196, 198 in the primary and secondary manifold plates 170, 172 and is threadably received in the threaded bore 126 in the base 116 of the connection structure 110 of the feed-through module 14. In order to properly connect the analytical module 16 to the feed-through module 14, the guide posts 130 on the base 116 must be inserted into the guide holes 179 in the tongue 178 of the primary manifold plate 170. This ensures that the major face 178a of the tongue 178 properly interfaces with the second major face 124 of the base 116 so that the fluid openings 181 are connected to the inner passage openings 128. The bolt 299 has a hexagonal recess for receiving the end of a hexagonal driver, which is part of a tool kit provided with the gas chromatograph 10. The hexagonal driver has an elongated body so that the hexagonal driver can reach the bolt through the front access opening of the main section 22 of the housing 12.

IV. Termination Assembly

Figure 31:
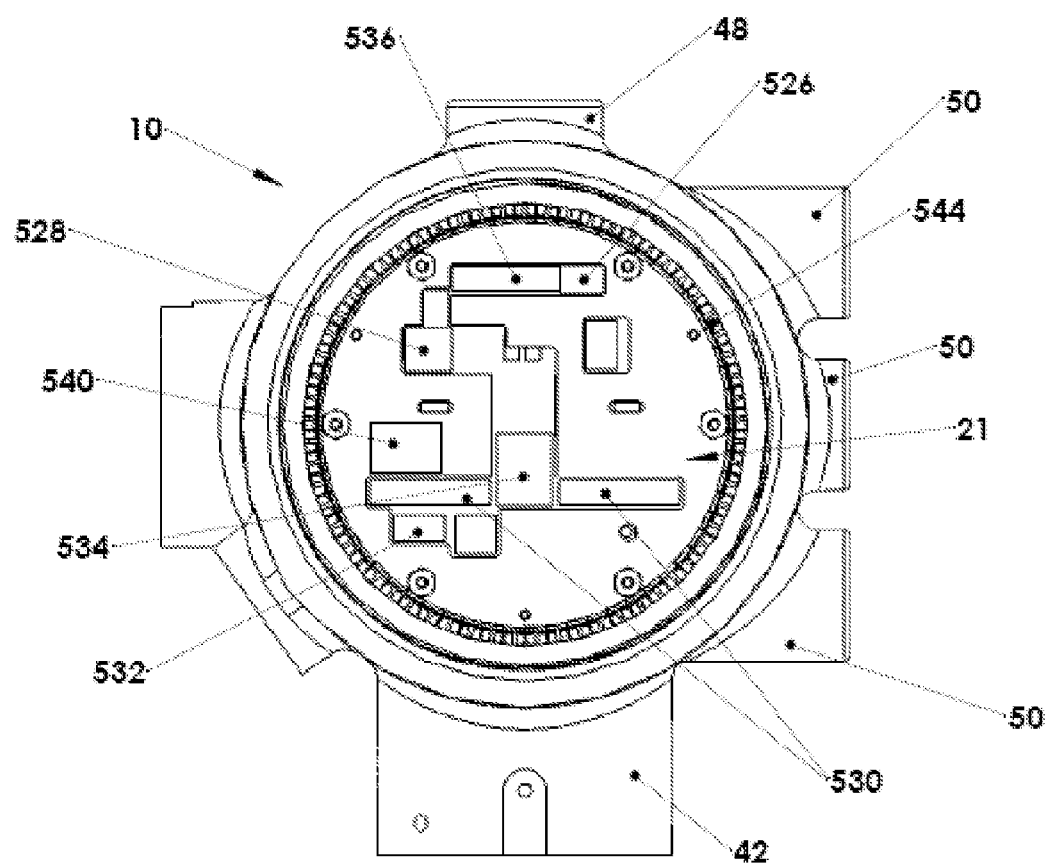
FIG. 31 shows a posterior end view of the gas chromatograph with a rear access cover removed from the housing to show an outer side of a termination assembly mounted inside the housing.
Figure 32:
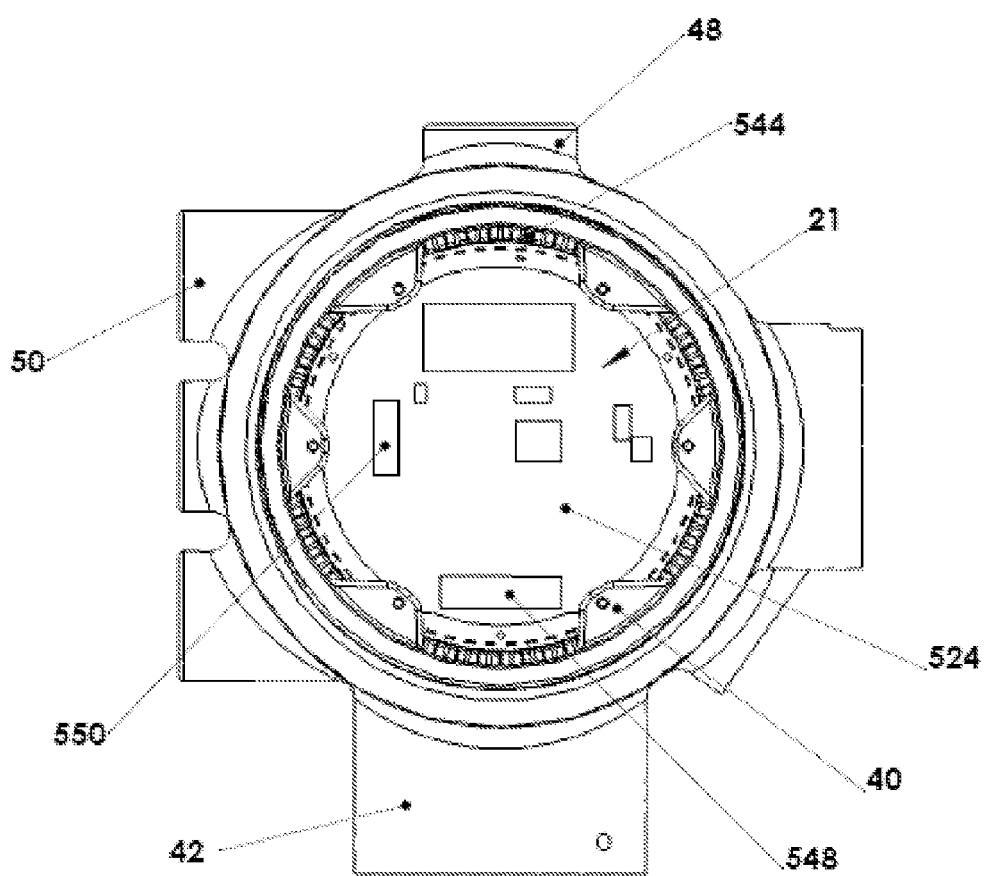
FIG. 32 shows an anterior end view of the gas chromatograph with a front access cover removed from the housing and the analytical module removed from the inside of the housing to show an inner side of the termination assembly mounted inside the housing.
Figure 33:
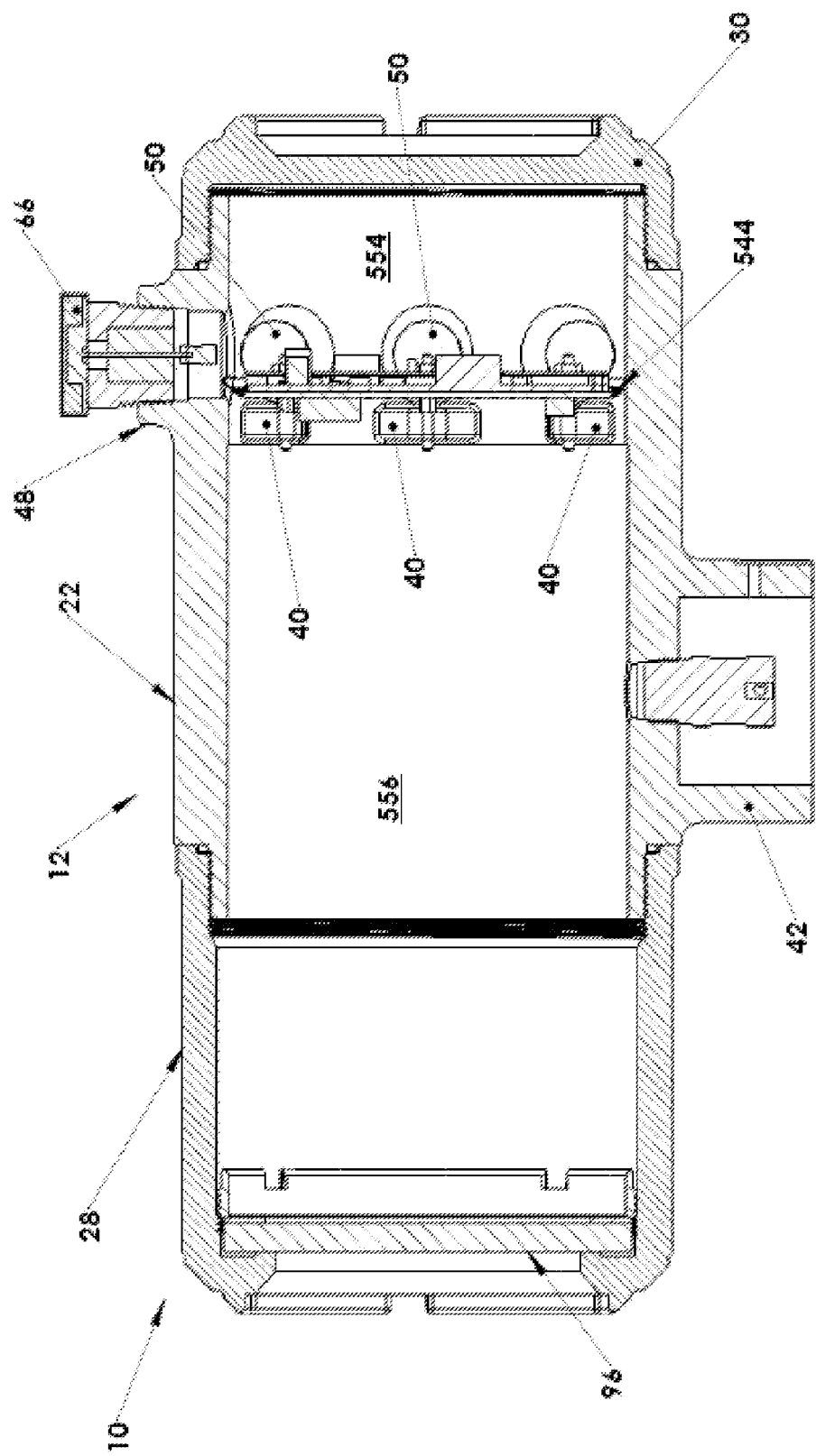
FIG. 33 shows a schematic drawing of the gas chromatograph divided into an RFI/EMI-protected compartment and an RFI/EMI-unprotected compartment.

Referring now to FIGS. 31-33, the termination assembly 21 comprises a disc-shaped printed circuit board 524 secured to the mounting ears 40 by screws. The termination assembly 21 provides connections for external communication and power wiring entering the gas chromatograph 10 from conduits connected to the conduit bosses 50. More specifically, the termination assembly 21 includes a power input plug 526, a non-configurable RS-232 serial port 528, a pair of configurable serial ports 530, and a plurality of input and output hardwire terminals. 536, all of which are mounted to an outer side of the PCB 524. The serial ports 530 can be configured for RS-232, RS-485 or RS-422. A wireless transceiver 540 may also be mounted to the outer side of the PCB 524. Alternately, the wireless transceiver 540 may be mounted to the main CPU 24, or elsewhere, such as circuit board disposed between the main CPU 24 and a mounting plate 376. The wireless transceiver 540 is connected between the main CPU 24 and the antenna 74. In combination with the antenna 74, the wireless transceiver 540 is operable to provide communication between the main CPU 24 and a wireless device (such as a personal digital assistant) using short-range radio frequency data transmission. The wireless transceiver 540 may be a Bluetooth capable transceiver that operates in a frequency band from 2.400 to 2.483 gigahertz (GHz) and provides up to a 720 kilobits per second (kbps) data transfer rate within a range of 10 meters and up to 100 meters with a power boost. Alternately, the wireless transceiver 540 may be an ultrawideband (UWB) transceiver operating in a frequency band from 3.1 to 10.6 GHz. UWB wireless communication is different from other forms of radio communication. Instead of using a carrier signal, a UWB transmission is comprised of a series of intermittent pulses. By varying the pulses' amplitude, polarity, timing, or other characteristic, information is coded into the transmission.

A conductive EMI/RFI gasket 544 is mounted inside the main section 22 of the housing 12 and is disposed around the PCB 524. More specifically, a radially inner circumferential surface of the EMI/RFI gasket 544 is in contact with circumferential edges of the PCB 524 as well as circumferential portions of the inner surface of the PCB 524. A radially outer circumferential surface of the EMI/RFI gasket 544 is in contact with the inner surface of the main section 22 of the housing 12. The EMI/RFI gasket 544 abuts the mounting ears 40 and may be secured thereto by the same screws that secure the PCB 524 to the mounting ears 40. The EMI/RFI gasket 544 may be comprised of a conductive metal, or a conductive elastomeric material. In one embodiment of the invention, the EMI/RFI gasket 544 is comprised of nickel plated beryllium copper.

As set forth above, the power input plug 526, the communication ports 530-534 and the hardwire terminals 536 are all mounted on the outer side of the PCB 524. Electrical circuits are connected to these ports and terminals and pass through the PCB 524 to an inner side of the PCB 524 where they are connected to a first cable connector 548 and/or a second cable connector 550. A filter circuit is connected into each of these electrical circuits and is operable to filter unwanted frequencies. In addition, the PCB 524 is provided with internal conducting plane layers and a top layer of copper near the hardwire terminals to help provide a low impedance path to the outer circumferential edge of the PCB 524. A layer of copper is disposed around the outer circumference of the PCB 524, on both the inner and outer sides of the PCB 524, and extends over the circumferential edge. The layer of copper is in contact with the EMI/RFI gasket 544. Thus, the EMI/RFI gasket 544 provides an electrical connection between the termination assembly 21 and the housing 12. In this manner, an EMI/RFI conduction path is provided from the termination assembly 21 to the housing 12 and, thus, ground.

The termination assembly 21 in combination with the EMI/RFI gasket 544 forms an RFI/EMI shield that divides the interior volume of the housing 12 into an RFI/EMI-protected compartment 554 and an RFI/EMI-unprotected compartment 556. The interior passages in the conduit bosses 50 and the first and second communication bosses 46, 48 open into the RFI/EMI-unprotected compartment 556. In addition, the power input plug, the pair of serial ports, the USB port, the Ethernet port, the plurality of hardwire input terminals and the plurality of hardwire output terminals are located in the RFI/EMI-unprotected compartment. In this manner, the communication and power cables and wiring entering the housing 12 (and which may be conducting RFI/EMI noise) are confined to the RFI/EMI-unprotected compartment. The termination assembly 21 and the EMI/RFI gasket prevent any RFI/EMI noise entering the RFI/EMI-unprotected compartment from moving into the RFI/EMI-protected compartment. The RFI/EMI-protected compartment is bounded on one end by the shield panel 96 and on the other end by the termination assembly 21 in combination with the EMI/RFI gasket. Since the housing 12 is grounded and both the shield panel 96 and the termination assembly 21/EMI/RFI gasket combination provide barriers to RFI/EMI noise, the RFI/EMI-protected compartment is protected from RFI/EMI noise. The analytical module 16 and the main electronics assembly 18 are disposed in the RFI/EMI-protected compartment and, thus, are protected from RFI/EMI noise.

Figure 34:
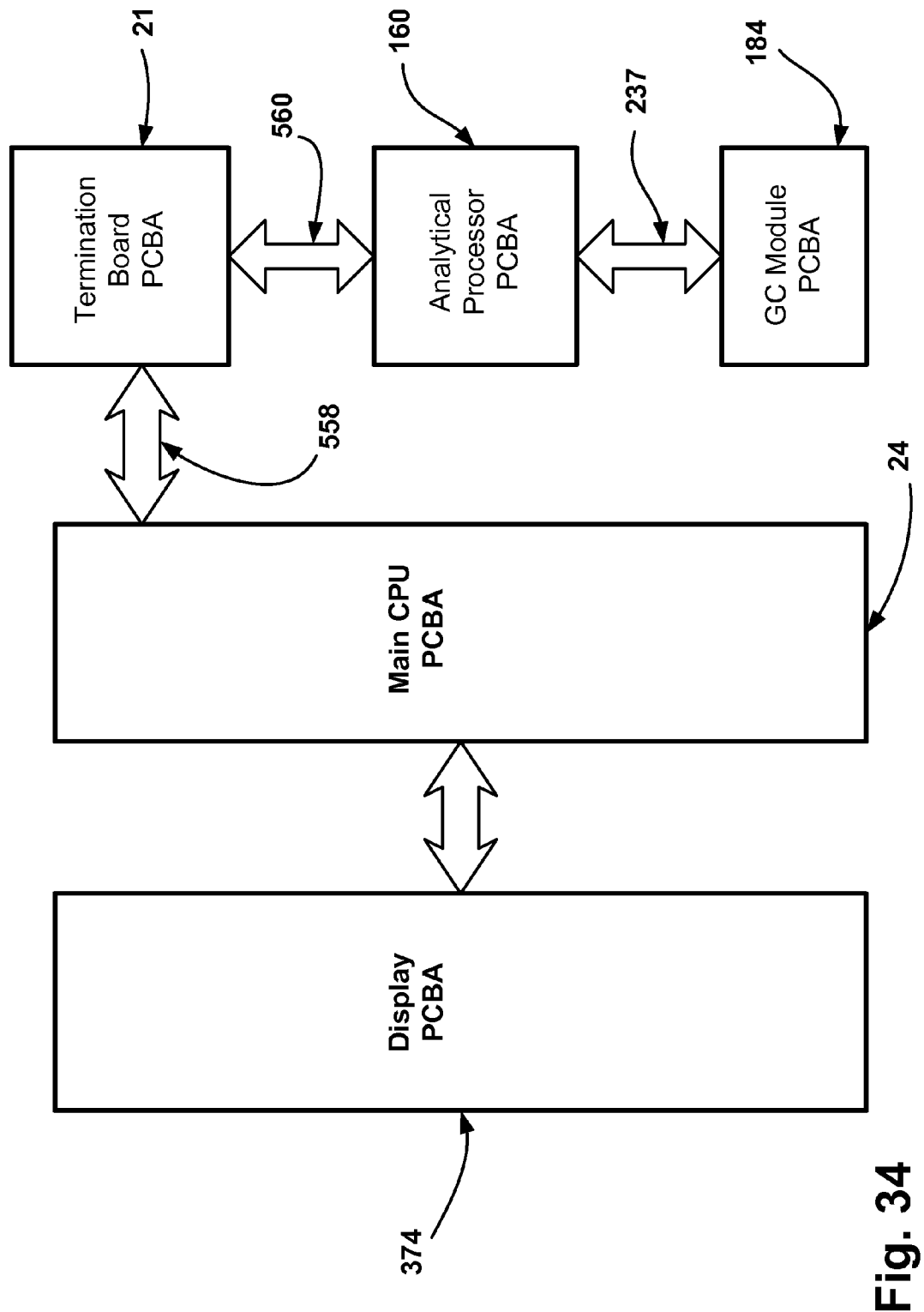
FIG. 34 shows a schematic drawing of the interconnection of an analytical processor printed circuit assembly, a main CPU, a termination assembly and a display printed circuit assembly.
Figure 35:
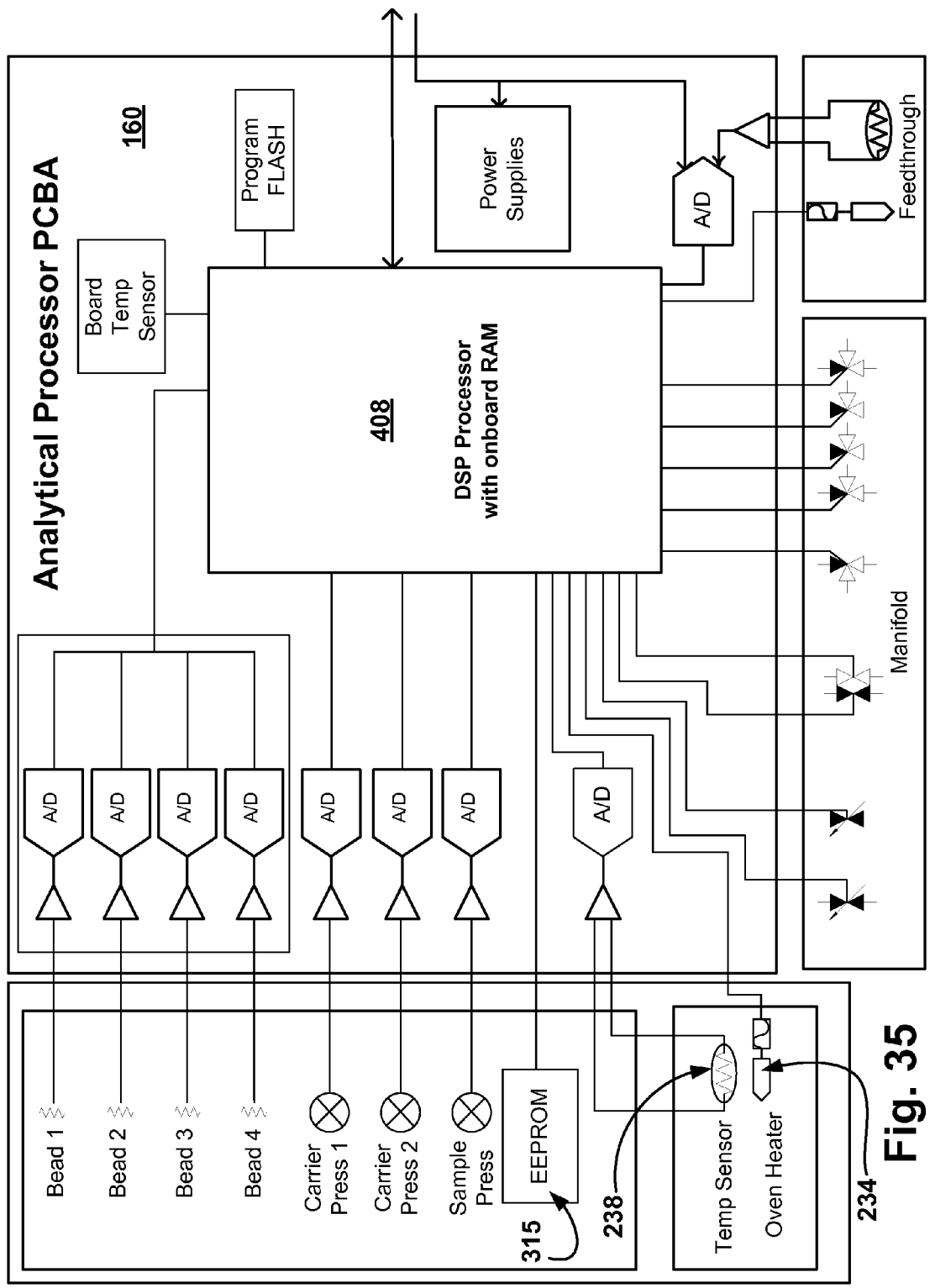
FIG. 35 shows a schematic drawing of the analytical processor printed circuit assembly.
Figure 36:
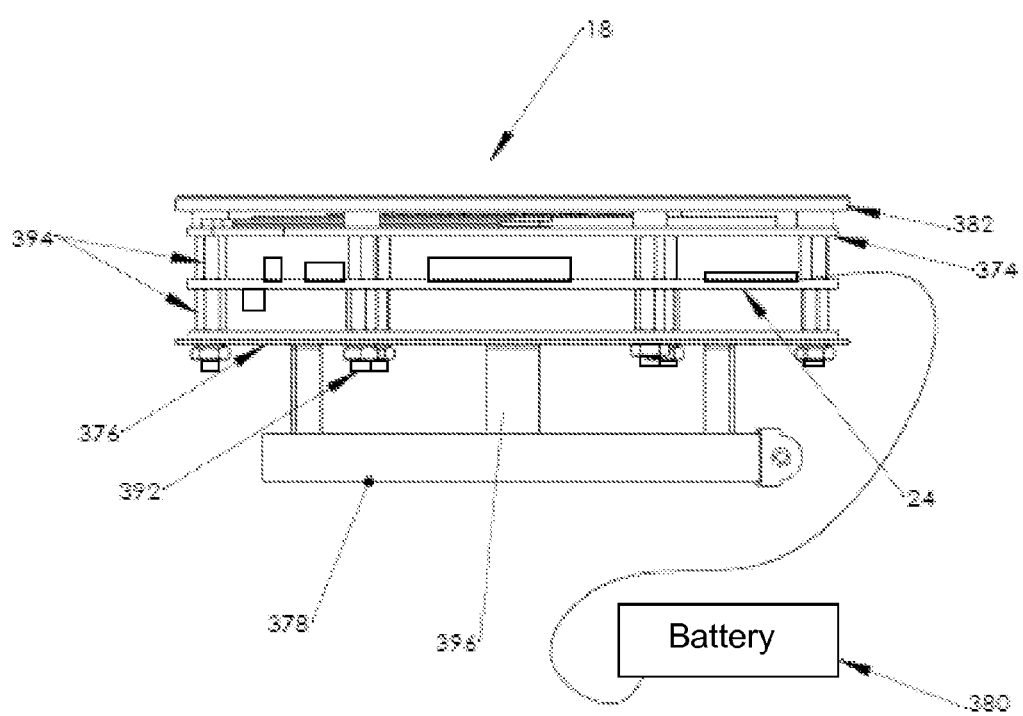
FIG. 36 shows a side elevational view of a main electronics assembly of the gas chromatograph.

As shown in FIG. 34, the main CPU 24 communicates with the analytical PCA 160 through the termination assembly 21. More specifically, the main CPU 24 is connected by a ribbon cable 558 (shown schematically in FIG. 34) to the first cable connector 548 on the termination assembly 21, and the analytical PCA 160 is connected by a cable 560 (shown schematically in FIG. 34) to the second cable connector 550 on the termination assembly 21. Communication from the main CPU 24 to the analytical PCA 160 travels through the ribbon cable 558 to the first cable connector 548 of the terminal assembly 21, through the PCB 524 to the second cable connector 550 and then through the cable to the analytical PCA 160. Communication from the analytical PCA 160 to the main CPU 24 occurs over the same path, but in the opposite direction. The GC PCBA 184 communicates with the analytical PCA 160 over the ribbon cable 237 that extends through the channel 236 in the heater plate 176.

V. Main Electronics Assembly

Referring now to FIGS. 34-37, the main electronics assembly 18 comprises the main CPU 24, a display PCA 374, a mounting plate 376, a mounting ring 378 and an outer bezel 382 with an enlarged opening.

The main CPU 24 handles system-level initialization, configuration, user interface, user command execution, connectivity functions, and overall system control of the electronics for the gas chromatograph 10. The main CPU 24 comprises a microprocessor mounted to a printed circuit board. The microprocessor may be an X86-type microprocessor, a RISC microprocessor (such as an ARM, DEC Alpha, PA-RISC, SPARC, MIPS, or PowerPC), or any other microprocessor suitable for use in a compact portable electronic device. In an exemplary embodiment, the microprocessor comprises a RISC core, which may be an ARM core, more particularly a 16/32-bit ARM9 core, still more particularly a 16/32-bit ARM920T core. The RISC core has a 16-bit Thumb instruction set, a 32-bit AMBA bus interface, a 5-stage integer pipeline, an 8-entry write buffer, separate 16KB Instruction and 16KB Data Caches and an MMU, which handles virtual memory management and is capable of supporting Windows® CE. An ARM9 core (including the ARM920T) is a 16/32 RISC processor designed by Advanced RISC Machines, Ltd. The RISC core is integrated with a set of common system peripherals, which includes a card interface for a secure digital (SD) flash memory card or a multimedia card, an LCD controller, an external memory controller, a multi-channel universal serial asynchronous receiver transmitter (USART), a watch dog timer, power management and USB host/device interface. An example of a commercially available microprocessor with a RISC core that may be used for the microprocessor is the S3C2410 microprocessor available from Samsung. An operating system, such as Windows® CE runs on the microprocessor. A memory system is connected to the microprocessor and includes volatile memory, such as a read-write memory (RAM) and a non-volatile memory such as boot read only memory (ROM). The non-volatile memory stores a start-up program (or boot program) for the microprocessor of the main CPU 24.

The main CPU 24 may also include an embedded TCP/IP stack and an HTTP web-server. In addition, the main CPU 24 may include a common gateway interface (CGI) module for communicating web page content to and from applications running in the main CPU 24 and the digital processor 408.

An SD socket is mounted to the printed circuit board of the main CPU and communicates with the card interface of the microprocessor. The SD socket holds an SD flash memory card. The SD flash memory card is small (measuring only 32 mm by 24 mm by 2.1 mm) and has a large amount of memory (such as 16MB) that can store data from the operation of the gas chromatograph 10. The SD flash memory card may be removed from the gas chromatograph 10 and easily transported to another location where the stored data from the gas chromatograph 10 may be retrieved. A lithium battery 380 is connected to the main CPU 24 for providing backup power thereto.

The display PCA 374 includes a circular printed circuit board (PCB) 383 mounted behind the outer bezel 382. A VGA LCD display screen 384 is mounted to an outer side of the PCB 383 such that the display screen 384 is visible through the opening in the outer bezel 382. An infrared port 388 and a plurality of backlight LEDs 390 are mounted to the outer side of the PCB 383. The infrared port 388 is aligned with an opening in the outer bezel 382 and is operable to transmit and receive data via near infrared light waves (850-900 nm) in accordance with the Infrared Data Association (IrDA) standard and communicates with the microprocessor through the USART. When the display PCA 374 is mounted in the housing 12, behind the shield panel 96, the display screen 384 is positioned so as to be viewable through the shield panel 96 and the infrared port 388 is positioned so as to be able receive and transmit infrared signals through the shield panel 96.

Figure 7:
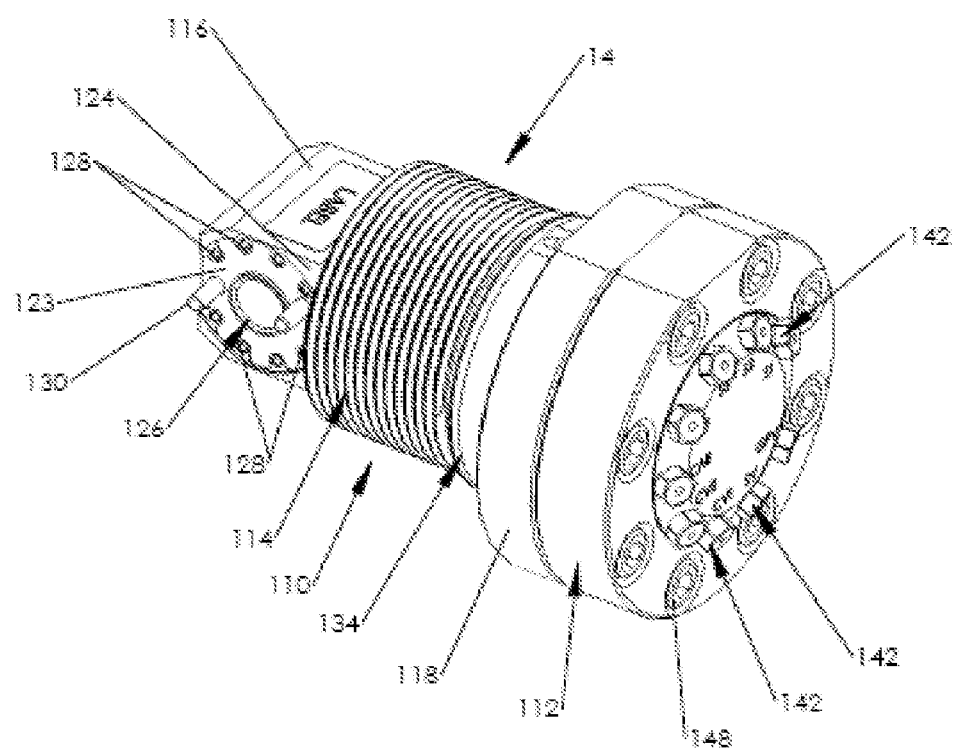
FIG. 7 shows a side perspective view of a feed-through module of the gas chromatograph.
Figure 8:
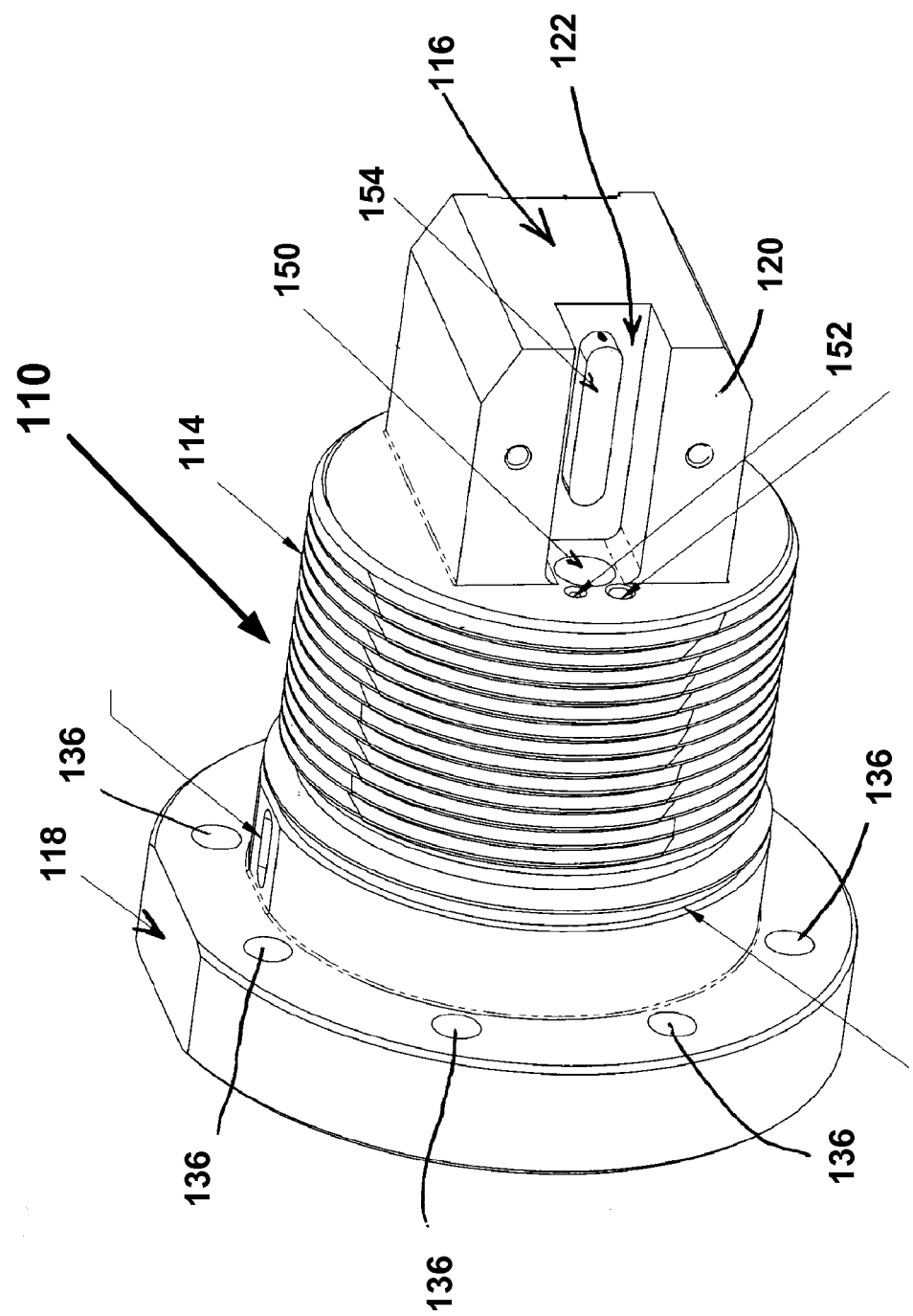
FIG. 8 shows a side perspective view of a connection structure of the feed-through module.
Figure 9:
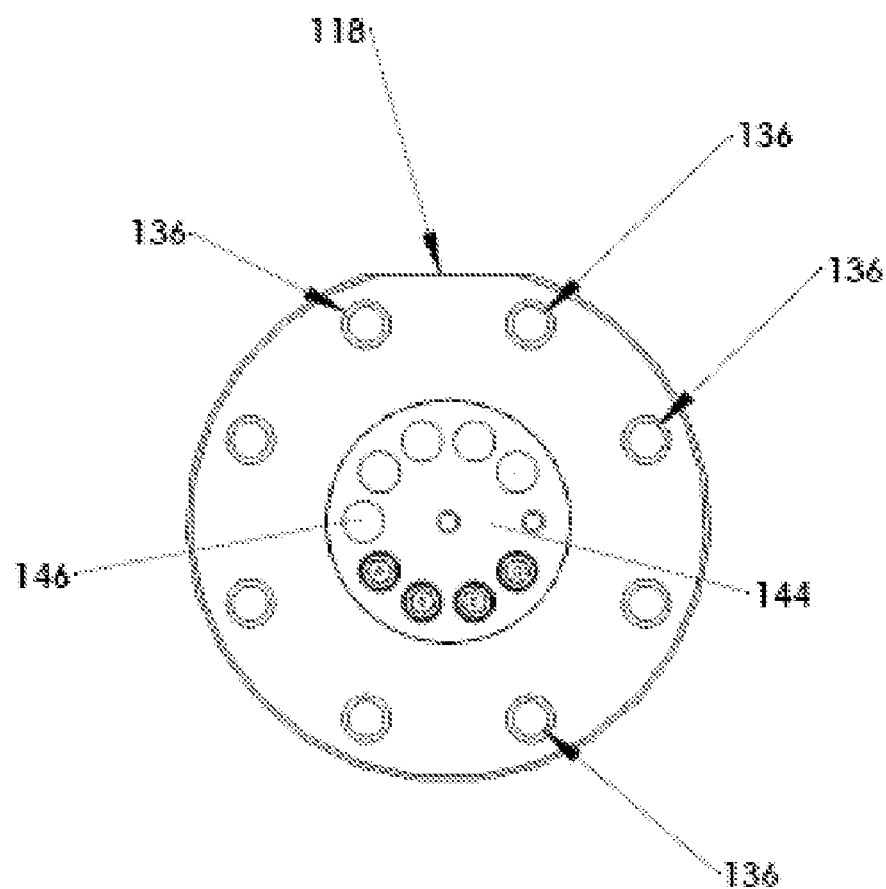
FIG. 9 shows an end view of the feed-through module with a feed plate of the feed-through module removed.
Figure 10:
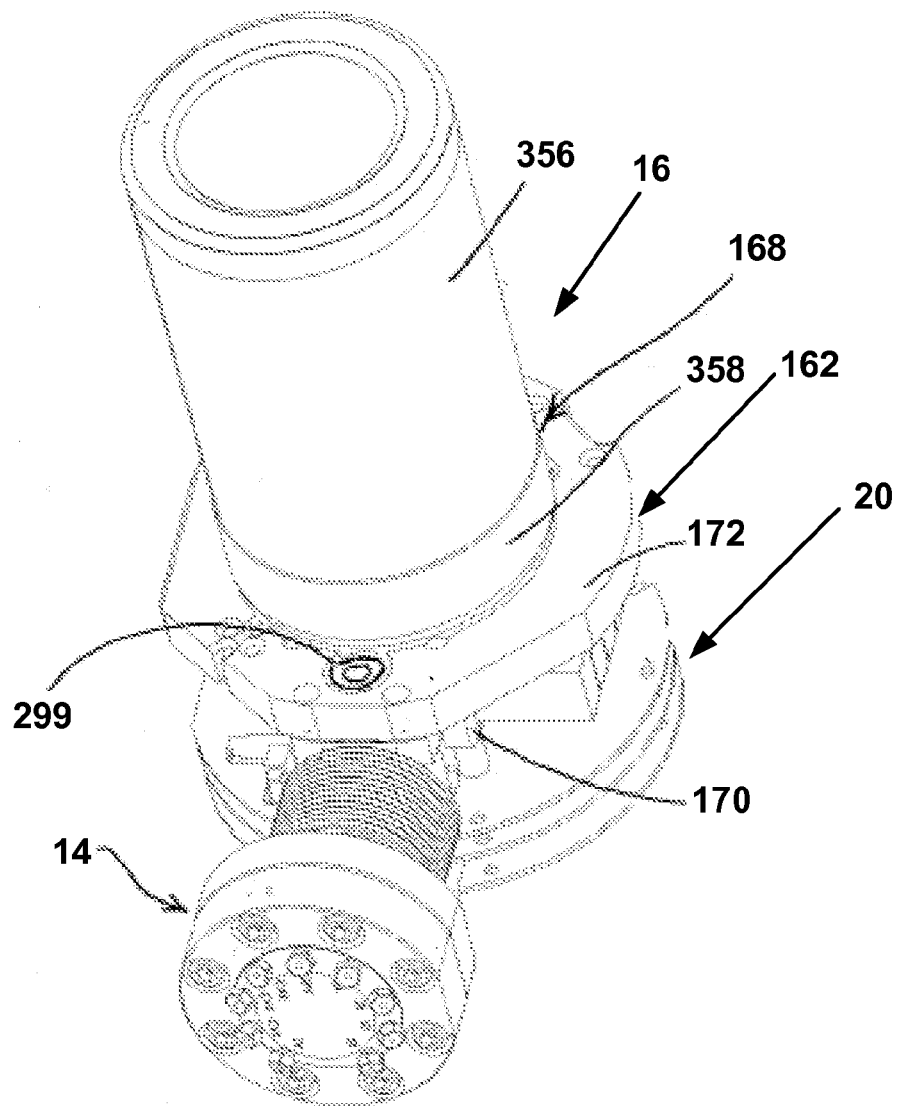
FIG. 10 shows a perspective view of the feed-through module secured to an analytical module of the gas chromatograph.
Figure 37:
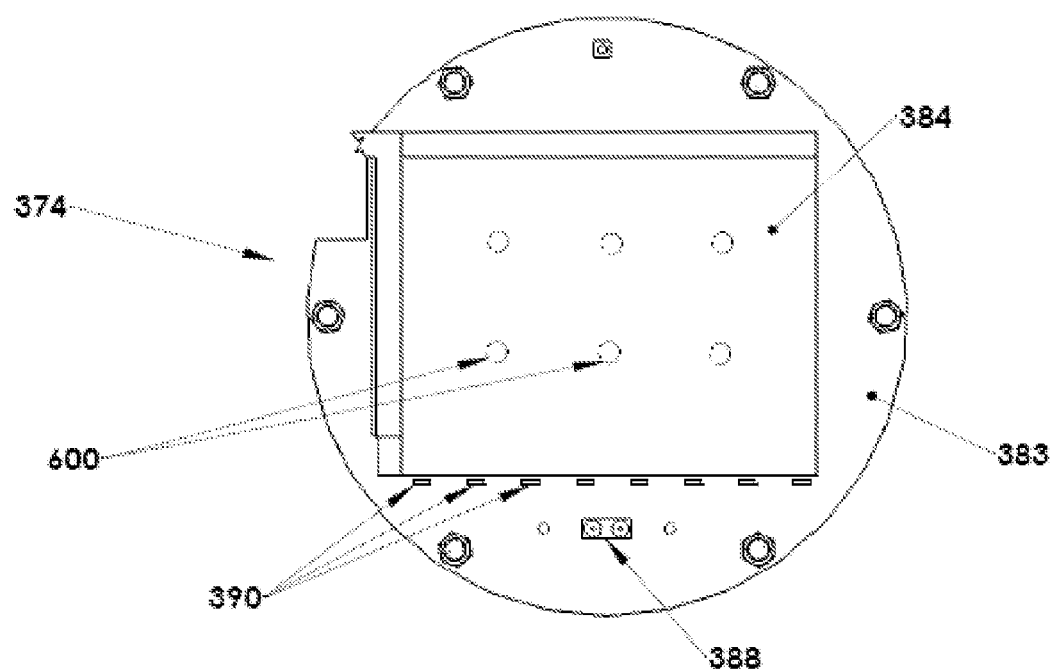
FIG. 37 shows a front plan view of an outer side of the display printed circuit assembly.

As shown in FIG. 37, a plurality of Hall-effect switches 600 are mounted to an inner side of the PCB 383 of the display PCA 374. Thus, the Hall-effect switches 600 are mounted behind the LCD display screen 384 and are separated from the LCD display screen 384 by the PCB 383 of the PCA 374. The number of Hall-effect switches 600 is limited and is substantially less than the number of liquid crystal cells forming the LCD display screen 384. The Hall-effect switches 600 are arranged in a pattern, such as a rectangle or a line, and are connected to the main CPU 24. As shown in FIG. 7, six Hall-effect switches 600 may be arranged in a rectangular pattern having a center that is aligned with the center of the LCD display screen 384. Each Hall-effect 600 switch may be a monolithic silicon chip that includes a Hall-effect element (HEE) coupled to a differential amplifier, which, in turn is coupled to a Schmitt-trigger threshold detector with built-in hysteresis. When a magnetic field is applied to the HEE, the HEE generates a Hall effect voltage, which is applied to the differential amplifier. The differential amplifier produces an output signal proportional to the Hall effect voltage. When the output signal from the differential amplifier is above a predetermined magnitude, the Schmitt-trigger threshold detector produces a digital "ON" signal, which is transmitted to the main CPU 24. Each of the Hall-effect switches 600 may be configured to activate, i.e., produce an "ON" signal when the Hall-effect switch 600 is disposed in a positive magnetic field. Alternately, each of the Hall-effect switches 600 may be configured to activate when the Hall-effect switch 600 is disposed in either a positive magnetic field or a negative magnetic field. As will be described more fully below, the Hall-effect switches 600 are used to navigate through a graphical user interface (GUI) of the gas chromatograph 10.

The display PCA 374, the main CPU 24 and the mounting plate 376 are secured together by a plurality of threaded bolts 392 fitted with nuts. Each of the bolts 392 extend through a pair of spacers 394, one of which is disposed between the display PCA 374 and the main CPU 24 and the other of which is disposed between the main CPU 24 and the mounting plate 376. In this manner, the display PCA 374, the main CPU 24 and the mounting plate 376 are spaced apart from each other. The mounting plate 376 is secured by a plurality of legs 396 to the mounting ring 378, which comprises a stainless steel hose clamp. The main electronics assembly 18 is mounted on the dewar 356 by disposing the mounting ring 378 over the dewar 356 such that the mounting plate 376 rests on the outer end of the dewar 356. A clamping mechanism of the mounting ring 378 is then adjusted to clamp the mounting ring 378 to the dewar 356.

VI. Communication with the GC

Figure 38:
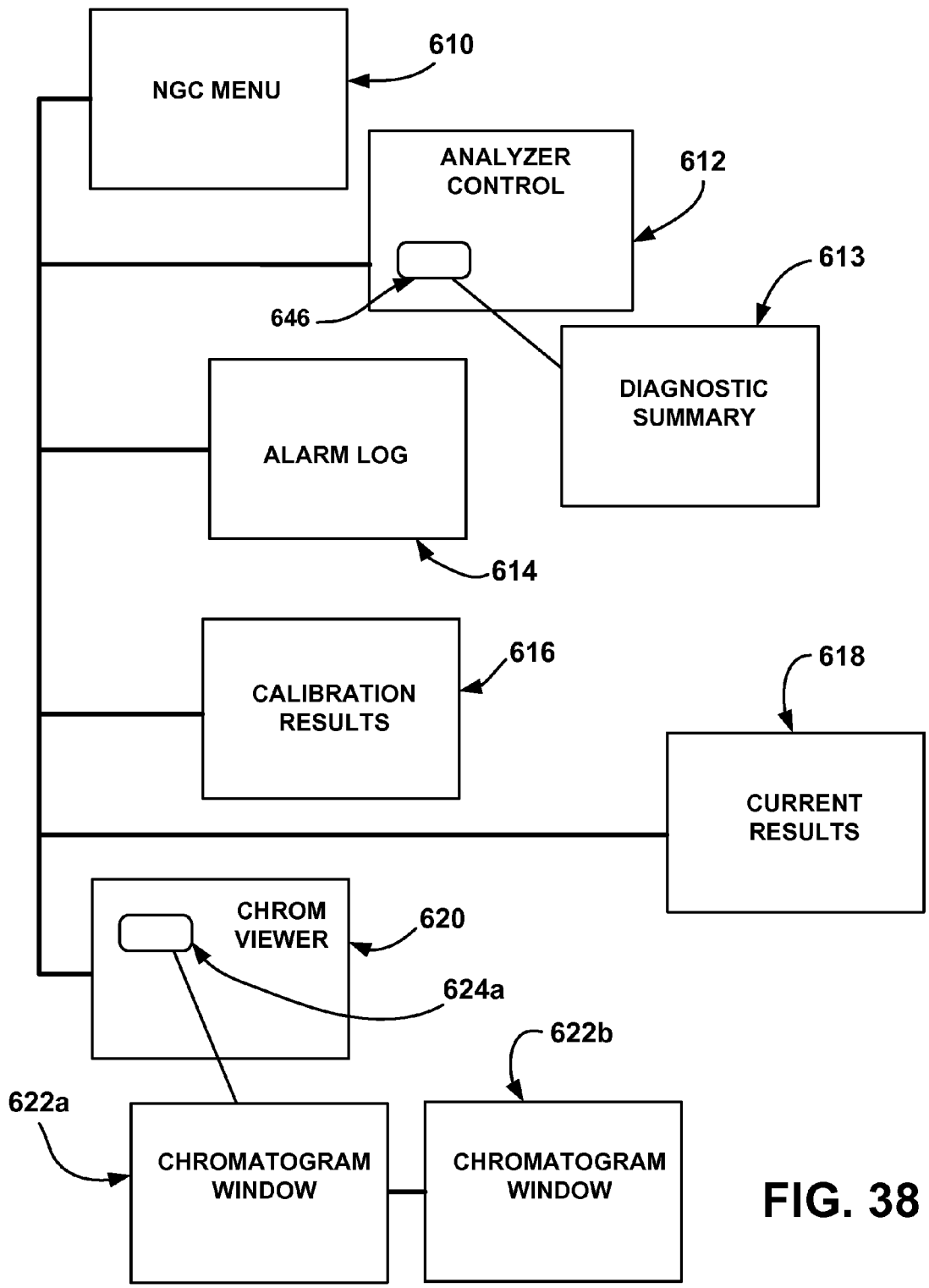
FIG. 38 shows windows of a graphical user interface (GUI) of the gas chromatograph.
Figure 39:
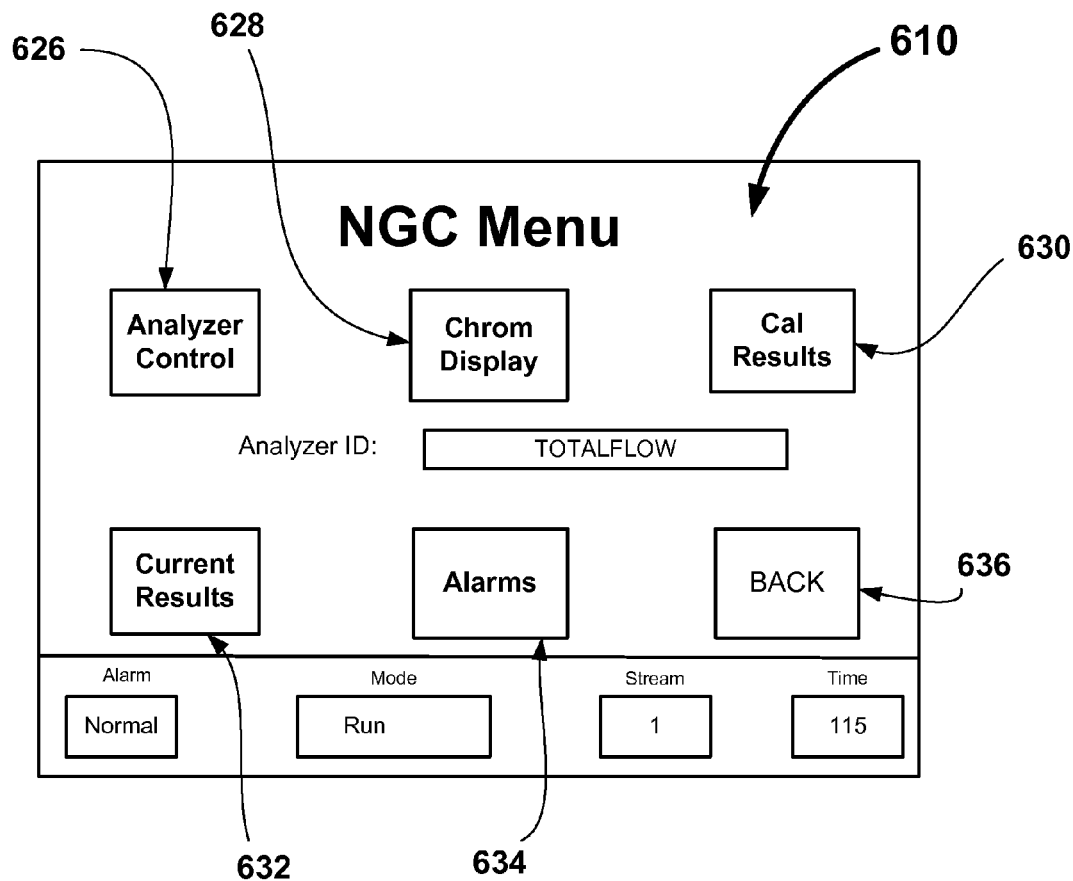
FIG. 39 shows an NGC Menu window of the GUI.
Figure 40:
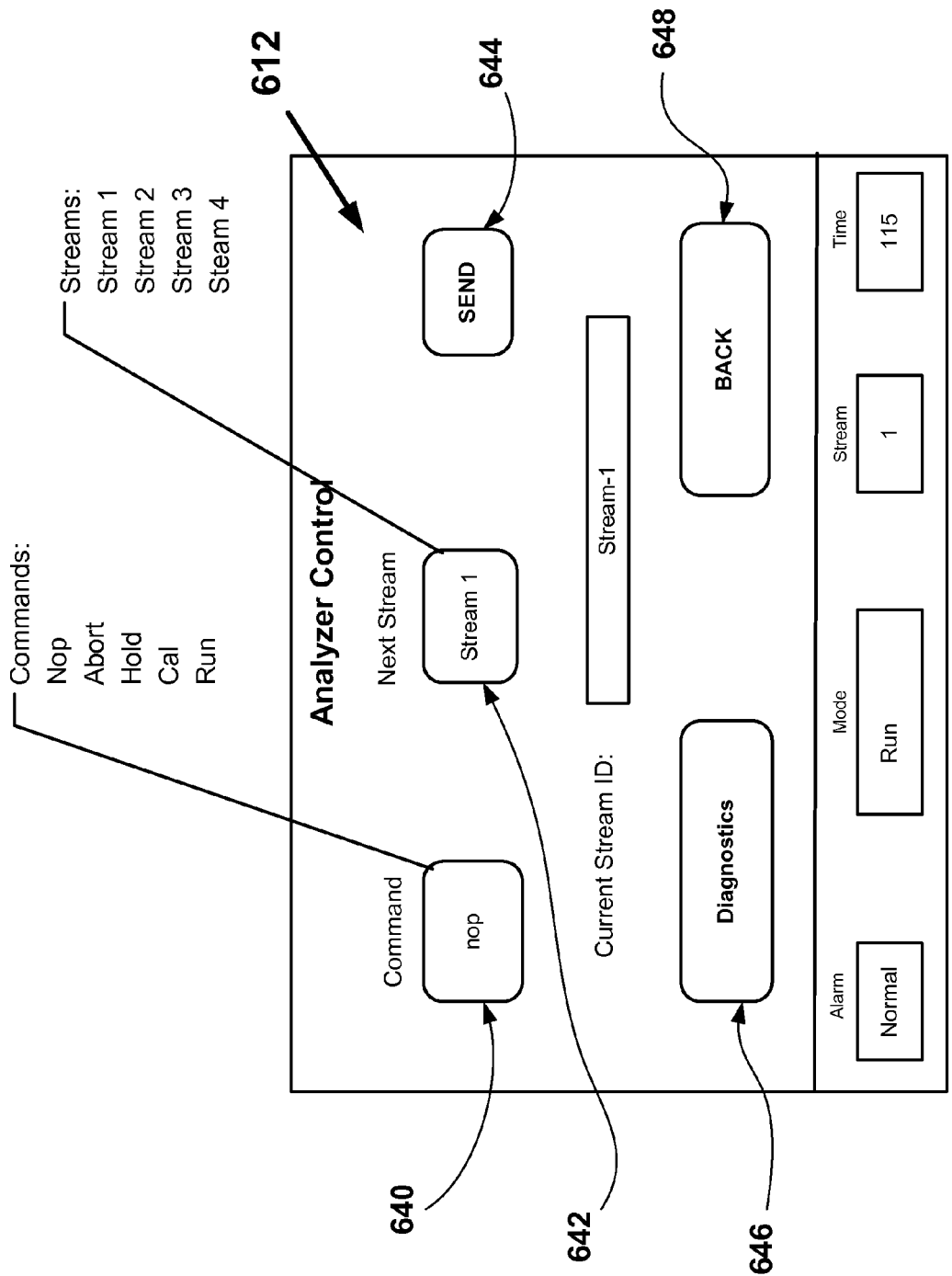
FIG. 40 shows an Analyzer Control window of the GUI.

The operating system running on the main CPU 24 supports the GUI, which allows a user to view and control the operation of the gas chromatograph 10. Referring now to FIGS. 38, 39 and 40, the GUI includes a plurality of windows that are displayable on the LCD display screen 384. The windows, which are generated and controlled by a GUI software application running on the main CPU 24, include an NGC Menu window 610, an Analyzer Control window 612, a Diagnostic Summary window 613, an Alarm Log window 614, a Calibration Results window 616, a Current Results window 618, a Chromatograph Viewer window 620, and chromatogram windows 622. Navigation through the windows and selection of options presented therein are accomplished using the Hall-effect switches 600 and a stylus (not shown) containing a magnet.

The NGC Menu window 610 includes six selection button icons, namely an Analyzer Control button 626, a Chrom Display button 628, a Cal Results button 630, a Current Results button 632, an Alarms button 634 and a Back button 636. The six buttons 626-636 are aligned with the six Hall-effect switches 600 that are disposed behind the LCD display window 384, respectively. Actuation of one of the buttons 626-634 will cause the window associated with the actuated button to be displayed on the LCD display window 384 in lieu of the NGC Menu window 610. For example, actuation of the Analyzer Control button 626 will cause the Analyzer Control window 612 to be displayed on the LCD display screen 384, selection of the Chrom Display button 628 will cause the Chromatograph Viewer window 620 to be displayed on the LCD display screen 384, and so on. A desired button is "actuated" by placing the stylus against or in close proximity to the shield panel 96 and in alignment with the desired button. This placement of the stylus activates the Hall-effect switch 600 aligned with the desired button. The "On" signal generated by the activated Hall-effect switch 600 is input to the GUI software application, which then causes the LCD display screen 384 to display the window associated with the selected button. The "actuation" of other buttons in other windows is performed in the same manner (i.e., with the stylus) and pursuant to the same operating mechanism (i.e., magnetically activating an aligned Hall-effect switch 660).

As set forth above, the Analyzer Control window 612 is accessed from the NGC Menu window 61. The Analyzer Control window 612 includes five selection button icons, namely a Command button 640, a Stream button 642, a Send button 644, a Diagnostics button 646 and a Back button 648. These five buttons are aligned with five of the six Hall-effect switches 600. The Command button 640 and the Stream button 642 are each operated in a scrolling manner to select an option. For example, the Stream button 642 is used to select one of four options, namely Stream 1, Stream 2, Stream 3, or Stream 4. When the Analyzer Control window 612 is being displayed on the LCD display screen 384, a first actuation of the Stream button 642 (i.e., activation (with the stylus) of the Hall-effect switch 600 aligned with the Stream button 642) causes the GUI software application to display Stream 1 in the Stream button 642 (as shown). In other words, Stream 1 is provisionally selected. After the Hall-effect switch 600 is deactivated by moving the stylus away from the LCD display screen 384, a second actuation of the Stream button 642 causes the GUI software application to display "Stream 2" in the Stream button 642, i.e., Stream 2 is provisionally selected. In the same manner, a third actuation provisionally selects Stream 3, a fourth actuation provisionally selects Stream 4, a fifth actuation provisionally selects Stream 1 again, and so on. Similar to the Stream button 642, the Command button 640 is actuated in a scrolling manner to display one of five commands in the Command button 604, i.e., to provisionally select one of five commands. These commands are: "Nop", "Abort", "Hold", "Cal" and "Run".

Once a user has provisionally selected a stream (e.g. Stream 1) and a command (e.g. Run), the user actuates the Send button 644 (i.e., activates the Hall-effect switch 600 aligned with the Send button 644), which causes the GUI software application to command the digital processor 408 to perform an analysis of the composition of Stream 1. In response, the digital processor 408, inter alia, actuates the sample valve 212*a* for Stream 1 to feed the gas of Stream 1 to the first and second sample loops 288, 290, and then, after a predetermined period of time, places the first and second GC valves 188, 190 into the "inject mode".

Actuation of the Diagnostics button 646 in the Analyzer Control window 612 causes the GUI software application to display the Diagnostic Summary window 613, which, inter alia, displays the pressures in the first and second columns 282, 286 and the temperature in the oven space. Actuation of the Back button 648 causes the GUI software application to go back and again display the NGC Menu window 610.

From the NGC Menu window 610, a user can also access the Current Results window 618 by actuating the Current Results button 630 and can access the Chrom Viewer window 620 by actuating the Chrom Display button 628. The Chrom Results window 618 displays the composition of a selected gas stream in a tabular format. The Chrom Viewer window 620 provides access to the chromatogram windows 622. The chromatogram windows 622 display chromatograms for the gases of Streams 1, 2, 3 and 4, respectively. In this regard, it should be noted that a chromatogram is a plot of the output signal of a detector (e.g. TCD 320 or TCD 324) versus time and shows the Gaussian peaks for the various gas components, as is described more fully below.

In addition to communicating with the gas chromatograph 10 through the GUI, a user at the site where the gas chromatograph 10 is installed may communicate with the gas chromatograph 10 through a mobile interface device (such as a laptop computer, or personal digital assistant) having a USB port, a Bluetooth transceiver and/or an infrared port. If the mobile device is equipped with a USB port, the mobile device may communicate with the gas chromatograph 10 over a cable connected to the communication port 88 of the gas chromatograph 10. If the mobile device is equipped with a Bluetooth transceiver, the mobile device may communicate with the gas chromatograph 10 via radio signals transmitted between the mobile device and the antenna 74 and the wireless transceiver in the gas chromatograph 10. If the mobile device is equipped with an infrared port, the mobile device may communicate with the gas chromatograph 110 via infrared light transmitted between the mobile device and the infrared port 388 of the gas chromatograph 110. It should be noted that if communication port 88 is in use, i.e., connected to another device, the infrared port 388 is made inactive.

Communication with the gas chromatograph 10 from a remote location may also be accomplished using a serial line connected to one of the serial ports 528, 530 in the termination assembly 21. The gas chromatograph 10 may also be connected through the Ethernet port 534 in the termination assembly 21 to a local area network (LAN), a wide area network (WAN), or the Internet. Web pages similar, if not identical to the windows 610-622 in the GUI, may be generated by the web server in the main CPU 24 and transmitted over the Internet to a user at a remote location.

VII. GC Features and Operation

It should be appreciated from the foregoing description that the gas chromatograph 10 has a modular construction that permits the gas chromatograph 10 to be quickly and easily disassembled and reassembled. This is advantageous because it permits the GC module 164 to be facilely replaced with another GC module that is constructed to analyze a gas different than the gas analyzed by the GC module 164. In this manner, the gas chromatograph 10 can be modified to analyze many different types of gases.

Each replacement GC module has substantially the same construction as the GC module 164, except for the columns 280-286. Each replacement GC module has columns that are specifically constructed for measuring a particular gas.

A GC module 164 may be swapped with a replacement GC module 164 while the analytical module 16 remains disposed in the housing 12 and secured to the feed-through module 14, or the GC module 164 may be swapped with a replacement GC module 164 after the entire analytical module 16 has been unfastened from the feed-through module 14 and removed from the housing 12. Either way, the front access cover 28 is unthreaded from the front collar 34 and removed. The clamping mechanism of the mounting ring 378 is then loosened and the main electronics assembly 18 is removed from the dewar 356. If the entire analytical module 16 is being removed, the bolt 299 is removed using the hexagonal driver and the analytical module 16 is pulled through the front access opening in the main section 22 of the housing 12. The dewar 356 is unthreaded from the cap 358 and removed, thereby exposing the oven enclosure 166. The oven enclosure 166 is then removed from engagement with the heater plate 176 by pulling the oven enclosure 166 away from the heater plate 176 and the rest of the manifold module 162. With the oven enclosure 166 so removed, the GC module 164 is now exposed. The ribbon cable 237 is first disconnected from the GC PCBA 184 and then the GC module 164 is rotated counter-clockwise to unthread the bolt 270 from the heater plate 176. After the GC module 164 is unthreaded and removed, the replacement GC module is then mounted to the manifold module 162 by threading its bolt 270 into the central bore 240 of the heater plate 17 and connecting the ribbon cable 237 to the replacement GC module. The oven enclosure 166 and the dewar 356 are then reinstalled. If the entire analytical module 16 was removed from the housing 12, the analytical module 16 is reinserted into the main section 22 through the front access opening thereof and secured to the feed-through module 14 with the bolt 299. The main electronics assembly 18 and the front access cover 28 are then reinstalled.

As with the GC module 164, each replacement GC module contains a memory 315 that stores calibration and other characterization data for the replacement GC module. The storage of calibration and other characterization data in the memories 315 of the GC module 164 and the replacement GC module, respectively, as opposed to other more centralized memory, such as the memory 410 for the digital processor 408, permits the GC module 164 to be swapped with the replacement GC module without having to reprogram memory, which greatly simplifies the replacement process.

Referring now to FIGS. 41 and 42, there are shown schematics of flow paths of sample gas and carrier gas through the gas chromatograph 10. More specifically, FIGS. 41 and 42 show schematics of a GC flow circuit 500 that comprises the inlet and vent paths through the feed-through module 14 and the first through sixth internal passage networks in the primary manifold plate 170, the secondary manifold plate 172, the spacer 174, the heater plate 176, the valve assembly 180 and the spool 278, respectively. The GC flow circuit 500 is, inter alia, represented by lines 502, 504, 506, 508, 510, 512, 514 and is interconnected with the electrical flow devices 210 and the first and second GC valves 188, 190. As set forth above, the first and second GC valves 188, 190 each have ports 1-10 and are movable between a "backflush" mode and an "inject" mode. Line 502 connects port 10 of the second GC valve 190 to the sample vent. Line 504 connects port 1 of the first GC valve 188, through the shut-off valve 214, to a selected one of the sample inputs. Line 506 connects port 8 of the first GC valve 188, through the first pressure regulator valve 218, to the carrier gas input. Line 508 connects port 8 of the second GC valve 190, through the second pressure regulator valve 220, to the carrier gas input. Line 510 connects port 4 of the first GC valve 188 to column vent 1. Line 512 connects the first and second GC valves 188, 190, through the pilot valve 216, to the carrier gas input. Line 514 connects port 4 of the second GC valve 190 to the column 2 vent. Line 516 connects port 10 of the first GC valve 188 to port 1 of the second GC valve 190.

When the first and second GC valves 188, 190 are in the "backflush" mode, as shown in FIG. 41, a stream of sample gas flows from a selected one of the sample inputs through line 504 to port 1 to port 2 of the first GC valve 188, through the first sample loop 288 and thence to port 10 of the first GC valve 188. From port 10 of the first GC valve 188, the stream of sample gas flows through line 516 to port 1 to port 2 of the second GC valve 190, through the second sample loop 290 and thence to port 9 to port 10 of the second GC valve 190.

The stream of sample gas then flows through line 502 to the sample vent. Thus, while the first and second GC valves 188, 190 are in the "backflush" mode, the first and second sample loops 288, 290 are filled with first and second gas samples, respectively. If the first and second GC valves 188, 190 are then moved to the "inject" mode, the first and second gas samples are trapped within the first and second sample loops 288, 290.

When the first and second GC valves 188, 190 are in the "inject" mode (as shown in FIG. 42), the carrier gas flows through lines 506, 508 and the first and second reference TCDs 318, 322 to the ports 8 of the first and second GC valves 188, 190. In the first GC valve 188, the carrier gas flows to port 9 and into the first sample loop 288, and in the second GC valve 190, the carrier gas flows to port 9 and into the second sample loop 290. The carrier gas entering the first and second sample loops 288, 290 forces the first and second gas samples trapped therein to exit the first and second sample loops 288, 290 through ports 2 of the first and second GC valves 188, 190, respectively. The first gas sample travels to port 3 of the first GC valve 188, then passes through the first preliminary column 280 to port 6 to port 7 of the first GC valve 188, then passes through the first column 282, travels to port 5 and exits the first GC valve 188 through port 4. Similarly, the second gas sample travels to port 3 of the second GC valve 190, then passes through the second preliminary column 284 to port 6 to port 7 of the second GC valve 190, then passes through the second column 286, travels to port 5 and exits the first GC valve 188 through port 4. After respectively exiting the first and second GC valves 188, 190, the first and second gas samples feed into the first and second sensor TCDs 320, 324, respectively, where the gas samples are analyzed, as will be described further below. The first and second gas samples then travel to the column 1 and column 2 vents through lines 510, 514, respectively.

After the first and second gas samples have been analyzed and the first and second GC valves 188, 190 are moved back to the "backflush" mode, carrier gas backflushes the first, second, third and fourth TCDs 318-324, the first and second preliminary columns 280, 284 and the first and second columns 282, 286 to remove remnants of the first and second gas samples. With regard to the first GC valve 188, the backflush travel path of the carrier gas is the first TCD 318, port 8, port 7, the first column 282, port 5, port 6, the first preliminary column 280, port 3, port 4, the second TCD 320 and then through line 510 to the column 1 vent. With regard to the second GC valve 190, the backflush travel path of the carrier gas is the third TCD 322, port 8, port 7, the second column 286, port 5, port 6, the second preliminary column 284, port 3, port 4, the fourth TCD 324 and then through line 514 to the column 2 vent.

As described above, the GC module 164 (which includes the TCDs 318-324 and the first and second GC valves 188, 190 and associated flow paths) receives a single stream of sample gas, divides the stream into a pair of gas samples and analyzes the gas samples in parallel. Such parallel analysis is faster than conventional serial analysis. It should be appreciated that the analysis speed can be increased further by utilizing additional GC valves and TCDs so as to analyze three or more samples in parallel.

For ease of description, only the analysis of the first gas sample will be discussed, it being understood that the analysis of the second gas sample is substantially the same. As the first gas sample travels through the columns 280, 282 the components of the first gas sample separate from one another by virtue of differences in their rates of interaction (absorption and de-absorption) with the adsorbents in the columns 280, 282. The different components are therefore retained in the columns 280, 282 for different lengths of time and arrive at the second TCD 320 (sense detector) at different, characteristic times. The design of the columns 280, 282, their operating conditions, such as temperature, and gas flow, are optimized and carefully controlled so as to provide good and consistent separation between the components.

Figure 43:
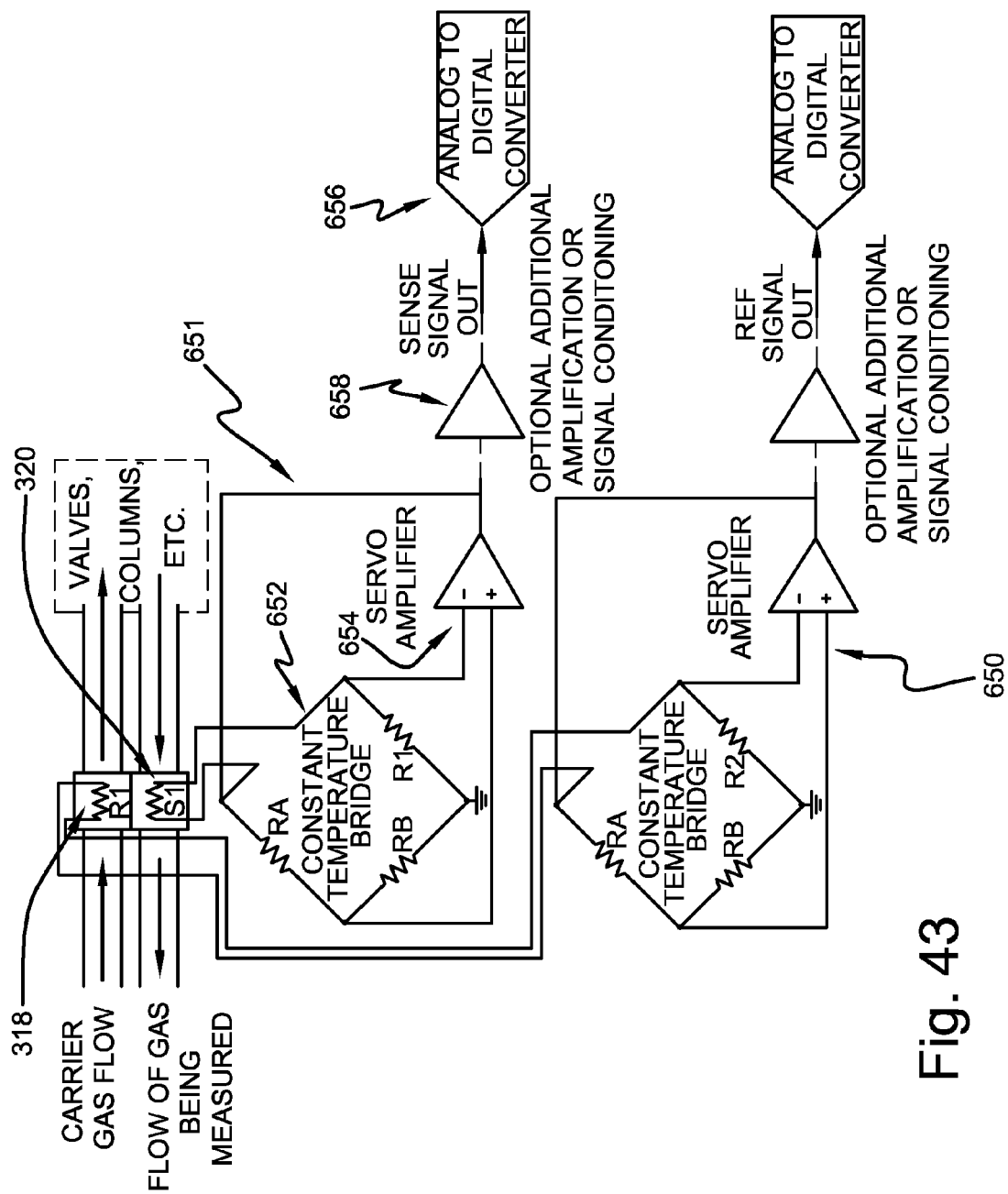
FIG. 43 shows a schematic electrical diagram of a first reference TCD and a first sensor TCD connected to amplifier circuits.

Referring now to FIG. 43, there is shown a schematic electrical diagram of the first reference TCD 318 and the first sensor TCD 320 connected to amplifier circuits 650, 651, respectively. Both the first reference TCD 318 and the first sensor TCD 320 are operated in a constant temperature mode, as will be described below. The amplifier circuits 650, 651 are mounted on the analytical PCA 160. For purposes of brevity, only the structure and operation of the first sensor TCD 320 and its amplifier circuit 651 will be described, it being understood that the structure and operation of the first reference TCD 318 and its amplifier circuit 650 is substantially the same, except the first reference TCD 318 is in contact with the carrier gas.

The amplifier circuit 651 comprises a Wheatstone bridge circuit 652 having two arms with resistances Ra and Rb, respectively. The other two arms have the first sensor TCD 320 and a resistance R1, respectively. The TCD 320 is in contact with the first gas sample exiting port 4 of the first GC valve 188 and operates in a self-heated mode. The bridge circuit 652 is connected to an operational amplifier 654 (acting as a servo amplifier), which is connected to an analog-to-digital (A-D) converter 656, which is, in turn, connected to the digital processor 408. Optionally, an amplifier 658 may be connected between the servo amplifier 654 and the A-D converter 656. The output of the servo amplifier 654 is fed back to the top of the bridge circuit 652.

The servo amplifier 654 and the bridge circuit 652 act in concert to maintain the temperature of the first sensor TCD 320 at a constant temperature. This happens because the servo amplifier 654 has its inverting and non-inverting inputs connected to the output terminals of the bridge circuit 652. The servo amplifier 654 acts to "servo" or steer the bridge circuit 652 outputs to a null voltage output (i.e. zero Volts) by increasing or decreasing its output voltage which provides the bias voltage for the bridge circuit 652. Because of this serving action of the servo amplifier 654, the current through the first sensor TCD 320 and the voltage across the first sensor TCD 320 are both varied which in turn correlates to the power being dissipated by the first sensor TCD 320 itself being raised or lowered to the point that it's temperature and thus it's resistance is always maintained at a constant value, consistent with the following relationship: Ra/Rb=S1/R1. The speed of thermal response of the first sensor TCD 320 as well as the output voltage of the servo amplifier 654 is such that the servo amplifier 654 can maintain the bridge circuit 652 nulled at all times during changes in the detector cell thermal conductivity due to the elution of the separated gas components corresponding to chromatographic peaks during the chromatographic cycle. The output voltage of the servo amplifier 654 has a direct correspondence to the power being dissipated by the first sensor TCD 320 itself. Since the first sensor CD 320 is maintained at a constant temperature, it is referred to as being operated in a constant temperature mode.

The location of the first sensor TCD 320 in the bridge circuit 652, and the connection of the inverting and non-inverting amplifier inputs, as the depicted, is exemplary. The location of the first sensor TCD 320 can actually be located in any one of the four arms of the bridge circuit 652, and through the proper connection of the inverting and non-inverting inputs of the servo amplifier 654, the same described behavior may be realized.

The output signal from the servo amplifier 654 (or the optional amplifier 658) of the amplifier circuit 654 has bell-like distributions, which are often referred to as Gaussian peaks. The portions of the output signal between the Gaussian peaks is attributable to the thermal conductivity and heat capacity of the carrier gas alone and is referred to as the "baseline", whereas each of the Gaussian peaks is attributable to the combination of the carrier gas and the thermal conductivity and heat capacity of a component of the first gas sample. The amount of separation between the Gaussian peaks is called "baseline separation".

The amplifier circuit 650 for the first reference TCD 318 generates an output signal for the carrier gas alone. This output signal does not contain Gaussian peaks.

The digitized output signal from the amplifier circuit 651 (the "sense" signal) and the digitized output signal from the amplifier circuit 650 (the "reference" signal) are each input to the digital processor 408. A software algorithm stored in the memory 410 and run by the digital processor 408 may be used to subtract the reference signal from the sense signal in order to remove the large signal attributable to the thermal conductivity of the carrier gas present at both the first reference TCD 318 and the first sensor TCD 320. As a result of this subtraction, any variation in oven space temperature affecting both the first and second TCDs 318, 320 is largely canceled. Of course, the subtraction software algorithm may be performed by the main CPU 24 instead of by the digital processor 408.

In lieu of using both the reference signal from the amplifier circuit 650 and the sense signal from the amplifier circuit 651 to quantify the components of the sample gas, Applicant have found that the same, if not better, results can be obtained using only the sense signal from the first sensor TCD 320. This is accomplished by a software algorithm stored in the memory system of the main CPU 24 and run on the microprocessor of the CPU 24 that, for each Gaussian peak, approximates a baseline that would be present if the Gaussian peak was not there. This approximation may be a straight line method connecting what would be the starting point of the Gaussian peak to the ending point of the Gaussian peak. The amplitude of each point along this line is then subtracted from each point along the Gaussian peak above it having the same time value. These difference values are then summed together to provide the total area under the curve (Gaussian peak). In other words, the curve is integrated. This integral value (area under the curve) represents the amount of a component present in the first gas sample and which is responsible for the Gaussian peak. Since the thermal conductivities and heat capacities of the various components are not the same, each of these peak areas are first multiplied by an appropriate correction factor for that specific peak called a response factor. Each of the response factors for the components being analyzed is determined empirically through the use of a calibration gas with known quantities of individual components.

The use of only the sense signal from the first signal TCD 320 to quantify the components in the first gas sample eliminates some of the errors that may occur in the signal subtraction method that arise from variations in flow, pressure and temperature of the gases at the first reference TCD 318 and the first sensor TCD 320.

For repeatable quantification of gas components, the temperature of the TCDs 318-324, the columns 280-286, the first and second sample loops 288, 290 and the first and second GC valves 188, 190 are closely regulated to maintain a constant temperature. This close regulation is facilitated by integrating the foregoing components into the GC module 164, mounting the GC module 164 on the heater plate 176, and enclosing both the GC module 164 and the heater plate 176 in the thermally insulating dewar 356, which is supported on the thermally insulating spacer 174. The heater plate 176 is heated by the cartridge heater 234. The temperature of the heater plate 176 is sensed by the oven temperature sensor 238, which is an NTC thermistor-type temperature sensor. The oven temperature sensor 238 generates a temperature signal which is transmitted to input circuitry in the analytical PCA 160, which conditions and digitizes the signal and then passes the signal to the digital processor 408. Using the digitized temperature signal from the oven temperature sensor 238, the digital processor 408 determines the correct control response for heating the GC module 164 and then outputs a pulse-width modulated control signal to a power transistor which then sources current to the cartridge heater 234. The digital processor 408 uses a software-implemented PID (Proportional-Integral-Derivative)-type control algorithm stored in the memory 410 to generate the control signal that controls the cartridge heater 234 and, thus, the temperature of the oven space. By having the temperature control algorithm performed in software, information about the temperature control process can be provided to the main CPU 24. Such information may include the oven power being used, which can provide valuable diagnostic information.

In addition to the temperature of the GC module 164, the pressure of the carrier gas is closely controlled. This is significant because even very small changes in gas pressure cause changes in gas density, which, in turn changes the thermal conductivity of the carrier, thereby resulting in a deflection in the output signal of the first reference TCD 318. Very small changes in the carrier gas pressure also causes pressure changes across the first GC valve 188, the columns 280, 282, etc., which also results in a deflection in the output signal of the first sensor TCD 320, as well as changes in the retention times of the Gaussian peaks, which affects measurement repeatability.

The first and second carrier pressure sensors 326, 328 generate pressure signals which are transmitted to input circuitry in the analytical PCA 160, which conditions and digitizes the signals and then passes the signals to the digital processor 408. Since the first and second carrier gas pressure sensors 326, 328 are located on the GC PCBA 184 in the thermally stable oven space defined by the oven enclosure 166 and the heater plate 176, the first and second carrier gas pressure sensors 326, 328 do not need to be temperature compensated. Using the digitized pressure signals from the first and second carrier pressure sensors 326, 328, the digital processor 408 determines the correct control response for providing carrier gas to the first and second GC valves 188, 190 and then outputs pulse-width modulated control signals to power transistors which then source currents to the first and second pressure regulating valves 218, 220. The digital processor 408 uses a software-implemented PID (Proportional-Integral-Derivative)-type control algorithm to generate the control signals that control the first and second pressure regulating valves 218, 220. By having the pressure control algorithm performed in software, information about the pressure control process can be provided to the main CPU 24. This information includes valuable diagnostic information about the control signals driving the first and second pressure regulating valves 218, 220, as well as the error term being computed within the software. Such information provides a measure of the effort being expended to control the first and second pressure regulating valves 218, 220, which, in turn can be used to determine if a leak exists in the GC flow circuit 500 by watching the trend of this control variable at the level of the Main CPU 24.

Since the feed-through module 14 can become nearly as cold as the ambient air around it on a cold day, the sampled gas that flows through it can experience similar temperatures. Depending on the type of sample gas, its composition may be such that some components will condense (making the transition from a gas phase to a liquid phase) and cling to the passage walls of the feed-through module 14 when exposed to these cold temperatures. The temperature at which this transition occurs is called the dewpoint. If this occurs, the gas chromatograph 10 will no longer be making an accurate measurement of the composition of the sampled gas, since some of the components will not reach the GC module 164 of the gas chromatograph in their correct proportions. Then, when the ambient temperature warms back up sufficiently, the condensed components will transition back to the gas phase and cause the measurements being made at that time to be in error again, with some components appearing in greater quantity than they really are in the gas being sampled at that time. An example of this is the dewpoint of Natural Gas with a BTU Value of 1050 BTU. Depending on the exact composition, this gas may have a dewpoint of around 30-40 deg F. By heating the feed-through module 14 to several degrees above that threshold, say 50-60 deg F., the accuracy of the gas chromatograph 10 is not impaired. This of course assumes that the tubing carrying the sampled gas is also heated from the source up to the feed-through module 14.

In order to prevent the condensation of the sampled gas in the feed-through module 14, the feed-through module 14 is provided with the cartridge heater 150 and the temperature sensor 152. The temperature of the connection structure 110 is sensed by the temperature sensor 152. The temperature sensor 152 generates a temperature signal which is transmitted to input circuitry in the analytical PCA 160, which conditions and digitizes the signal and then passes the signal to the digital processor 408. Using the digitized temperature signal from the temperature sensor 152, the digital processor 408 determines the correct control response for heating the connection structure 110 and then outputs a pulse-width modulated control signal to a power transistor which then sources current to the cartridge heater 150. The digital processor 408 uses a software-implemented PID (Proportional-Integral-Derivative)-type control algorithm to generate the control signal that controls the cartridge heater 150 and, thus, the temperature of the connection structure 110. By having the temperature control algorithm performed in software, information about the temperature control process can be provided to the main CPU 24.

It should be noted that the analytical PCA 160 utilizes pulse width modulation (PWM) drive for all the flow control devices 210. This permits 12V devices to be utilized with 24V system voltages because the digital processor 408 can dynamically change the average current being sourced to each device based on the instantaneous system voltage that it also measures. This feature also achieves a significant reduction in the power being dissipated by the devices under normal operation by using pick and hold current drive methods, often reducing the instantaneous power consumed by the devices by up to 75%, thereby reducing overall system power requirements, and making the gas chromatograph 10 more suitable for low power operation.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A gas chromatograph for analyzing gas, the gas chromatograph comprising:
  - (a.) an explosion-proof housing defining a single enclosed volume, the housing being elongated and having a longitudinal axis extending through opposing first and second ends of the housing;
  - (b.) a display screen disposed in the single enclosed volume of the housing and visible from the exterior of the housing;
  - (c.) a gas chromatograph (GC) assembly disposed in the single enclosed volume of the housing, the GC assembly comprising:
    a separation device operable to separate components of the gas;
    a detector for detecting the components of the gas; and
    a sample injection valve operable to inject the gas into the separation device; and
  - (d.) a sample selection valve operable to control flow of the gas to the sample injection valve, the sample selection valve being disposed in the single enclosed volume of the housing;
  - (e.) a transparent panel fastened to the housing at the first end, the display screen being visible through the transparent panel;
  wherein the housing comprises a body having an access opening formed therein and a cover removably disposed over the access opening, the cover forming the first end of the housing and the transparent panel being fastened to the cover; and
  wherein the GC assembly may be removed as a single unit from the housing through the access opening when the cover is removed from the body.

2. The gas chromatograph of claim 1, wherein the gas chromatograph is adapted for mounting to a stanchion having a longitudinal axis, and wherein the housing comprises a mount for mounting the gas chromatograph to the stanchion, the mount being adapted for attachment to the stanchion, whereby when the stanchion is attached to the mount, the longitudinal axis of the housing is disposed perpendicular to the longitudinal axis of the stanchion.

3. The gas chromatograph of claim 2, wherein the body is substantially cylindrical.

4. The gas chromatograph of claim 1, wherein the separation device comprises at least one column wound into a coil.

5. The gas chromatograph of claim 1, further comprising:
  an electronics assembly disposed in the housing and including a microprocessor, memory and a graphical user interface (GUI) software application stored in the memory and executable by the microprocessor to display a plurality of windows on the display screen, the windows containing information about the operation of the gas chromatograph.

6. The gas chromatograph of claim 1, wherein the gas chromatograph comprises a plurality of sample selection valves connected to gas inlet conduits and operable to selectively control the flow of gas from the inlet conduits to the sample injection valve, the sample selection valves being disposed in the single enclosed volume of the housing.

7. A gas chromatograph for analyzing gas, the gas chromatograph comprising:
- (a.) an explosion-proof housing defining a single enclosed volume;
- (b.) a display screen disposed in the single enclosed volume of the housing and visible from the exterior of the housing;
- (c.) a gas chromatograph (GC) assembly disposed in the single enclosed volume of the housing, the GC assembly comprising:
  a separation device operable to separate components of the gas;
  a detector for detecting the components of the gas; and
  a sample injection valve operable to inject the gas into the separation device; and
- (d.) a sample selection valve operable to control flow of the gas to the sample injection valve, the sample selection valve being disposed in the single enclosed volume of the housing; and
- (e.) a transparent panel fastened to the housing at the first end, the display screen being visible through the transparent panel, wherein the transparent panel provides shielding against radio frequency interference and comprises one or more transparent conductive layers.

8. The gas chromatograph of claim 7, wherein the transparent panel provides at least 30 dB of attenuation for frequencies in a range between 1 and 10,000 MHz.

9. The gas chromatograph of claim 7, wherein the transparent panel comprises at least one sheet of transparent material coated with at least one transparent conductive coating.

10. The gas chromatograph of claim 7, wherein the housing comprises a body having an access opening formed therein and a cover removably disposed over the access opening, the cover forming a first end of the housing and the transparent panel being fastened to the cover.

11. The gas chromatograph of claim 10, wherein at least a portion of the separation device extends beyond the plane of the access opening in the body so as to be disposed in the cover.

12. The gas chromatograph of claim 11, wherein the GC assembly and the sample selection valve may be removed as a single unit from the housing through the access opening when the cover is removed from the body.

13. The gas chromatograph of claim 10 wherein the GC assembly may be removed as a single unit from the housing through the access opening when the cover is removed from the body.

14. The gas chromatograph of claim 7, further comprising:
an electronics assembly disposed in the housing and including a microprocessor, memory and a graphical user interface (GUI) software application stored in the memory and executable by the microprocessor to display a plurality of windows on the display screen, the windows containing information about the operation of the gas chromatograph.

15. A gas chromatograph for analyzing gas, the gas chromatograph comprising:
- (a.) an explosion-proof housing defining a single enclosed volume;
- (b.) a display screen disposed in the single enclosed volume of the housing and visible from the exterior of the housing;
- (c.) a gas chromatograph (GC) assembly disposed in the single enclosed volume of the housing, the GC assembly comprising:
  a separation device operable to separate components of the gas;
  a detector for detecting the components of the gas; and
  a sample injection valve operable to inject the gas into the separation device; and
- (d.) a sample selection valve operable to control flow of the gas to the sample injection valve, the sample selection valve being disposed in the single enclosed volume of the housing;
- (e.) a manifold to which the sample selection valve is mounted; and
- (f.) a double-walled enclosure disposed over the GC assembly and fastened to the manifold.

16. The gas chromatograph of claim 15, wherein the display screen is releasably mounted to the double-walled enclosure.

17. The gas chromatograph of claim 16, further comprising:
a first printed circuit board to which the display screen is mounted;
a second printed circuit board secured to the first printed circuit board; and
a mounting plated secured to the first and second printed circuit boards.

18. The gas chromatograph of claim 16, wherein the display screen is mounted to the double-walled enclosure by a clamping ring.

19. The gas chromatograph of claim 16, wherein the double-walled enclosure comprises a Dewar flask.

* * * * *